United States Patent
Bujak et al.

(10) Patent No.: US 10,071,267 B2
(45) Date of Patent: Sep. 11, 2018

(54) METHOD, SYSTEM AND USE FOR THERAPEUTIC ULTRASOUND

(71) Applicant: 2442033 ONTARIO INC., Toronto (CA)

(72) Inventors: Matthew Bujak, Toronto (CA); F. Stuart Foster, Toronto (CA); Michael Hynes, Oakville (CA)

(*) Notice: Subject to any disclaimer, the term of this patent is extended or adjusted under 35 U.S.C. 154(b) by 0 days.

(21) Appl. No.: 15/708,702

(22) Filed: Sep. 19, 2017

(65) Prior Publication Data

US 2018/0064962 A1    Mar. 8, 2018

Related U.S. Application Data

(63) Continuation of application No. 14/543,215, filed on Nov. 17, 2014, now Pat. No. 9,789,344.

(60) Provisional application No. 61/904,763, filed on Nov. 15, 2013.

(51) Int. Cl.
*A61H 1/00* (2006.01)
*A61N 7/00* (2006.01)
*A61F 9/007* (2006.01)

(52) U.S. Cl.
CPC .............. *A61N 7/00* (2013.01); *A61F 9/007* (2013.01)

(58) Field of Classification Search
CPC .............................. A61N 7/00; A61H 23/0245
See application file for complete search history.

(56) References Cited

U.S. PATENT DOCUMENTS

| | | |
|---|---|---|
| 2002/0082527 A1 | 6/2002 | Liu et al. |
| 2006/0206173 A1 | 9/2006 | Gertner |
| 2007/0091265 A1 | 4/2007 | Kardon et al. |
| 2007/0276232 A1 | 11/2007 | Towe |
| 2008/0114420 A1 | 5/2008 | Korb et al. |
| 2008/0215039 A1 | 9/2008 | Slatkine et al. |
| 2011/0319794 A1 | 12/2011 | Gertner |
| 2012/0016239 A1 | 1/2012 | Barthe et al. |
| 2014/0221908 A1 | 8/2014 | Sonsino et al. |

OTHER PUBLICATIONS

S. K. Das et al., "Computational techniques for fast hyperthermia temperature optimization", Med. Phys., 1999, pp. 319-328, 26(2).
L. Demkowicz et al, "Analysis of a coupled finite-infinite element method for exterior helmholtz problems", Numer. Math., 2001, pp. 43-73, vol. 88.
F. Despa et al., "The relative thermal stability of tissue macromolecules and cellular structure in burn injury", Burns, 2005, pp. 568-577, vol. 31.
S. A. Divall et al., "Finite difference modelling of the temperature rise in non-linear medical ultrasound fields", Ultrasonics, 2000, pp. 273-277, vol. 38.

(Continued)

*Primary Examiner* — Hien Nguyen
(74) *Attorney, Agent, or Firm* — Norton Rose Fulbright Canada LLP; Maya Medeiros

(57) ABSTRACT

The described embodiments relate to methods, systems and uses for therapeutic ultrasound, and in particular, to methods, systems and uses for therapeutic ultrasound and contact lenses for treating or alleviating eye conditions. The described embodiments relate to methods, systems and uses that involve an ultrasound device configured for treatment of an eye condition and a contact lens protects ocular tissue of the eye and forms a chamber of air.

13 Claims, 36 Drawing Sheets

(56) References Cited

OTHER PUBLICATIONS

C. H. Farny, "Scanning acoustic microscope for characterization of arterial plaque", Boston University College of Engineering—Thesis, 2001.
F.S. Foster et al., "The ultrasound macroscope: initial studies of breast tissue", Ultrasonic Imaging, 1984, pp. 243-261, vol. 6.
E. Franceschini, "Experimental ultrasound characterization of tissue-mimicking phantoms with high scatterer volume fractions", Proceedings of the Acoustics, 2012, pp. 23-27.
B. R. Friedland et al., "A novel thermodynamic treatment for meibomian gland dysfunction", Current Eye Research, 2011, pp. 79-87, 36(2).
W. J. Fry et al., "Determination of absolute sound levels and acoustic absorption . . . probes-theory", The Journal of the Acoustical Society of America, 1954, pp. 294-310, 26(3).
W. J. Fry et al., "Determination of absolute sound levels and acoustic . . . probes-experiment". The Journal of the Acoustical Society of America, 1954, pp. 311-317, 26(3).
Gokul K.C. et al., "FEM approach for transient heat transfer in human eye", Applied Mathematics, 2013, pp. 30-36, vol. 4.
S.A. Gross et al., "Comprehensive compilation of empirical ultrasonic properties of mammalian tissues", J. Acoust. Soc. Am., 1978, pp. 423-457, 64(2).
S.A. Gross et al., "Ultrasonic absorption and attenuation in mammalian tissues", Ultrasound in Med. & Biol., 1979, pp. 181-186, vol. 5.
E. Goto et al., "Treatment of non-inflamed obstructive meibomian gland dysfunction by an infrared warm compression device", Br J Ophthalmol, 2002, pp. 1403-1407, vol. 86.
C. Guittet et al., "High-frequency estimation of the ultrasonic attenuation . . . simulation and in vivo results", Ultrasound in Med. & Biol., 1999, pp. 421-429, 25(3).
C. Guittet et al., "In vivo high-frequency ultrasonic characterization of human dermis", IEEE Transactions on Biomedical Engineering, 1999, pp. 740-746, 46(6).
C. Guittet et al., "Ultrasonic tissue characterization for the backscattering estimation . . . at high frequencies: 20-100MHz", IEEE Ultrasonics Symposium, 1996, pp. 1081-1084.
A. W. Guy et al., "Therapeutic applications of electromagnetic power", Proceedings of the IEEE, 1974, pp. 55-81, 62(1).
J. J. Heys et al., "A boussinesq model of natural convection in the human eye . . . Krukenberg's Spindle", Annals of Biomedical Engineering, 2002, pp. 392-401, vol. 30.
Professor Kenneth R. Holmes, "Thermal Properties", pp. 1-14.
P.R. Hoskins, "Physical properties of tissues relevant to arterial ultrasound imaging and blood velocity measurement", Ultrasound in Med. & Biol., 2007, pp. 1527-1539, 33(10).
J. J. Dutton et al., "Eyelid anatomy and physiology with reference to blepharoptosis", Evaluation and Management of Blepharoptosis, 2011, pp. 13-26, Chapter 3.
T. Huttunen et al., "Optimal control in high intensity focused ultrasound surgery", Department of Physics, University of Kuopio, Finland, pp. 169-195.
A. J. Bron et al., "Functional aspects of the tear film lipis layer", Experimental Eye Research, 2004, pp. 347-360, vol. 78.
A. J. Bron et al., "Meibomian gland disease. Classification and grading of lid changes", Eye, 1991, pp. 395-411, vol. 5.
R. Bude et al., "An easily made, low-cost, tissue-like ultrasound phantom material", J Clin Ultrasound, 1995, pp. 271-273, vol. 23.
A. Caduff et al., "Cutaneous blood perfusion as a perturbing factor for noninvassive glucose monitoring", Diabetes Technology & Therapeutics, 2010, pp. 1-9, 12(1).
N. Charkoudian, "Skin blood flow in adult human thermoregulation: how it works, when it does not, and why", Mayo Clin Proc., 2003, pp. 603-612, vol. 78.
I. C. Franzco, "Fluids of the ocular surface: concepts, functions and physics", Clinical and Experimental Ophthalmology, 2012, pp. 634-643, vol. 40.
R. C. Chivers, "Ultrasonic velocity and attenuation in mammalian tissues", J. Acoust. Soc. Am., 1978, pp. 940-953, 63(3).
K. Hynynen, "The role of nonlinear ultrasound propagation during hyperthermia treatments", Med. Phys., 1991, pp. 1156-1163, 18(6).
K. Hynynen et al., "Temperature measurements during ultrasound hyperthermia", Med. Phys., 1989, pp. 618-626, 16(4).
Jorgen Arendt Jensen, "Users' guide for the field II program", Department of Electrical Engineering, Technical University of Denmark, May 2014, Release 3.24, 67 pgs.
K. Hynynen et al., "Temperature distributions during local ultrasound induced hyperthermia in vivo", Ultrasonics Symposium IEEE, 1982, pp. 745-749.
F. Ihlenburg et al., "Reliability of finite element methods for the numerical computation of waves", Advances in Engineering Software, 1997, pp. 417-424, vol. 28.
M. E. Johnson et al., "Changes in the tear film and ocular surface from dry eye syndrome", Progress in Retinal and Eye Research, 2004, pp. 449-474, vol. 23.
F. A. Jolesz, "MRI-guided focused ultrasound surgery", Annu. Rev. Med., 2009, pp. 417-430, vol. 60.
B.F. Jones et al., "Digital infrared thermal imaging of human skin", IEEE Engineering in Medicine and Biology, 2002, pp. 41-48.
F. T. Fraunfelder et al., "The role of medications in causing dry eye", Journal of Ophthalmology, 2012, Article ID 285851, 8 pgs.
M. Kaido et al., "Concept of functional visual acuity and its applications", Cornea, 2007, pp. S29-S35, vol. 26, Suppl. 1.
P.A. Asbell, "Increasing importance of dry eye syndrome . . . artificial tear: consensus views . . . roundtable discussion", Cur Med Res Opin, 2006, pp. 2149-2157, 22(11).
D.R. Bacon and A. Shaw, "Experimental validation of predicted temperature rises in tissue-mimicking materials", Phys. Med. Biol., 1993, pp. 1647-1659, vol. 38.
J.C. Bamber, "Attenuation and Absorption", Physical Principles of Medical Ultrasonics, 2004, pp. 93-166.
S.B. Barnett et al., "International recommendations and guidelines for the safe use of diagnostic ultrasound in medicine", Ultrasound in Med & Biol, 2000, pp. 355-366, 26(3).
S. B. Barnett et al., "The sensitivity of biological tissue to ultrasound", Ultrasound in Med. & Biol., 1997, pp. 805-812, 23(6).
C. A. Blackie et al., "Inner eyelid surface temperature as a function of warm compress methodology", Optometry and Vision Science, 2008, pp. 675-683, 85(8).
C. A. Blackie et al., "Nonobvious Obstructive Meibomian Gland Dysfunction", Optometry and Vision Science, 2010, pp. 1333-1345, 29(12).
C. A. Blackie et al., "Warm compresses anf the risks of elevated corneal temperature with massage", Cornea Journal, 2013, pp. 1-4, 0(0).
D. Borchman et al., "Confirmation of changes in human meibum . . . with age using principal component analysis", Current Eye Research, 2010, pp. 778-786, 35(9).
D. Borchman et al., "Human meibum lipid conformation and thermodynamic changes with meibomian-gland dysfunction", IOVS, 2011, pp. 3805-3817, 52(6).
M.K.J. Klamann et al., "Measurement of dynamic ocular surface temperature in healthy subjects using a new thermography device", Current Eye Research, 2012, pp. 678-683, 37(8).
J. Kampmeier et al., "Thermal and biomechanical parameters of porcine cornea", Cornea, 2000, pp. 355-363, 19(3).
S. Karki et al., "A lumped-parameter transducer model for piezoelectric and ferroelectret polymers", Measurement, 2012, pp. 453-458, vol. 45.
Y. Kim et al., "High-intensity focused ultrasound therapy: an overview for radiologists", Korean J Radiol, 2008, pp. 291-302, vol. 9(4).
M. C. Kolios et al., "Blood flow cooling and ultrasonic lesion formation", Med. Phys., 1996, pp. 1287-1298, 23(7).
D. R. Korb et al, "Restoration of meibomian gland functionality with novel thermodynamic treatment device—a case report", Cornea, 2010, pp. 930-933, 29(8).
C.L. De Korte et al., "Acoustic velocity and attenuation of eye tissues at 20 MHz", Ultrasound in Med. & Biol., 1994, pp. 471-480, 20(5).

(56) References Cited

OTHER PUBLICATIONS

D. E. Kruse et al., "Spatial and temporal controlled tissue heating on a modified clinical ultrasound scanner . . . in tumors", IEEE Ultrasounics Symposium, 2007, pp. 313-318.
A. K. C. Lam et al., "Effect of warm compress therapy from hard-boiled eggs on corneal shape", Cornea, 2007, pp. 163-167, 26(2).
S. S. Lane et al., "A new system, the lipiflow, for the treatment of meibomian gland dysfunction", Cornea, 2012, pp. 396-404, 31(4).
M. A. Lemp, "Report of the national eye institute/industry workshop on clinical trials in dry eyes", the CLAO Journal, 1995, pp. 221-232, 21(4).
K. Liu et al., "Finite propagation of heat transfer in a multilayer tissue", Journal of Thermophysics and Heat Transfer, 2008, pp. 775-782, 22(4).
J. Liu et al., "Ultrasonic model and system for measurement of corneal . . . properties and validation on phantoms", Journal of Biomechanics, 2007, pp. 1177-1182, vol. 40.
F.L. Lizzi et al., "Ocular tumor treatments with focused ultrasound: effects of beam geometry . . . adjacent tissues", IEEE Ultrasonics Symposium, 2000, pp. 1299-1301.
E. L. Madsen et al., "Liquid or solid ultrasonically tissue-mimicking materials with very low scatter", Ultrasound in Med. & Biol., 1998, pp. 535-542, 24(4).
E. L. Madsen et al., "Tissue mimicking materials for ultrasound phantoms", Med. Phys., 1978, pp. 391-394, 5(5).
S. Mahjoob et al., "Analysis of bioheat transport through a dual layer biological media", Journal of Heat Transfer, 2010, pp. 031101 1-031101 14, vol. 132.
G. E. Mannor et al., "Laser doppler perfusion imaging of eyelid skin", Ophthalmic Plastic and Reconstructive Surgery, 1996, pp. 178-185, 12(3).
C. J. Martin et al., "Design of thermistor probes for measurement of ultrasound intensity distributions", Ultrasonics, 1983, pp. 85-90.
E. Martin et al., "Noninvasive treatment for brain tumors: magnetic resonance-guided focused ultrasound surgery", Tumors of the Central Nervous System, pp. 227-236, vol. 3.
S. L. Maskin, "Intraductal meibomian gland probing relieves symptoms of obstructive meibomian gland dysfunction", Cornea, 2010, pp. 1145-1152, 29(10).
T. D. Mast, "Empirical relationships between acoustic parameters in human soft tissues", Acoustics Research Letters Online, 2000, pp. 37-42, 1(2).
"Partial differential equation toolbox user's guide", The MathWorks, Inc., 1984-1997, Chapters 1-5.
Y. Matsumoto et al., "Efficacy of a new warm moist air device on tear functions of patients with simple meibomian gland dysfunction", Cornea, 2006, pp. 644-650, 25(6).
M. McDonald et al., "Multi-modality tissue-mimicking phantom for thermal therapy", Phys. Med. Biol., 2004, pp. 2767-2778, vol. 49.
S. McGinnigle et al., "Evaluation of dry eye", Survey of Ophthalmology, 2012, pp. 293-316, 57(4).
C. W. McMonnies et al., "The role of heat in rubbing and massage-related corneal deformation", Contact Lens & Anterior Eye, 2012, pp. 148-154, vol. 35.
P. M. Meaney et al., "A 3-D finite-element model for computation of temperature profiles . . . sugery exposures", Ultrasound in Med. & Biol.,1998, pp. 1489-1499, 24(9).
R. Mencucci et al., "Ultrasound thermal damage to rabbit corneas after simulated phacoemulsification", J Cataract Refract Surg, 2005, pp. 2180-2186, vol. 31.
A.J. Milligan et al., "Preditions of blood flow from thermal clearance during regional hyperthermia", Int. J. Radiation Oncology Biol. Phys., 1983, pp. 1335-1343, vol. 9.
J. A. Scott, "A finite element model of heat transport in the human eye", Phys. Med. Biol., 1988, pp. 227-241, 33(2).
A. Shaw et al., "Proposed standard thermal test object for medical ultrasound", Ultrasound in Med. & Biol., 1999, pp. 121-132, 25(1).

R. K. Shrestha et al., "Analysis of the composition of lipid in human meiburn . . . $^1$H-NMR Spectroscopy", Investigative Ophthalmology & Visual Science, 2011, pp. 7350-7358, 52(10).
J. D. Solomon et al., "Warm compress induced visual degradation and fischer-schweitzer polygonal reflex", Optometry and Vision Science, 2007, pp. 580-587, 84(7).
A. F. W. Van Der Steen et al., "Ultrasonic spectroscopy of the porcine eye lens", Ultrasound in Med. & Biol., 1994, pp. 967-974, 20(9).
M. Stucker et al, Capillary blood cell velocity in human skin capillaries . . . measured by a new laser doppler anemometer, Microvascular Research, 1996, pp. 188-192, vol. 52.
X. Su et al., "Density of ocular components of the bovine eye", Optometry and Vision Science, 2009, pp. 1187-1195, 86(10).
M. M. Swindle et al., "Swine as models in biomedical research and toxicology testing" Veterinary Pathology, 2012, pp. 344-356, 49(2).
L. Tafra et al., "Ablative therapies", F.M. Dirbas and C.E.H.Scott-Conner (eds.), Breast Surgical Techniques and Interdisciplinary Management, 2011, pp. 391-407, vol. 34.
A. Villamarin et al., "3D simulation of the aqueous flow in the human eye", Medical Engineering & Physics, 2012, pp. 1462-1470, vol. 34.
M. L. Cohen, "Measurement of the Thermal Properties of Human Skin. A Review", The Journal of Investigative Dermatology, 1977, pp. 333-338, 69(3).
"Focused ultrasound induced heating in tissue phantom", Solved with COMSOL Multiphysics 4.4, 38 pgs.
"Piezoacoustic Transducer", Solved with COMSOL Multiphysics 4.4, 12 pgs.
M.G. Cooper et al., "Thermal contact conductance", Int. J. Heat Mass Transfer, 1969, pp. 279-300, vol. 12.
A. Couppis et al., "Heart ablation using a planar rectangle high intensity ultrasound transducer and MRI guidance", Ultrasonics, 2012, pp. 821-829, vol. 52.
M. O. Culjat et al., "A review of tissue substitutes for ultrasound imaging", Ultrasound in Med. & Biol., 2010, pp. 861-873, 36(6).
C. M. Modulo et al., "The role of dyslipidemia on ocular surface, lacrimal and meibomian gland structure and function", Current Eye Research, 2012, pp. 300-308, 37(4).
C.M. Moran et al., "Ultrasonic propagation properties of excised human skin", Ultrasound in Med. & Biol., 1995, pp. 1177-1190, 21(9).
P. B. Morgan et al., "Infrared thermography of the tear film in dry eye", Eye, 1995, pp. 615-618, vol. 9.
A.R. Moritz et al., "The relative importance of time and surface temperature in the causation of cutaneous burns", Studies of Thermal Injury, 1946, pp. 695-720.
A. Nagymihalyi et al., "The influence of eyelid temperature on the delivery of meibomian oil", Expeirmental Eye Research, 2004, pp. 367-370, vol. 78.
V. Nahirnyak et al., "Ultrasound-induced thermal elevation in clotted blood and cranial bone", Ultrasound in Med. & Biol., 2007, pp. 1285-1295, 33(8).
T. L. Naoumidi et al., "Conductive Keratoplasty: Histological Study of Human Corneas", American Journal of Ophthalmology, 2005, pp. 984-992, 140(6).
K. K. Nichols et al., "The international workshop on meibomian gland dysfunction: executive summary", IOVS, 2011, pp. 1922-1929, 52(4).
M. W. Nygren, "Finite Element Modeling of Piezoelectric Ultrasonic Transducers", Norwegian Univesity of Science and Technology, 2011.
M.C. Olson et al., "Increase in tear film lipid layer thickness . . . in patients with meibomian gland dysfunction", Eye & Contact Lens, 2003, pp. 96-99, 29(2).
B. E. O'Neill et al., "Estimation of thermal dose from MR Thermometry . . . intensity focused ultrasound", Journal of Magnetic Resonance Imaging, 2012, pp. 1169-1178, vol. 35.
K. J. Parker, "Effects of heat conduction and sample size on ultrasonic absorption measurements", J. Acoust. Soc. Am., 1985, pp. 719-725, 77(2).

(56) References Cited

OTHER PUBLICATIONS

K. J. Parker, "The thermal pulse decay technique for measuring ultrasonic absorption coefficients", J. Acoust. Soc. Am., 1983, pp. 1356-1361, 74(5).

A. Partanen et al., "Reduction of peak acoustic pressure and shaping . . . ultrasound mediated mild hyperthermia", Medical Physics, 2013, pp. 013301 1-013301 13, 40(1).

H. Wang et al., "High frequency properties of passive materials for ultrasonic transducers", IEEE Transactions on Ultrasonics . . . Control, 2001, pp. 78-84, 48(1).

J. Tu et al., "Controllable in vivo hyperthermia effect . . . pulsed high intensity focused ultrasound with low duty cycles", Appl. Phys. Lett., 2012, pp. 124102 1- 124102 5, vol. 101.

J. Patterson et al., "The role of blood flow in hyperthermia", Int. J. Radiation Oncology Biol. Phys., 1979, pp. 235-241, 5(2).

H. H. Pennes, "Analysis of tissue and arterial blood temperatures in the resting human forearm", Journal of Applied Physiology, 1948, pp. 93-122, 1(2).

A. D. Pucker et al., "Analysis of meibum and tear lipids", The Ocular Surface, 2012, pp. 230-250, 10(4).

B. I. Raju et al., "High-frequency ultrasonic attenuation and backscatter coefficients . . . subcutaneous fat", Ultrasound in Med. & Biol., 2001, pp. 1543-1556, 27(11).

K. V. Ramnarine et al., "Contruction and geometric stability of physiological flow rate wall-less stenosis phantoms", Ultrasound in Med. & Biol., 2001, pp. 245-250, 27(2).

G. W. Recktenwald, "Finite-difference approximations to the heat equation", Mechanical Engineering Department, Portland State University, 2011, 27 pgs.

R.B. Roemer et al., "Comparative evaluation of hyperthermia heating modalities: II. Application . . . Power Range Technique", Radiation Research, 1984, pp. 473-486, 100(3).

R.B. Roemer et al., "Obtaining local SAR and blood perfusion data . . . transient techniques compared", Int. J. Radiation Oncology Biol. Phys., 1985, pp. 1539-1550, 11(8).

W. Rudin, "Principles of mathematical analysis", Third Edition, 1976, 342 pages.

J. A. Sanchis-Gimeno et al., "Differences in ocular dimensions between normal and dry eyes", Surg Radiol Anat, 2006, pp. 267-270, vol. 28.

S. Wang et al., "Optimization of pulsed focused ultrasound exposures for hyperthermia applications", J. Acoust. Soc. Am., 2011, pp. 599-609, 130(1).

F. M. Waterman et al., "Blood flow in human tumors during local hyperthermia", Int. J. Radiation Oncology Biol. Phys., 1991, pp. 1255-1262, 20(6).

C. Wei-Cheng et al., "In vivo hyperthermia effect induced by high-intensity pulsed ultrasound", Chin. Phys. B., 2012, pp. 074301 1-074301 7, 21(7).

C. J. Wolfkiel et al., "Measurement of myocardial blood flow by ultrafast computed tomography" Circulation, 1987, pp. 1262-1273, vol. 76.

Y. Zhou, "Generation of uniform lesions in high intensity focused ultrasound ablation", Ultrasonics, 2013, pp. 495-505, vol. 53.

L. Zhu et al., "Simultaneous measurements of local tissue temperature . . . during radio frequency thermal therapy", Biomechan Model Mechanobiol, 2005, pp. 1-9, vol. 4.

Bilaniuk and Wong, "Underwater acoustics technical guides—speed of sound in pure water", National Physical Laboratory, 2000, pp. 1-5.

USPTO, Office Action for U.S. Appl. No. 14/543,215 dated Aug. 17, 2015.

USPTO, Office Action for U.S. Appl. No. 14/543,215 dated Feb. 1, 2016.

USPTO, Office Action for U.S. Appl. No. 14/543,215 dated Nov. 18, 2016.

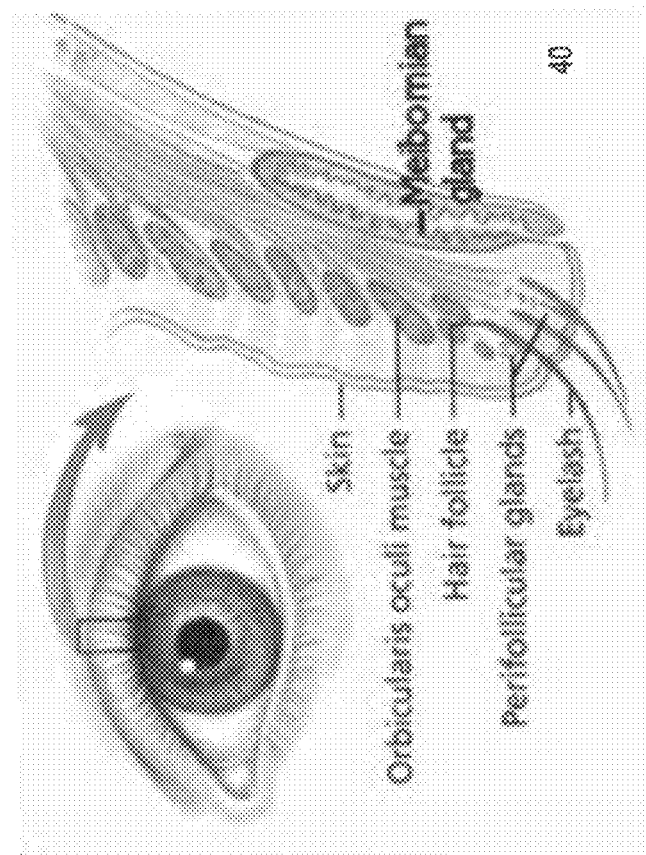
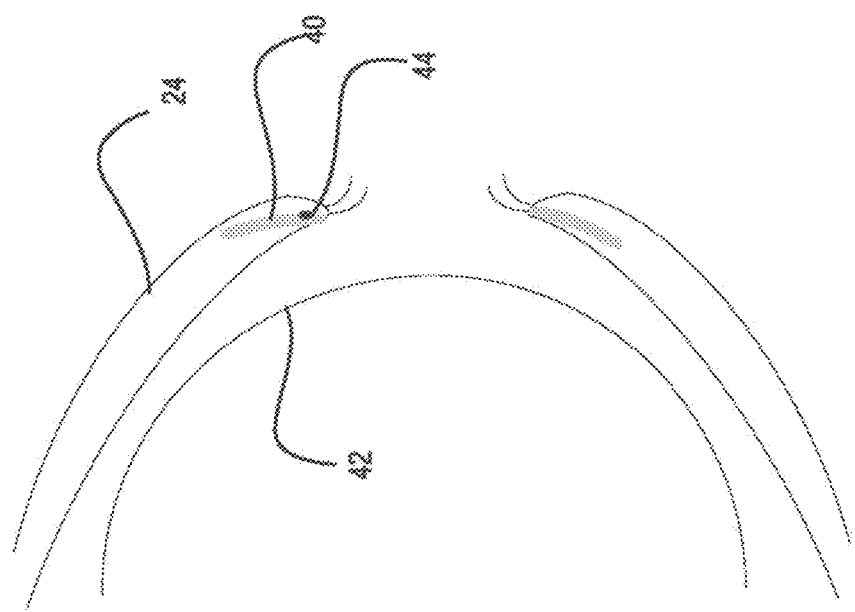
FIGURE 2

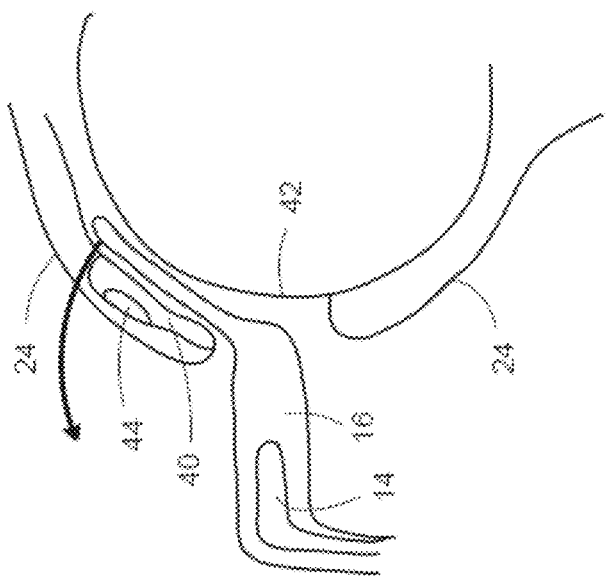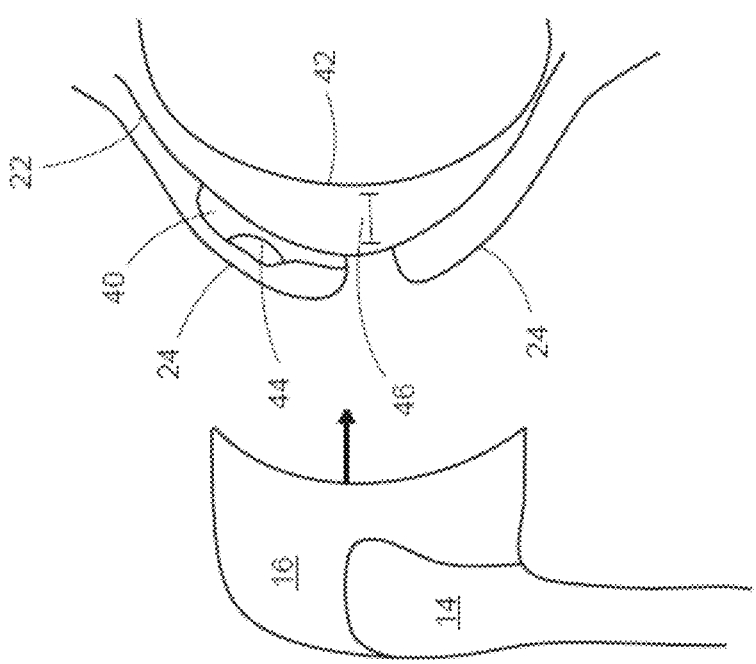
Figure 3

(A) A small transducer with minimal epoxy, fitted inside a lens
(B) A large transducer epoxied to a lens with its tip removed

METHOD, SYSTEM AND USE FOR THERAPEUTIC ULTRASOUND

FIELD

The described embodiments relate to methods, systems and uses for therapeutic ultrasound, and in particular, to methods, systems and uses for therapeutic ultrasound for treating or alleviating eye conditions.

INTRODUCTION

Eye conditions may relate to meibomian gland dysfunction. Dry eye is a multifactorial disease of epidemic proportions. Dry eye may be caused by meibomian gland dysfunction. Dry eye can be categorized into two broad categories: aqueous deficient dry eye and evaporative dry eye. Wth blockage of the eyelid meibomian glands and ducts there may be a reduction of lipids within the tear film. This results in instability of the tear film with subsequent early tear break up and evaporation. This ultimately leads to exposure of the corneal surface and a cascade of ocular surface inflammation, thus perpetuating a dysfunctional tear syndrome.

Another example eye condition is a chalazion or meibomian cyst which is a collection of oil or blockage of the meibomian gland and ducts. A further example of an eye condition is a hordeolum or stye which may be an inflamed sebaceous gland of Zeiss. Finally, an additional example is blepharitis which is an inflammation of the eyelid which may predispose subjects to aforementioned eye conditions, such as dry eye, chalazion, hordeolum. Other eye conditions include scarring.

There is a need for improved methods, systems and uses for treating or alleviating eye conditions, such as those associated with the meibomian gland and ducts, or at least alternatives.

SUMMARY

In a first aspect, embodiments described herein relate to an ultrasound device and air gap lens for treatment of an eye condition.

Embodiments may include a contact lens with internal air chamber and the transducer may be applied externally through the eyelid. This may enable a longer transducer length to cover the entire length of the meibomian glands. The external transducer may also be able to move along the entire length of the meibomian glands.

The internal air gap and lens may impede ultrasound gel or water getting into the air gap. Ultrasound gel may get under the contact lens and irritate the eye.

The shape of the contact lens may vary, and in some example embodiments may be elliptical to maximize the number of meibomian glands treated across the full horizontal length of the eyelid.

In some embodiments, drug delivery (e.g. steroid) may be facilitated by the ultrasound use. This may be referred to as phonophoresis.

In some embodiments, an imaging device may be used or a dual transducer could treat and image. The imaging and processing may quantify the amount of meibum in the glands and ductules. Post treatment imaging may show a reduction of meibum in the glands thus confirming that the oil was expressed.

The device may include at least one ultrasound transducer for supplying ultrasound waves to an area proximate to the portion of the eyelid according to treatment parameters. The ultrasound transducer may provide therapeutic ultrasound generally across the frequency range 0.2 to 10 MHz according to some embodiments. In other embodiments the frequency range may extend as high as 50 MHz One example mechanism for therapeutic gain may be differential absorption of ultrasound in fats compared to non-fatty tissues. This increases with increasing frequency which may support a higher frequency range.

These illustrative frequency ranges are not intended to restrict. Therapeutic Ultrasound may be generally applied across various frequency ranges.

The air gap lens may be used to protect ocular tissue around the eye. The lens may be a vaulted scleral contact lens configured for placement over the eye globe and under the eyelid. The lens may have two layers or may comprise two lenses configured to form a chamber of air between the layers or lenses. The chamber of air may protect the cornea and may block penetration of ocular tissue by the ultrasound waves.

The closed air chamber within the lens structure may ensure that there is always a built-in air barrier to ultrasound which may provide sufficient acoustic impedance. Wth such a design ultrasound contact gel can be used on the surface of the eyelid or periocular tissue without concern of the gel or any other fluid getting into the air barrier. As ultrasound does not propagate well through gases this design would provide high acoustic impedance and thus shield the eye from ultrasound energy. The different layers of the lens may also comprise an absorptive material to block penetration of ocular tissue by the ultrasound waves. In particular, if the ultrasound is being applied externally through a separate ultrasound probe, then outer surface of the contact lens which abuts the tarsal conjunctiva of the eyelid could be made of an absorptive material or have an absorptive coating hat would uniformly heat and further act to warm the inner eyelid and the meibomian glands.

The lens could be circular. Alternatively it could be an elliptical shape to conform to the full horizontal length of the tarsal plate within which the meibomian glands are situated. Similarly the PZT transducer whether built into the contact lens or applied externally through a separate probe could be an elliptical shape or other similar shape which would allow simultaneous irradiation of the maximum number of meibomian glands in both the upper and lower eyelids.

In some embodiments, the system may further comprise a lens speculum to elevate the eyelid from the eye globe and create airspace between eye globe and eyelid.

In some embodiments, the system may further comprise a temperature measurement mechanism for measuring the temperature of the area proximate to the portion of the eyelid. In some embodiments, the temperature measurement mechanism may comprise a thermal couple or other comparable thermal measuring device. In some embodiments, the thermal couple may be positioned on the contact lens. In some embodiments, the system may further comprise an ultrasound measurement mechanism for measuring the ultrasounds waves at the area proximate to the portion of the eyelid.

In some embodiments, the treatment parameters comprise a frequency, amplitude, on/off cycle, and a treatment period. In some embodiments, the treatment frequency is at least 2 MHz, at least 3 MHz, or between 3 to 5 MHz, or higher than 5 MHz The treatment frequency may range 0.2 to 10 MHz according to some embodiments. In other embodiments the frequency range may extend as high as 50 MHz. One example mechanism for therapeutic gain may be differential absorption of ultrasound in fats compared to non-fatty tissues. This increases with increasing frequency which may support a higher frequency range. In some embodiments, the treatment period is between two to five minutes. The treatment time could however be increased to 10 to 15 minutes if a more gradual and prolonged heating was desired. These are non-limiting examples.

The on/off cycle may be used to pulse the ultrasound waves.

In some embodiments, the device further comprises a controller operable for receiving treatment data, determining the treatment parameters based on the treatment data, and directing the ultrasound transducer according to the treatment parameters.

In some embodiments, the eye condition is caused by dysfunction of the meibomian glands and wherein the area proximate to the portion of the eyelid comprises the meibomian glands and its ductules. In some embodiments, the eye condition is caused by dysfunction of the lacrimal glands and wherein the area proximate to the portion of the eyelid comprises the lacrimal glands and ductules. In some embodiments, the eye condition is caused by dysfunction of the periocular glands and wherein the area proximate to the portion of the eyelid comprises the periocular glands and ductules. In some embodiments, the eye condition is caused by dysfunction of the nasolacrimal system and wherein the area proximate comprises the nasolacrimal system. In some embodiments, the eye condition is caused by dysfunction of the Wolfring glands and wherein the area proximate to the portion of the eyelid comprises the Wolfring glands and ductules. In some embodiments, the eye condition is caused by dysfunction of the Krause glands and wherein the area proximate to the portion of the eyelid comprises the Krause glands and ductules. In some embodiments, the eye condition is caused by dysfunction of the Zeis glands and wherein the area proximate to the portion of the eyelid comprises the Zeis glands and ductules.

In some embodiments, the eye condition is caused by lipids blocked in one or more glands of the eye and wherein the ultrasound waves heat the lipids to emulsify the lipids blocked in the glands and ductules and facilitate flow. In some embodiments, the ultrasound waves heat the lipids to approximately 40 degrees Celsius to increase flow and mobility of the lipids. This is a non-limiting example. In some embodiments, the ultrasound waves supply oscillations to move the emulsified lipids by creating bubbles in the emulsified lipids. In some embodiments, the ultrasound waves supply acoustic streaming to mobilize the emulsified lipids. In some embodiments, the ultrasound waves cause mircocavitation to mobilize the emulsified lipids. In some embodiments, the ultrasound waves stimulate circulation and lymph flow in the area proximate to the portion of the eyelid.

In some embodiments, the ultrasound waves breakdown scar tissue in the area proximate to the portion of the eyelid.

In some embodiments, the ultrasound waves supply continuous ultrasound energy. In some embodiments, the ultrasound waves supply pulsed ultrasound energy defined by on/off cycle.

In some embodiments, the device further comprises a probe for coupling to the ultrasound transducer.

In some embodiments, the device is configured to provide phased array ultrasound to vary ultrasound waves.

In some embodiments, the ultrasound transducer comprises movable components that are configured to move relative to the portion of the eyelid to vary ultrasound waves.

In some embodiments, the device comprises an ultrasound imaging camera and wherein the device is operable in a therapeutic mode to heat the area proximate to the portion of the eyelid and a diagnostic mode to image the area proximate to the portion of the eyelid using the ultrasound imaging camera. In some embodiments, the device can operate in therapeutic mode and diagnostic mode to perform real-time imaging during treatment.

In some embodiments, an imaging device may be used or a dual transducer could treat and image. The imaging and processing may quantify the amount of meibum in the glands and ductules. Post treatment imaging may show a reduction of meibum in the glands thus confirming that the oil was expressed.

In some embodiments, the ultrasound transducer has a concave shape to complement the eyelid, or the ultrasound transducer has an attachment with a concave shape to complement the eyelid. In some embodiments, the ultrasound transducer has an elliptical shape to complement the eyelid. In some embodiments, the device further comprises an attachment for the ultrasound transducer, wherein the attachment comprises a protective portion for positioning over the eye globe and under the eyelid to protect eye tissue, wherein the protective portion has a concave shape to complement the eyelid.

In some embodiments, the eye condition is selected from the group consisting of dry eye, meibomian gland dysfunction, duct dysfunction, lacrimal gland dysfunction, periocular gland dysfunction, nasolacrimal system dysfunction, post-surgical scarring, and chalazion.

In another aspect, embodiments described herein provide use of an ultrasound device configured for treatment of dry eye, wherein the device comprises at least one ultrasound transducer for coupling to at least a portion of an eyelid to supply ultrasound waves to an area proximate to the lacrimal glands to stimulate aqueous production and flow from the lacrimal glands and ducts.

In another aspect, embodiments described herein provide the use of a high frequency ultrasound device configured for treatment of dry eye, wherein the device comprises at least one ultrasound transducer for coupling to at least a portion of an eyelid to supply ultrasound waves to an area proximate to the meibomian gland to stimulate meibum production and flow from the meibomian gland and ducts.

In a further aspect, embodiments described herein provide a system for treating an eye condition comprising: an ultrasound device comprising at least one ultrasound transducer for coupling to at least a portion of an eyelid to supply ultrasound waves to an area proximate to the portion of the eyelid according to treatment parameters. In some embodiments, the treatment parameters comprise a frequency, an amplitude, on/off cycle, and a treatment period. Example frequency ranges include 0.2 to even higher than 50 MHZ, other examples may be at least 2 MHz, at least 3 MHz, and between 3 to 5 MHZ. Greater than 5 MHZ frequencies may also be used to limit depth of penetration into tissue. An example treatment period is between two to five minutes. Further example frequency ranges include 0.2 to 10 MHz according to some embodiments. In other embodiments the frequency range may extend as high as 50 MHz. One example mechanism for therapeutic gain may be differential absorption of ultrasound in fats compared to non-fatty tissues. This increases with increasing frequency which may support a higher frequency range. These are non-limiting examples.

In some embodiments, the system further comprises a controller operable for receiving treatment data from an external source, determining the treatment parameters based on the treatment data, and directing the ultrasound transducer according to the treatment parameters.

In some embodiments, the ultrasound waves heat the area proximate to the portion of the eyelid.

In some embodiments, the eye condition is caused by lipids blocked in a gland or duct of the eye and wherein the ultrasound waves heat the area proximate to the portion of the eyelid to emulsify the lipids blocked in the gland or the duct and facilitate flow. In some embodiments, the ultrasound waves heat the lipids to approximately 40 degrees Celsius or even higher. In some embodiments, the ultrasound waves supply oscillations to move the emulsified lipids by creating bubbles in the emulsified lipids. In some embodiments, the ultrasound waves supply acoustic streaming to mobilize the emulsified lipids. In some embodiments, the ultrasound waves cause mircocavitation to mobilize the emulsified lipids. In some embodiments, the ultrasound waves stimulate circulation and lymph flow in the area proximate to the portion of the eyelid. In some embodiments, the ultrasound waves breakdown scar tissue in the area proximate to the portion of the eyelid. In some embodiments, the ultrasound waves supply continuous ultrasound energy. In some embodiments, the ultrasound waves supply pulsed ultrasound energy.

In some embodiments, the device further comprises a probe for coupling to the ultrasound transducer. In some embodiments ultrasound gel can be used as a contact medium between the eyelid and the ultrasound transducer. In some embodiments, the device is configured to provide phased array ultrasound. In some embodiments, the ultrasound transducer comprises movable components that are configured to move relative to the portion of the eyelid to vary ultrasound waves. In some embodiments, the device comprises an ultrasound imaging camera and wherein the device is operable in a therapeutic mode to heat the area proximate to the portion of the eyelid using the ultrasound waves and a diagnostic mode to image the area proximate to the portion of the eyelid using the ultrasound imaging camera. In some embodiments, the ultrasound transducer has a concave shape to complement the eyelid. In some embodiments, ultrasound transducer has an elliptical shape to complement the eyelid. In some embodiments, the device further comprises an attachment for the ultrasound transducer, wherein the attachment comprises a protective portion for positioning over the eye globe and under the eyelid to protect eye tissue, wherein the protective portion has a concave shape to complement the eyelid. In some embodiments, the eye condition is selected from the group consisting of dry eye, meibomian gland dysfunction, duct dysfunction, lacrimal gland dysfunction, periocular gland dysfunction, nasolacrimal system dysfunction, post-surgical scarring, and chalazion.

In some embodiments, the system may further comprise a roller shaped to complement the eyelid and applied to the eyelid to express the emulsified lipids from the gland or the duct. In a further aspect, embodiments described herein provide a method for treating an eye condition using a therapeutic ultrasound device, the method comprising: coupling at least one ultrasound transducer to at least a portion of an eyelid; and propagating ultrasound waves to an area proximate to the portion of the eyelid using the ultrasound transducer according to treatment parameters.

In some embodiments, the treatment parameters comprise a frequency, an amplitude, on/off cycle, and a treatment period. In some embodiments, the method may further comprise placing a contact lens over the eye globe and under the eyelid to protect ocular tissue around the eye. In some embodiments, the lens is a vaulted scleral contact lens configured to form a chamber of air. The chamber of air may be between lens layers of different radii of curvature or it may be behind the posterior surface of the contact lens and the cornea.

In some embodiments, the lens comprises an absorptive material to block penetration of ocular tissue by the ultrasound waves. The chamber of air may also block penetration of ocular tissue by the ultrasound waves.

In some embodiments, the method may involve using a lens speculum to elevate the eyelid from the eye globe and create an airspace between eye globe and eyelid. In some embodiments, the eye condition relates to the meibomian glands and wherein the ultrasound waves are supplied for the treatment period to liquefy solidified fats in the meibomian glands. In some embodiments, the eye condition relates to the glands of Zeiss with a hordeolum present and wherein the ultrasound waves are supplied for the treatment period to liquefy fats in the glands of Zeiss when the hordeolum is present.

In some embodiments, the method may further comprise applying ultrasound gel to the surface of the eyelid to act as a coupling medium between eye tissue and the transducer.

In another aspect, embodiments described herein provide use of an ultrasound device configured for treatment of meibomian gland dysfunction caused by solidified fats, wherein the device comprises at least one ultrasound transducer for coupling to at least a portion of an eyelid to supply ultrasound waves to the meibomian glands and ductules to heat the meibomian glands and ductules and liquefy the solidified fats.

In another aspect, embodiments described herein provide use of an ultrasound device configured to promote remodeling and resolution of eyelid scar tissue from the etiology selected from the group consisting of post-surgical, post chalazion, post-inflammatory, and post-infectious, wherein the device comprises at least one ultrasound transducer for coupling to at least a portion of the eyelid to supply ultrasound waves to breakdown scar tissue in the eyelid. This treatment could be combined with topical steroids placed directly on the dermis of the eyelid within the coupling medium. The ultrasound energy could facilitate steroid penetration into the eyelid tissue and into the periocular glands, in particular the meibomian glands. Ultrasound could be used over the eyelids or meibomian glands to promote drug delivery of other topical medications through the process of phonophoresis In a further aspect, embodiments described herein provide the use of an ultrasound device configured for treatment of an eye condition, wherein the device is operable in a therapeutic mode and a diagnostic mode, wherein the device comprises at least one ultrasound transducer for coupling to at least a portion of an eyelid to supply ultrasound waves to an area proximate to the portion of the eyelid to diagnose the eye condition in the diagnostic mode and to treat the eye condition according to treatment parameters in the therapeutic mode.

In some embodiments, the ultrasound device is configured to operate in diagnostic mode and therapeutic mode concurrently to provide real-time imaging during treatment.

In another aspect, embodiments described herein provide the use of an ultrasound device configured to facilitate fluid flow down the nasolacrimal system, wherein the device comprises at least one ultrasound transducer for coupling to at least a portion of an inner canthal region of the eye to supply ultrasound waves to an area proximate nasolacrimal system according to treatment parameters.

In another aspect, embodiments described herein provide the use of an ultrasound device configured to break up stones within the nasolacrimal system, wherein the device comprises at least one ultrasound transducer for coupling to at least a portion of an inner canthal region of the eye to supply ultrasound waves to an area proximate nasolacrimal system according to treatment parameters, wherein the treatment parameters comprise a treatment frequency and a treatment period.

DRAWINGS

For a better understanding of embodiments of the systems, methods and uses described herein, and to show more clearly how they may be carried into effect, reference will be made, by way of example, to the accompanying drawings in which:

FIG. 2 shows a diagram of a meibomian gland according to some embodiments;

FIG. 3 shows a diagram of a use of therapeutic ultrasound for eye conditions according to some embodiments;

Figure 8:
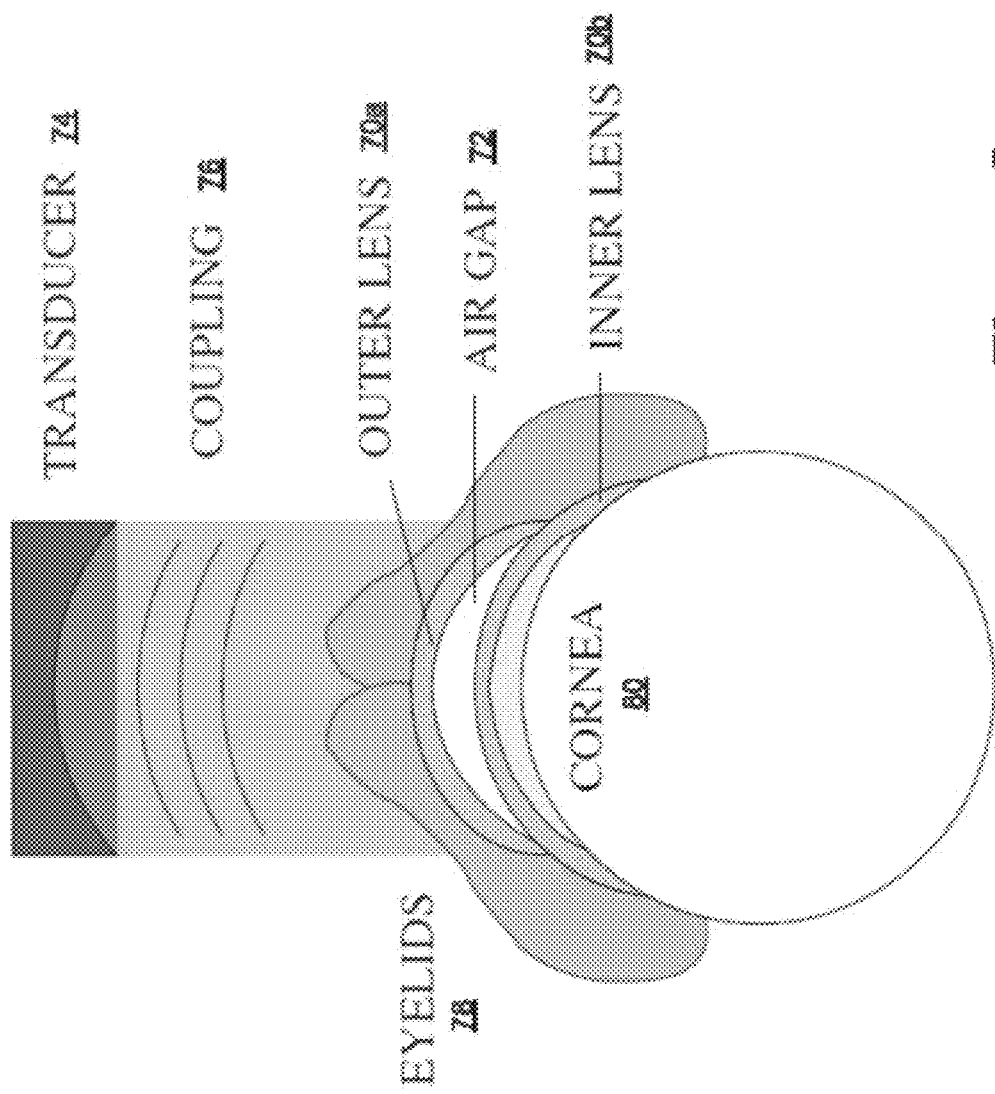

FIG. 8 an example external transducer and contact lens to protect the eye according to some embodiments.

Figure 9:
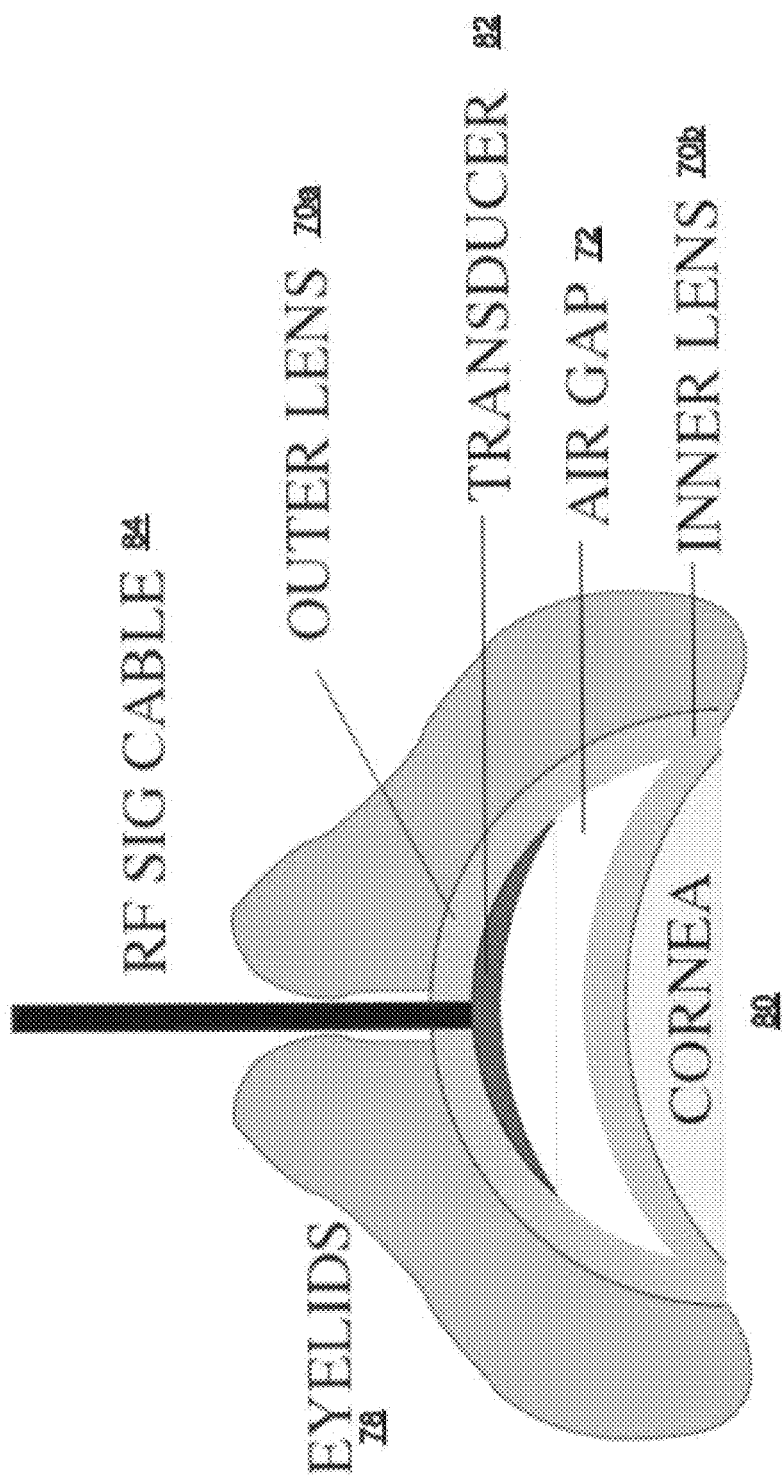

FIG. 9 shows an example internal transducer and contact lens to protect the eye according to some embodiments.

Figure 10:
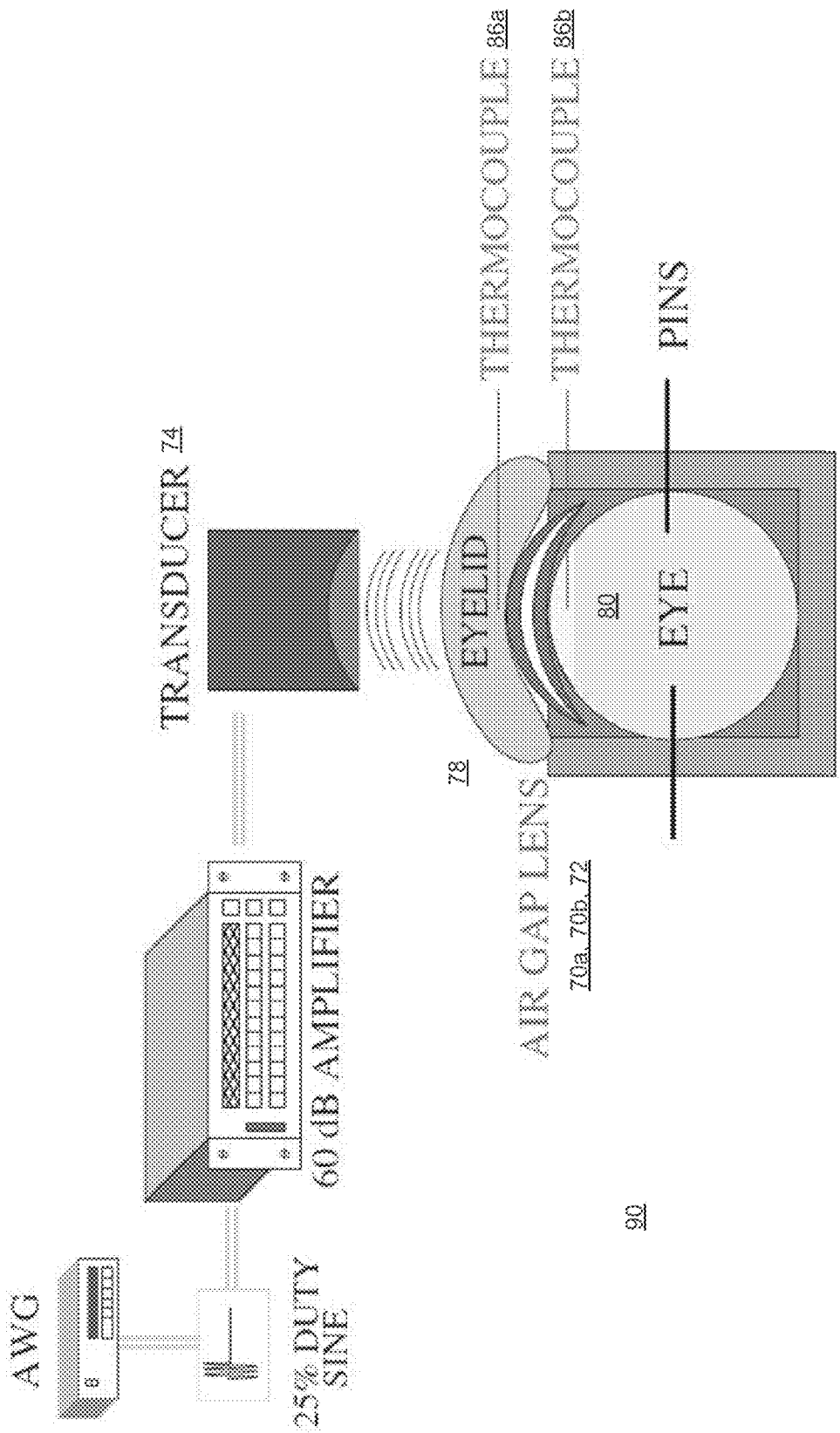

FIG. 10 an example system including a transducer and a contact lens with air gap according to some embodiments.

Figure 11:
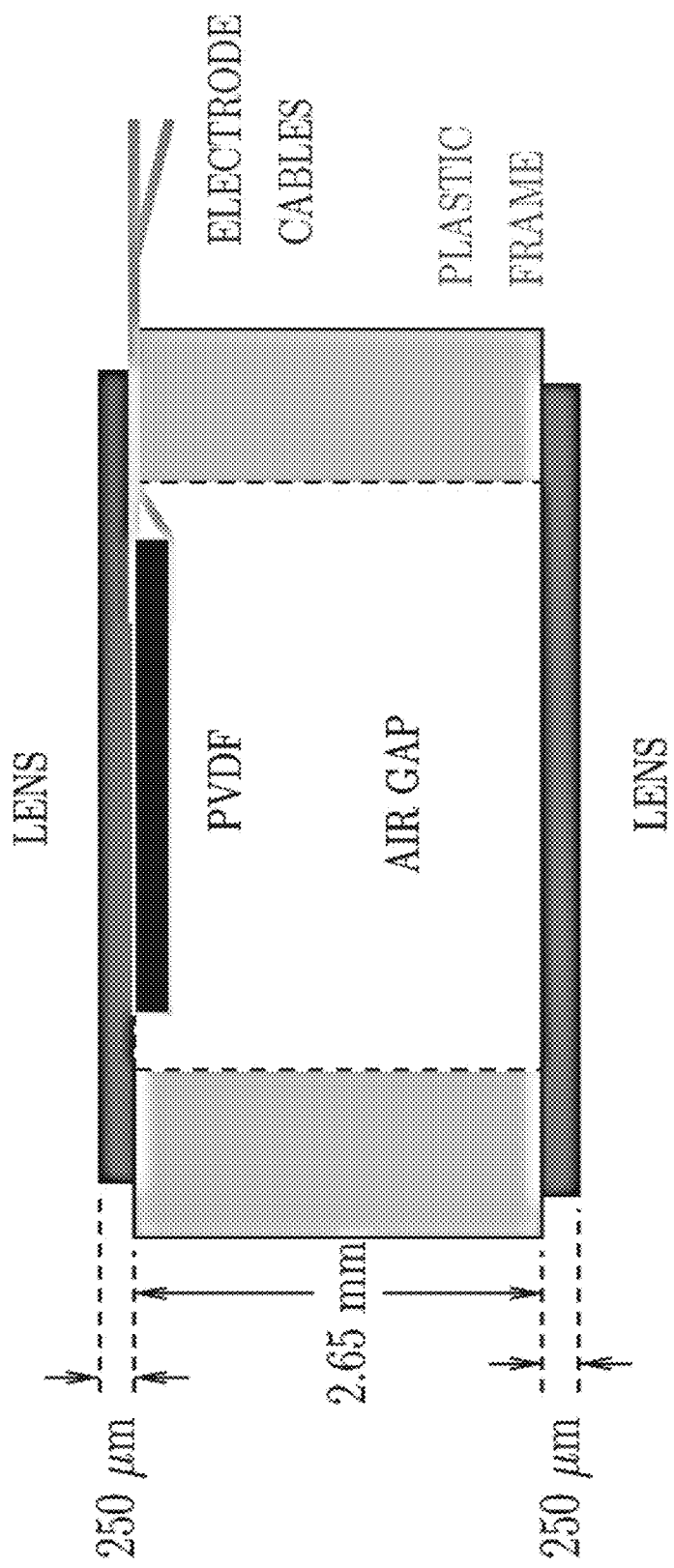

FIG. 11 an example prototype lens.

Figure 12:
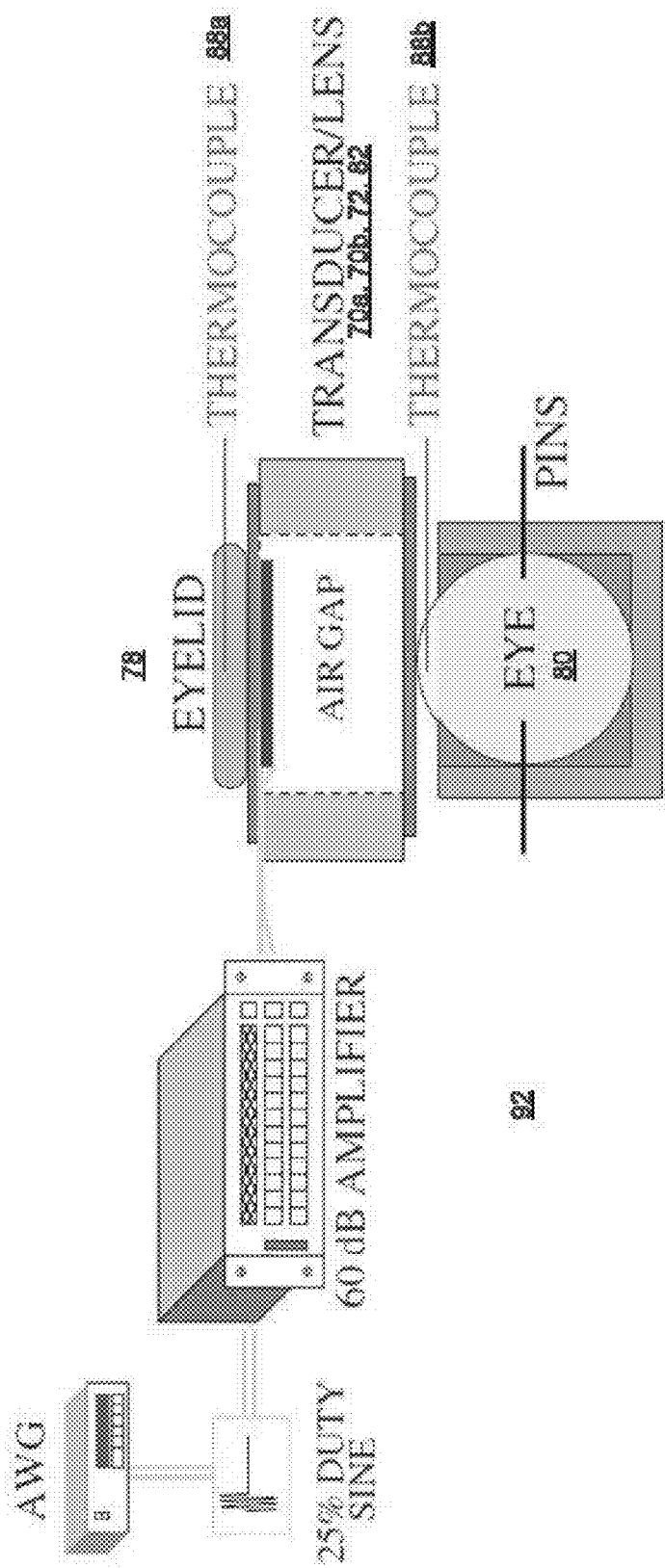

FIG. 12 another example system including a transducer and a contact lens with air gap according to some embodiments.

Figure 13:
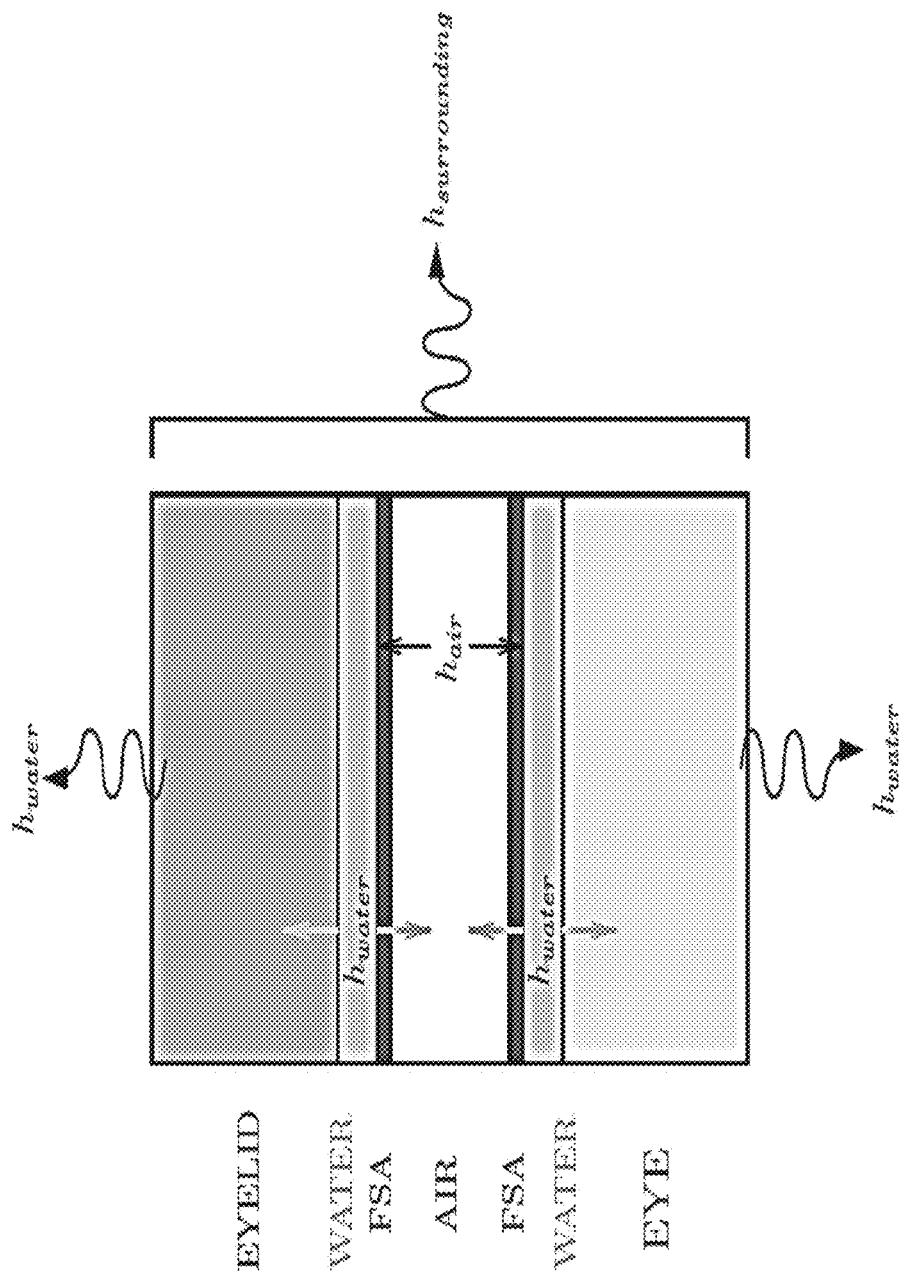

FIG. 13 illustrates an example thermal model.

Figure 14:
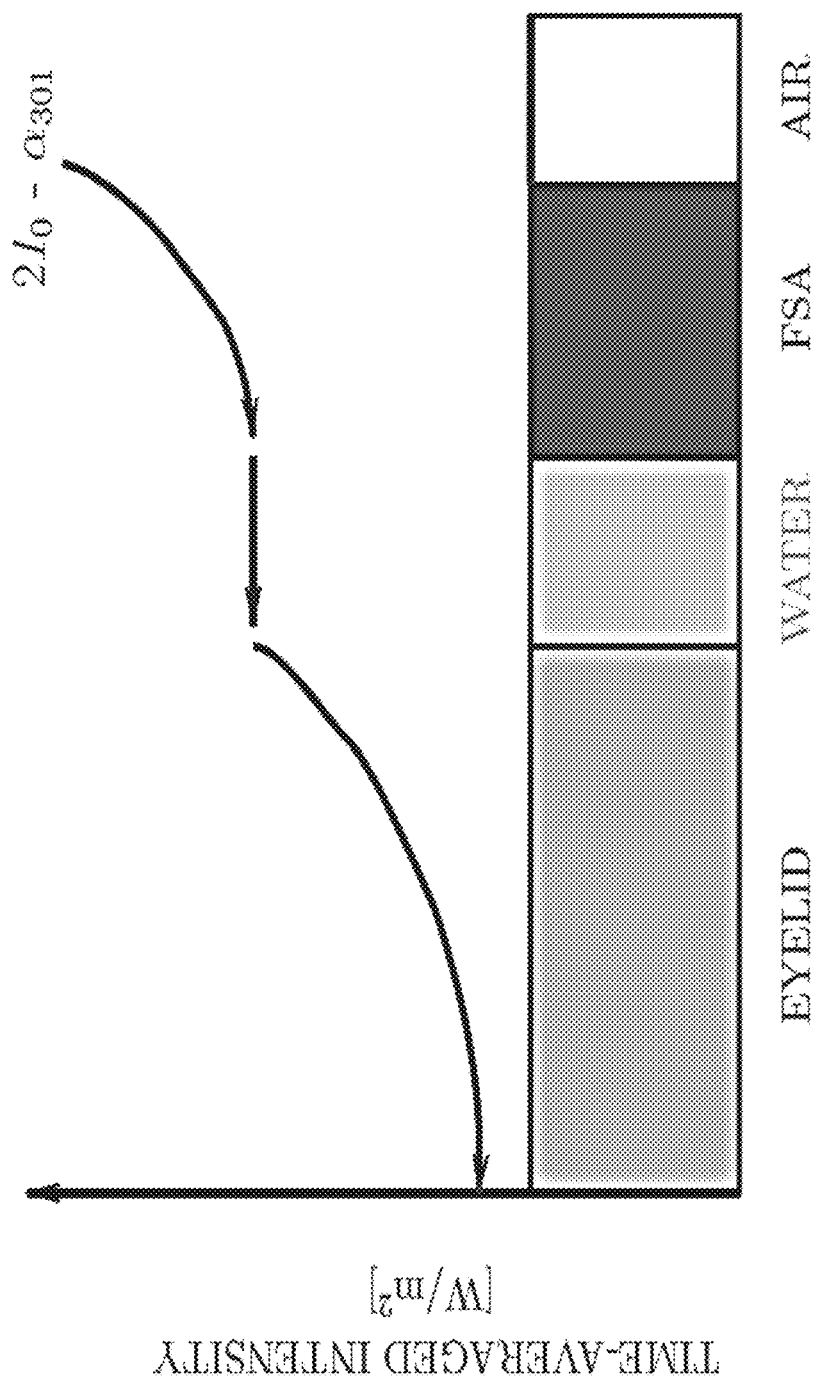

FIG. 14 illustrates an example acoustic source model.

Figure 15:
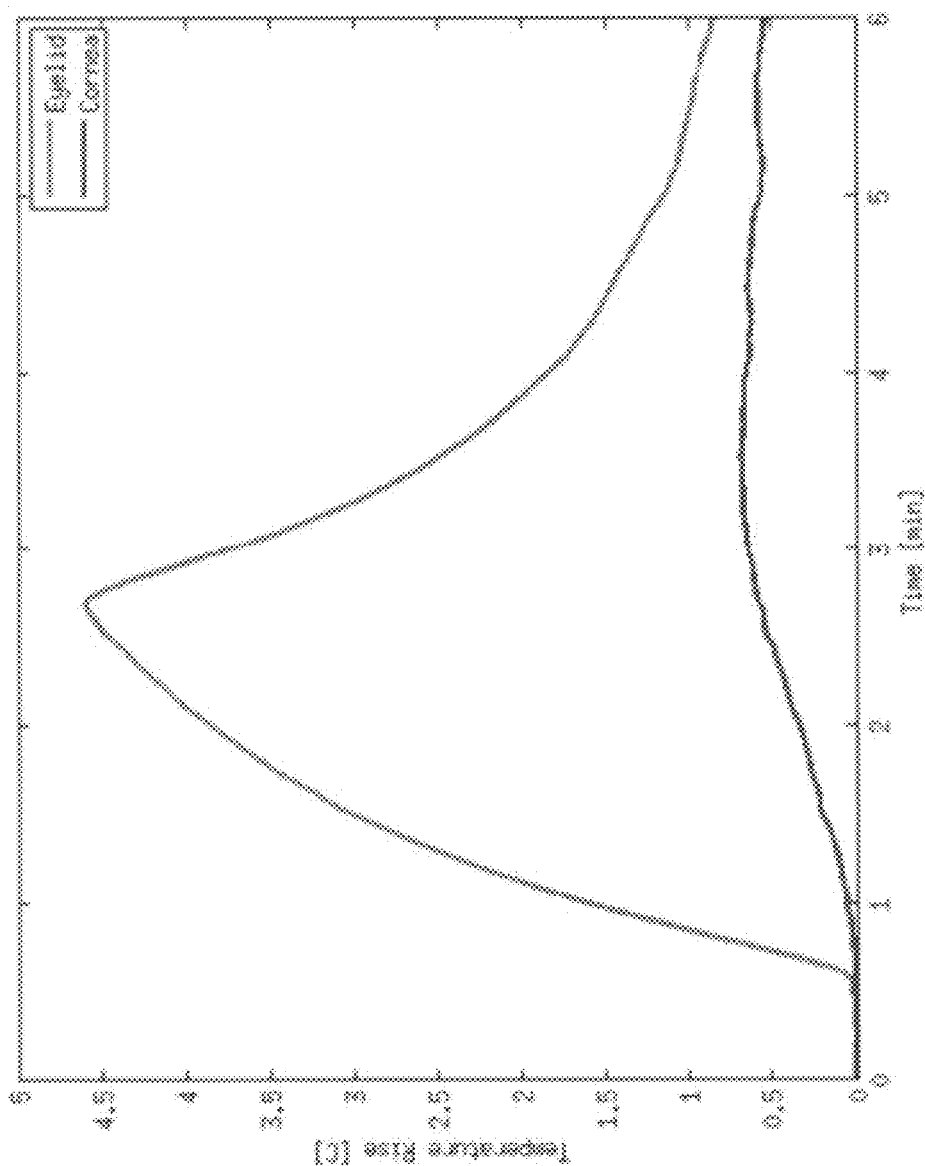

FIG. 15 illustrates a chart of temperature rise against time for the external transducer configuration.

Figure 16:
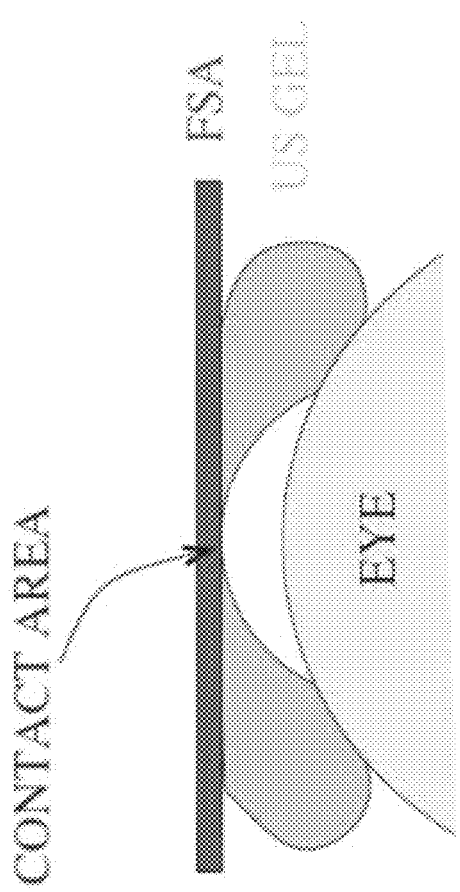

FIG. 16 illustrates a contact lens area proximate to FSA and ultrasound gel.

Figure 17:
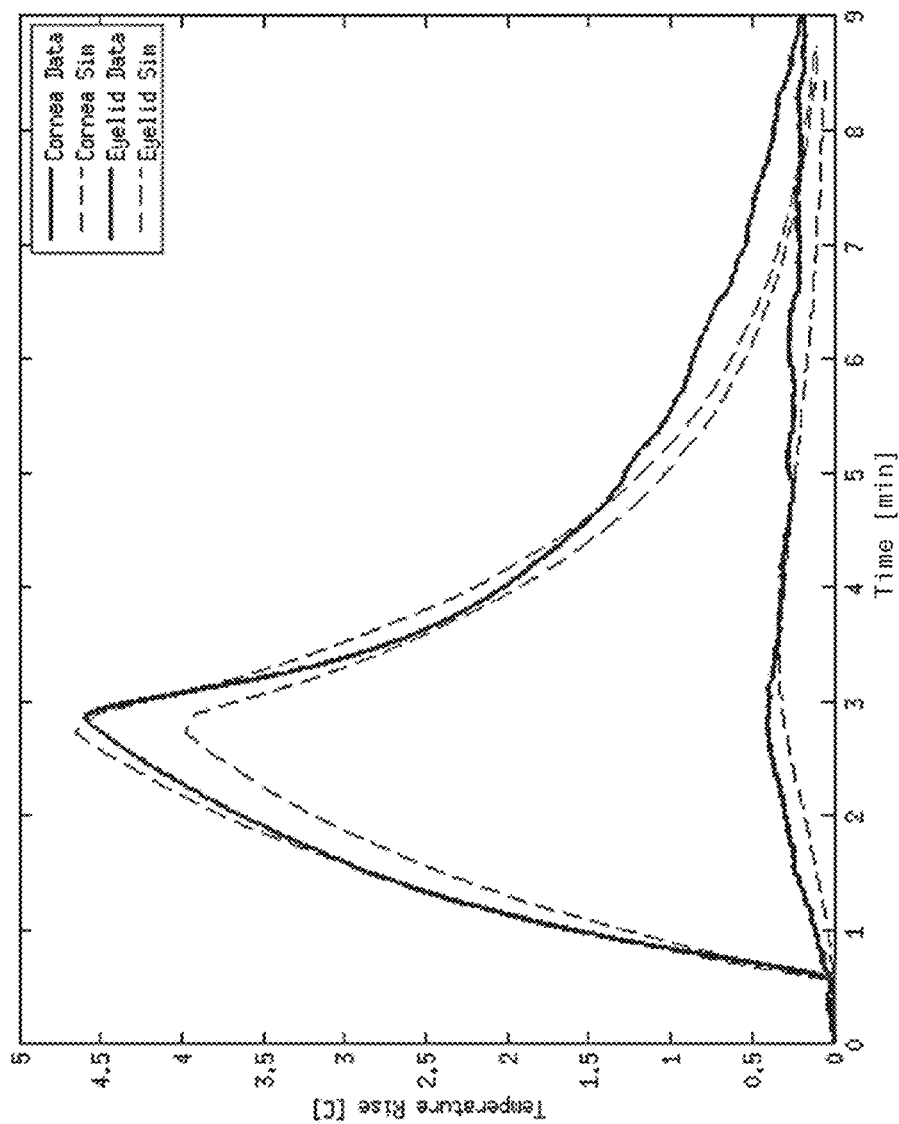

FIG. 17 illustrates a chart of temperature rise against time for FSA.

Figure 18:
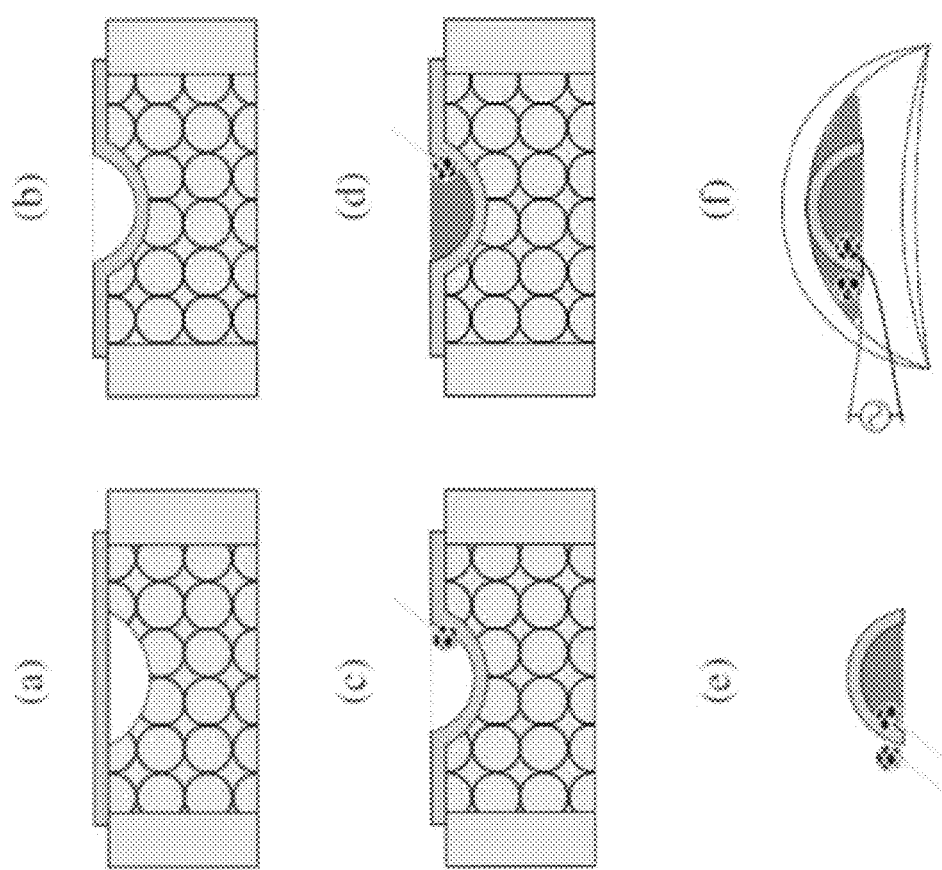

FIG. 18 illustrates example vacuum molded PVDF to construct sub-tarsal devices.

Figure 19:
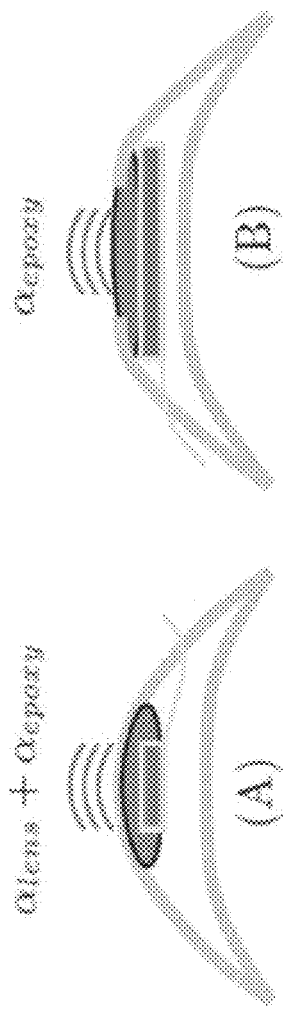

FIG. 19 illustrates example prototypes for PZT internal transducers for embedding within air gap contact lens.

Figure 20:
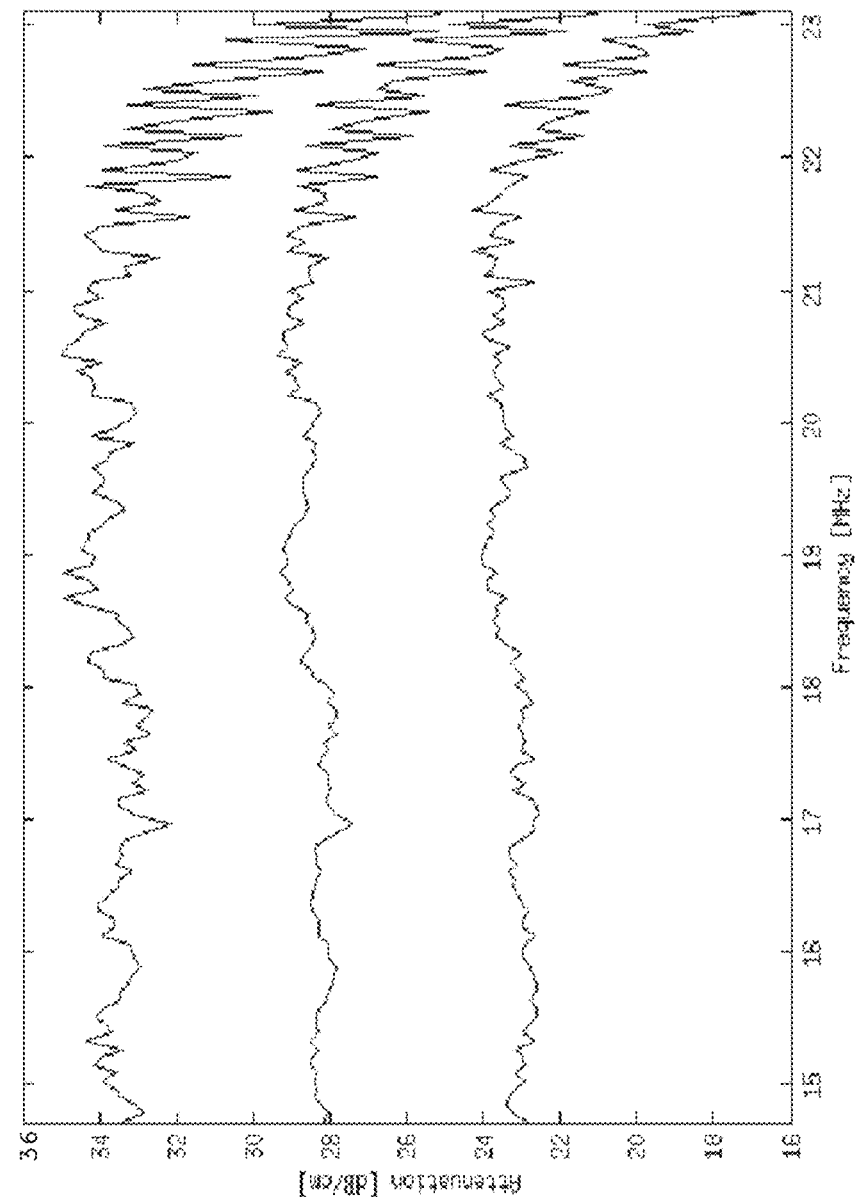
Figure 21:
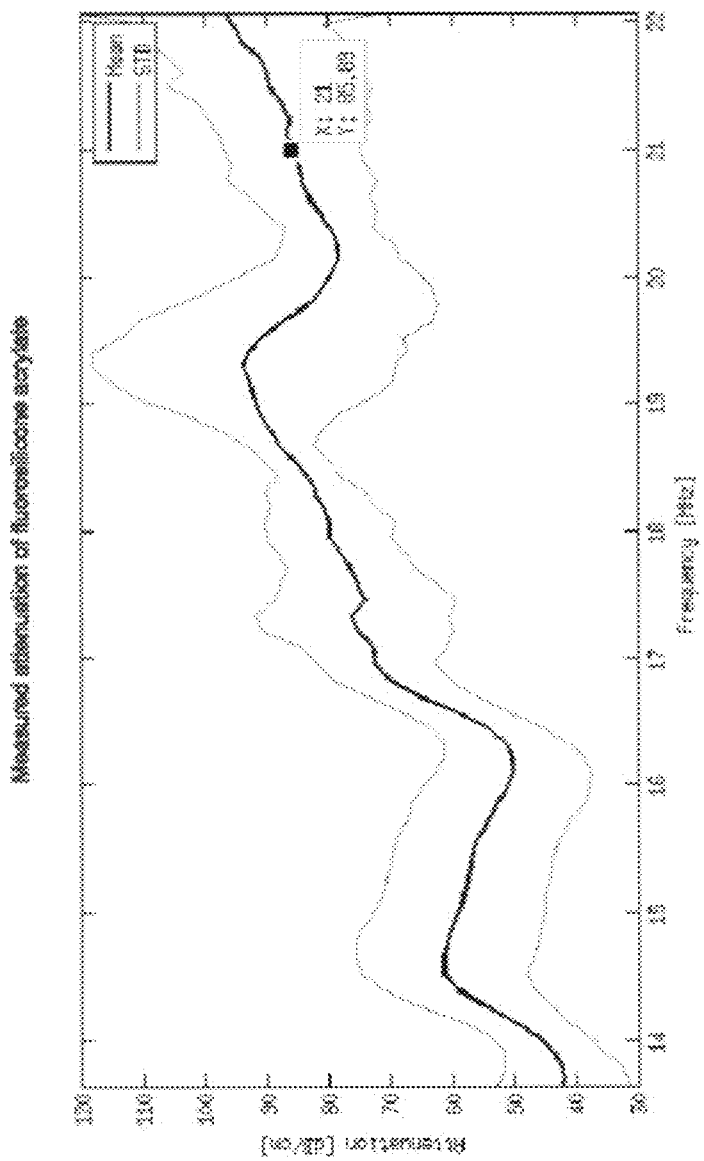

FIGS. 20 and 21 illustrate attenuation as a function of frequency.

FIGS. 22 to 25 illustrate example prototypes for PZT internal transducers for embedding within air gap contact lens.

Figure 26:
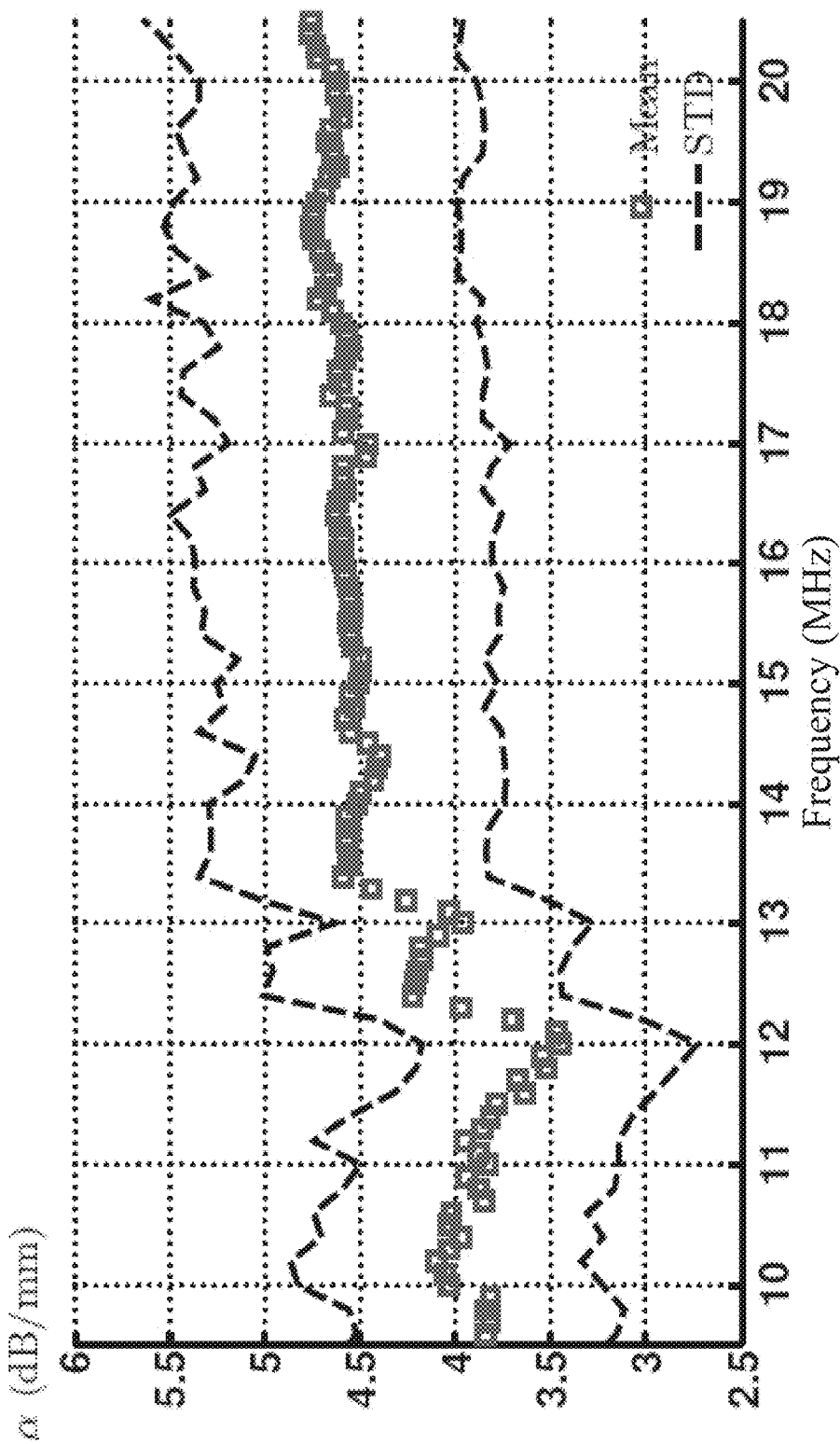

FIG. 26 illustrates a graph from measured attenuation of porcine eyelid.

Figure 27:
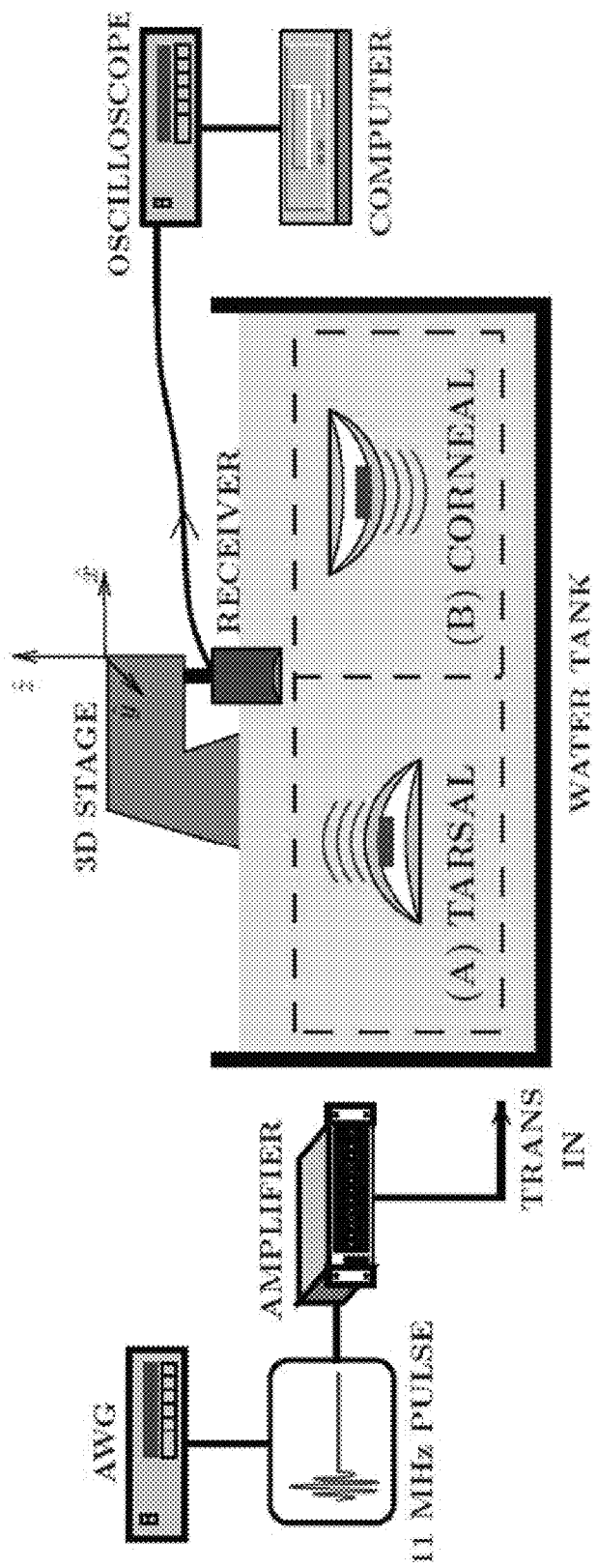
Figure 28:
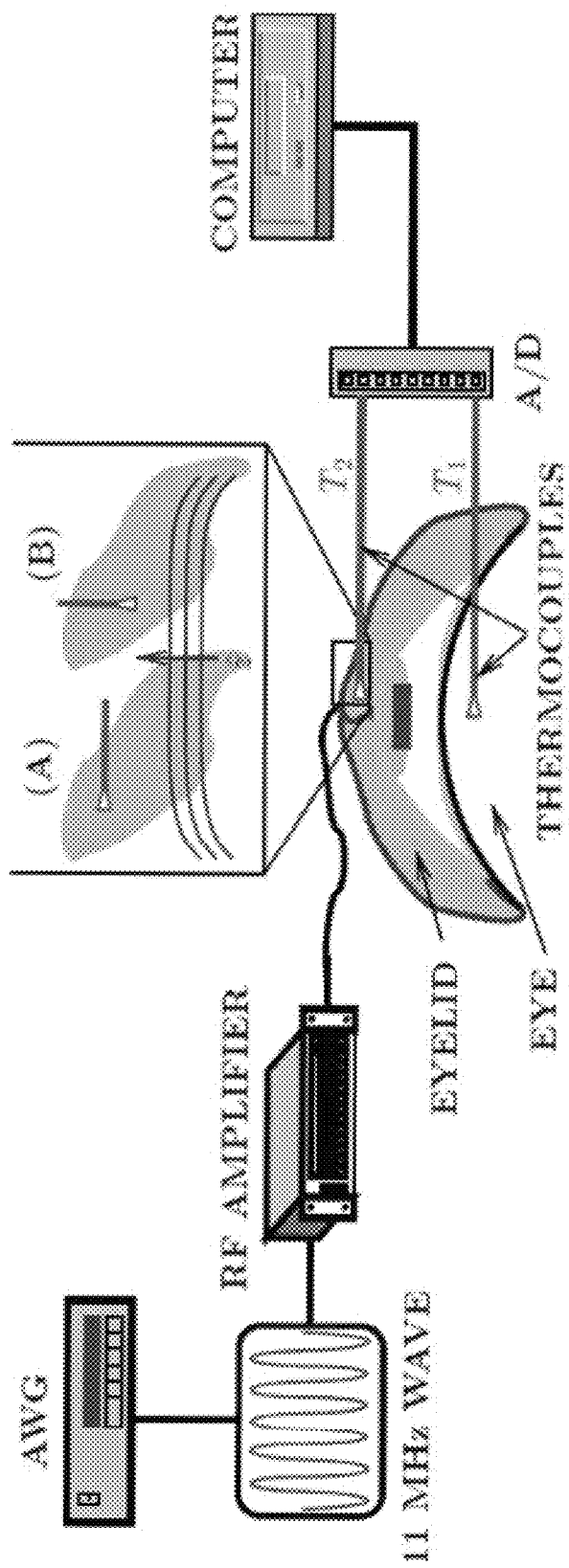

FIGS. 27 and 28 illustrate schematics of experimental embodiments.

Figure 29A:
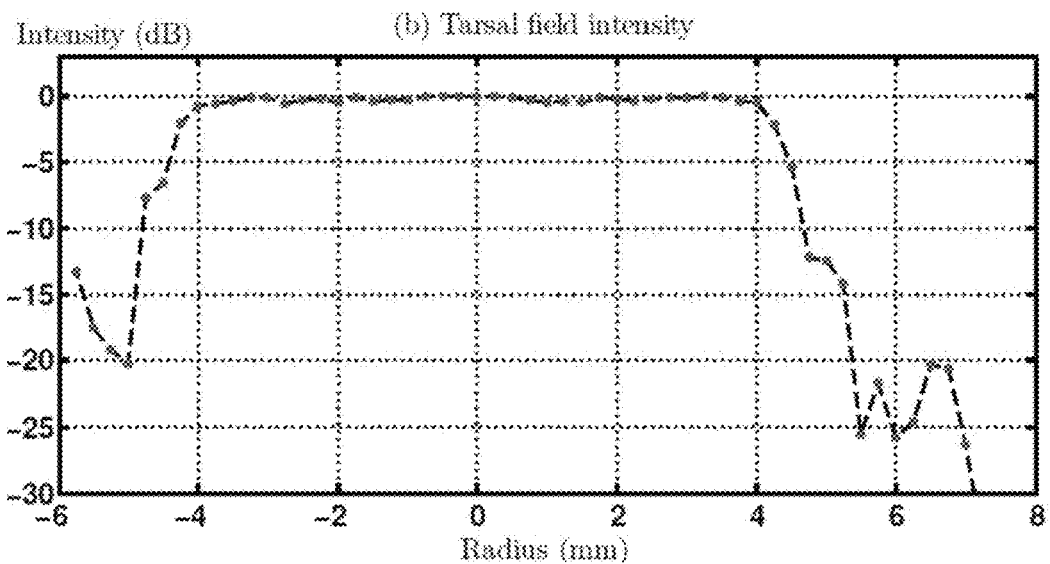
Figure 29B:
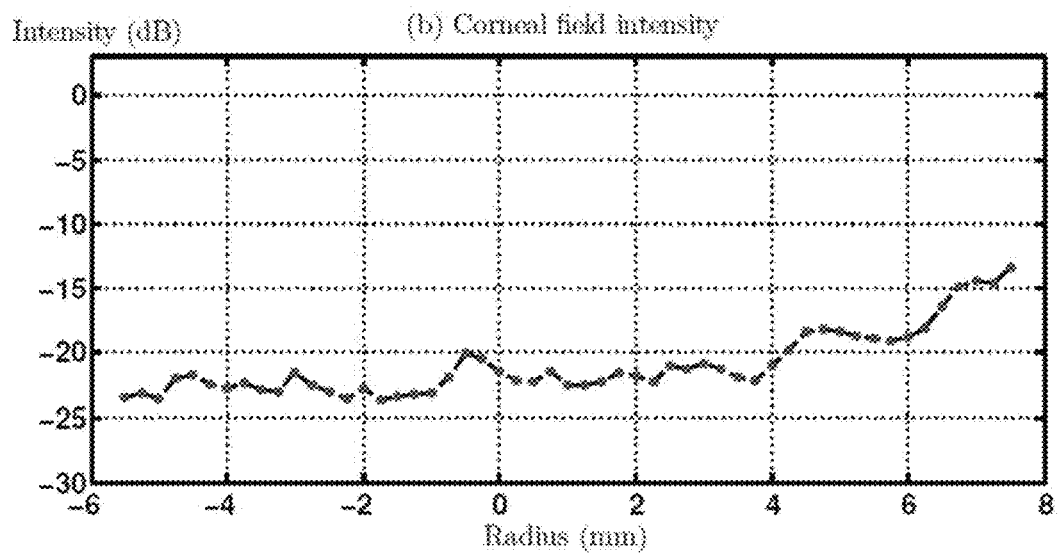

FIGS. 29a and 29b illustrate example graphs of the relative field intensities.

Figure 30A:
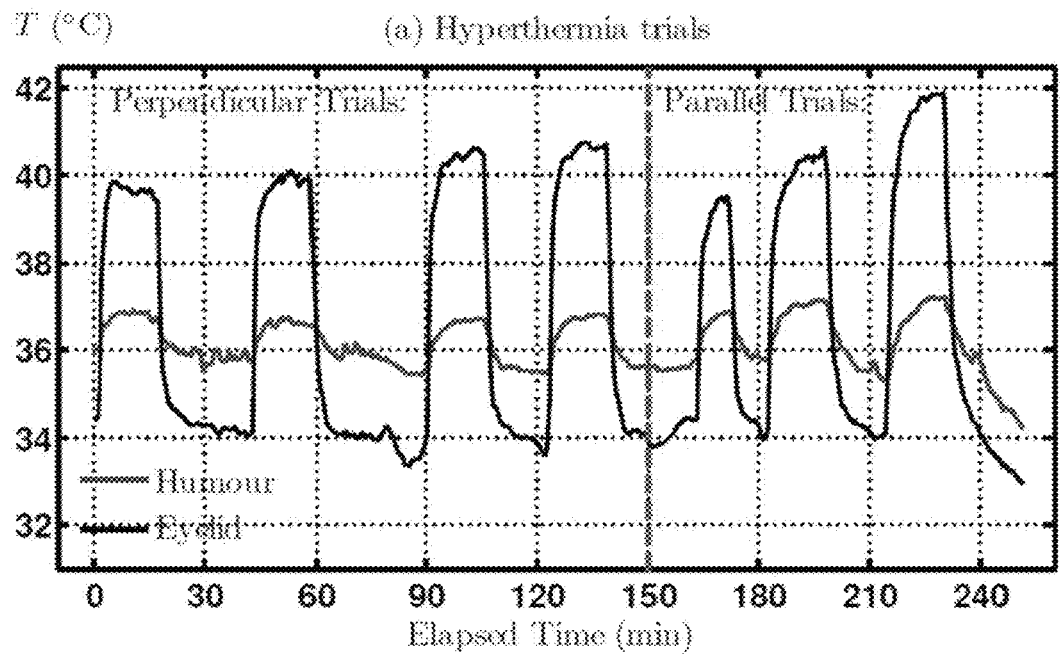
Figure 30B:
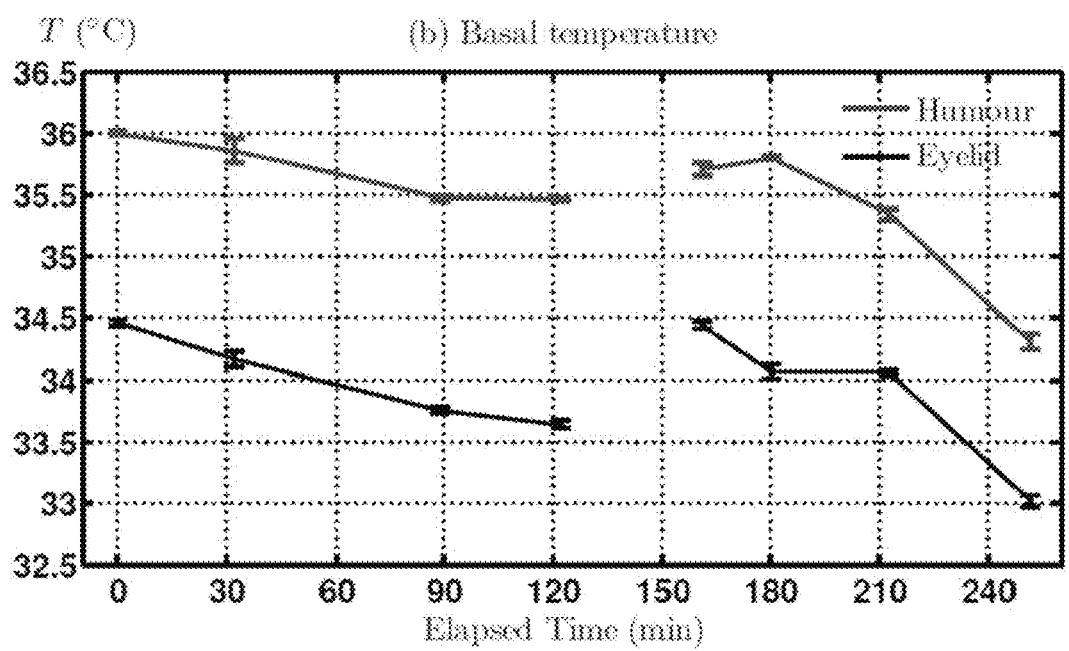

FIGS. 30a and 30b illustrate examples graphs of heating curves.

FIGS. 31a, 31b, 32a, 32b, 33a, 33b, 36a and 36b illustrate example graphs of temperature curves.

Figure 34A:
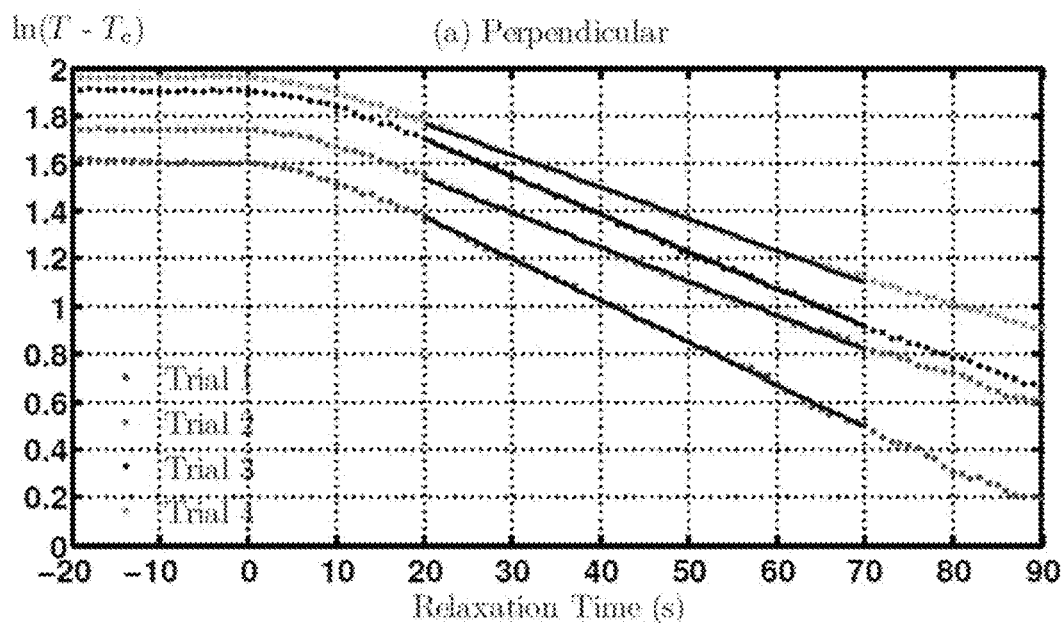
Figure 34B:
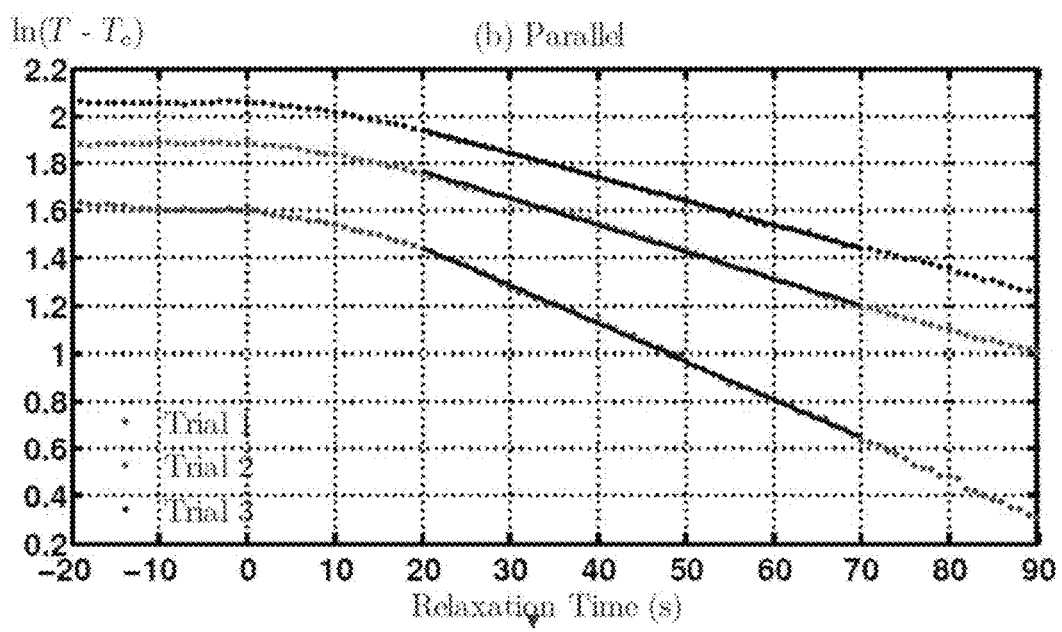
Figure 35:
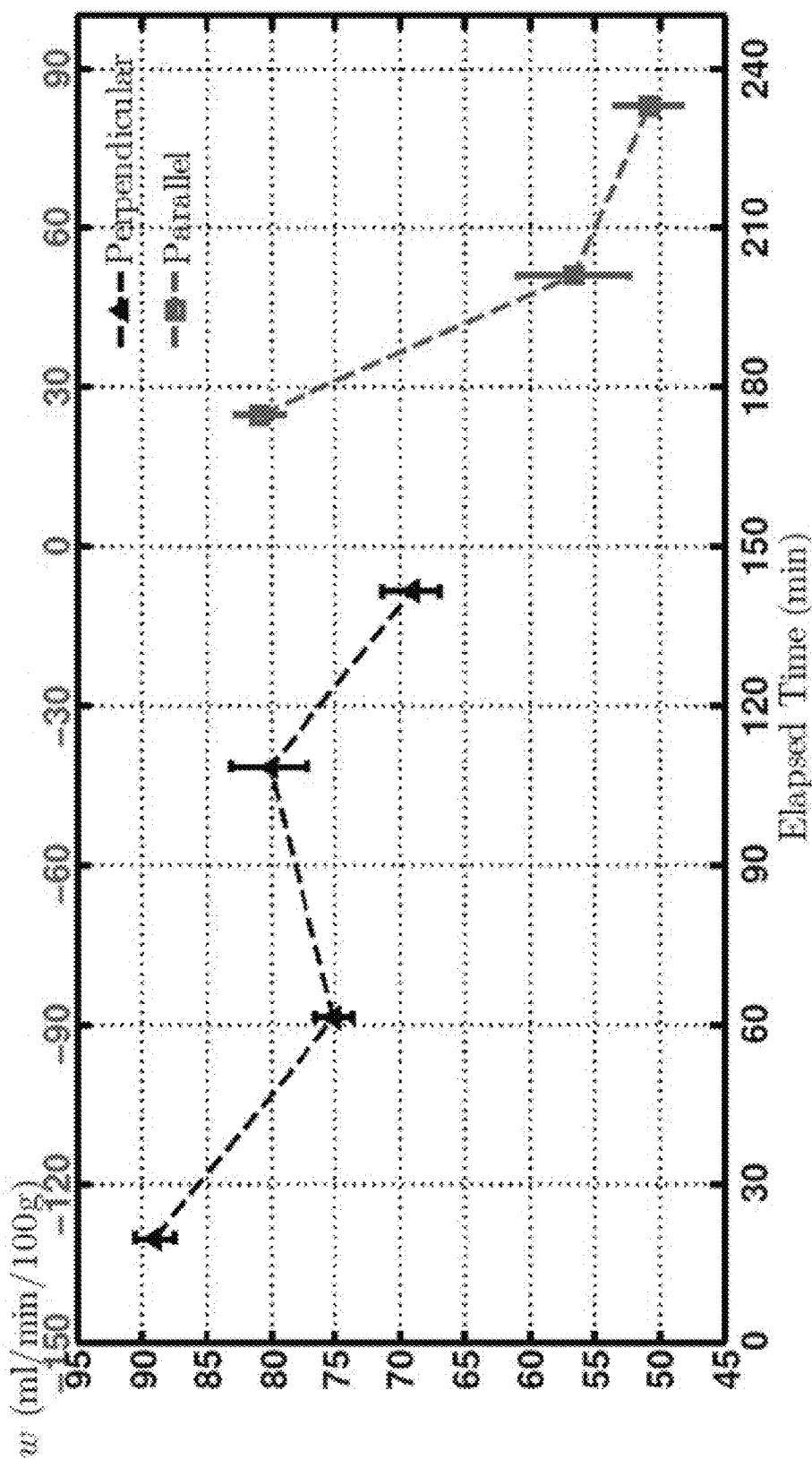

FIGS. 34a, 34b, and 35 illustrate example graphs of time curves.

The drawings, described below, are provided for purposes of illustration of the aspects and features of various examples of embodiments described herein. For simplicity and clarity of illustration, elements shown in the figures have not necessarily been drawn to scale. The dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description should be considered as describing implementation of the various embodiments described herein.

The described embodiments relate to methods, systems and uses for therapeutic ultrasound for treating or alleviating eye conditions, such as dry eye and other conditions associated with gland dysfunction and eyelids.

Eye conditions may relate to meibomian gland dysfunction. For example, one of the underlying causes of dry eye may be meibomian gland dysfunction. Other example eye conditions include chalazion, meibomian cysts, hordeolum, stye, blepharitis and so on. Meibomian gland dysfunction may occur due to a variety of factors. These factors range from keratinization of ductules, inflammation of ducts, solidification of lipid secretions, and atrophy of glands themselves. A meibomian gland blockage, dry eye, and other eye conditions may be ameliorated with heat. The heat required to break up oil secretions involves a treatment that sufficiently warms the eyelid for a period of time. For example, heat treatment may warm the eyelids to 40 degrees Celsius for four minutes. This is an example only and other time periods may be used depending on temperatures used. Hot water (wet towel) compresses may be used to apply wet heat to the eyelids. Although efficacious, patient compliance may be a problem and the technique may be error prone as the compress may not warm eyelids to sufficiently warm temperatures. As another treatment approach, a product may heat the eyelids and massage them to facilitate expression of oil contents. Although efficacious this treatment product may be costly and a transducer head may have to be purchased for each patient.

The described embodiments relate to methods, systems and uses for therapeutic ultrasound for eye conditions by providing heat and oscillatory ultrasound energy to the eyelids, meibomian glands, lacrimal gland, or other glands and areas proximate eye. By using therapeutic ultrasound energy the depth of tissue penetration may be minimized while the amount of energy delivered to the tissue may be maximized.

For therapeutic ultrasound, the frequency used typically ranges from 0.2 to 10 MHz depending on tissue depth penetration. Absorption and therefore energy deposition increases with increasing frequency. Since the eyelid is only several millimeters in thickness a range of different frequencies may be used by the described embodiments to heat the eyelid and meibomian glands. The ultrasound transducer may provide therapeutic ultrasound generally across the frequency range 0.2 to 10 MHz according to some embodiments. In other embodiments the frequency range may extend as high as 50 MHz. Alternatively, a lower frequency therapeutic ultrasound may be used at a higher power setting or a longer duration to generate sufficient heat. The use of therapeutic ultrasound may help emulsify blocked fats by two distinct example mechanisms. For example, the high frequency ultrasound may provide heat energy to fats in the gland. The heat energy delivered may liquefy solidified fats. The oscillations would further act to mobilize oil movement through the formation of small bubbles in the oil medium. This may be referred to as microcavitation. Accordingly, the use of therapeutic ultrasound may heat the gland to liquefy fat blockage and create microcavitation.

Ultrasound energy may further facilitate movement of oil within the glands and/or ductules through acoustic streaming. The therapeutic ultrasound may also stimulate circulation in the eyelid and meibomian gland, which may promote clearance of inflammatory mediators. Further, the therapeutic ultrasound may help breakdown and remodel scar tissue in the eyelid, which may be the result of a chalazion, or other trauma or infection/inflammation to eyelid. Therapeutic ultrasound may be used post-surgically on the eyelid to reduce scar formation and facilitate healing of tissue after eyelid surgery. These eyelid surgeries could include but would not be limited to blepharoplasty, ptosis repair, entropion repair, ectropion repair, excisional and incisional biopsies and so on. When used to remodel scar tissue therapeutic ultrasound could be combined with other treatments such as intralesional injection of corticosteroids or topical application of steroids and other anti-inflammatories. In this situation therapeutic ultrasound may facilitate penetration of and distribution of medications through the process of phonophoresis. Ultrasound could be used over the eyelids or meibomian glands to promote drug delivery of other topical medications through the process of phonophoresis Alternatively, or in conjunction with being directed on the meibomian glands, ultrasound energy could be directed superotemporally in the orbit to focus energy on the lacrimal gland. This acoustic energy may stimulate secretion of tears from the lacrimal gland through to the lacrimal ducts.

In addition to aforementioned applications of therapeutic ocular ultrasound, if the power and frequency settings are varied, ultrasound energy may be directed medially at the nasolacrimal duct apparatus to resolve partial and complete blockages. Ultrasound energy can be used to resolve blockages of the upper and lower canalaculi, the lacrimal sac, or the nasolacrimal duct itself. The ultrasound could be used at lower settings to facilitate flow through the entire apparatus in partial blockages or functional blockages. The ultrasound may be used at higher energy settings to break up stones if they are obstructing the passages. This technique may be directed to stones located anywhere along the entire course of the nasolacrimal system. This ultrasound method may be analogous to the lithotripsy used for treatment of kidney stones. A small probe attachment may be used for this application as it would allow the clinician to focus or broaden ultrasound energy around the desired location.

Figure 1:
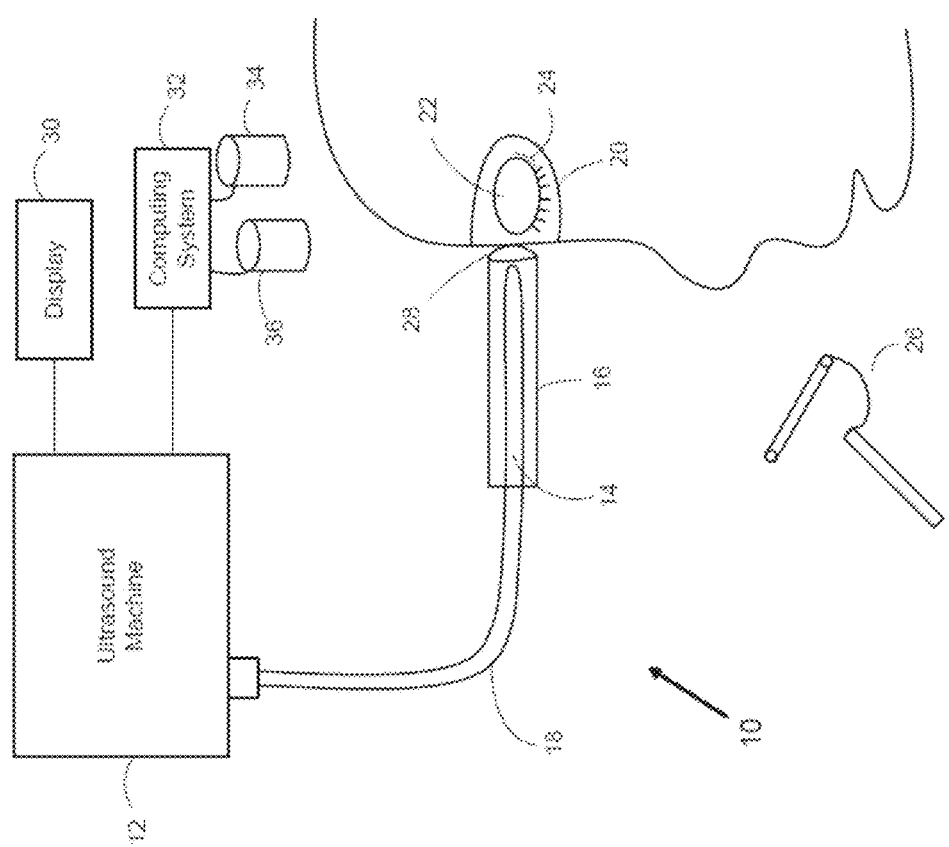
FIG. 1 shows a diagram of a system for eye conditions using therapeutic ultrasound according to some embodiments.

Referring now to FIG. 1 there is shown a system using therapeutic ultrasound for eye conditions. The system 10 is operable to connect a transducer head 16 to an ultrasound machine 12 via connector 18. The transducer head 16 may be shaped to complement various portions of the eye. Further, the transducer head may include a small probe attachment sized proportional to the portion of the eye to be treated in order to focus or broaden energy on the specific treatment portion of the eye.

The transducer head 16 may also include a piezoelectric crystal 14 or numerous crystals as a non-limiting illustrative example. Other example transducer heads 16 are electromagnetic transducers, PZT transducers, and so on. This is an example transducer and other types may be used. For example, transducer may be constructed from a piezoelectric ceramic with perovskite structure, such as lead zirconate titanate (PZT) its varieties. The transducer may also be made from a piezoelectric polymer, such as polyvinylidene fluoride (PVDF) film (or other material) for example. Piezoceramics may include PZT and PZT-varieties, barium titanate, lead titanate, lead zirconate titanate, potassium niobate, lithium niobate, lithium tantalate, sodium tungstate, zinc oxide, and so on.

In this illustrative example, the system 10 is operable to deliver energy through the ultrasound machine 12 to the transducer head 16 coupled to the closed eyelid 24. A gel 20 may be used as a coupling medium to allow direct contact of the transducer head to the closed eyelid 24. The external transducer may also be able to move along the entire length of the meibomian glands.

Embodiments may include a contact lens with internal air chamber and the transducer may be applied externally through the eyelid. This may enable a longer transducer length to cover the entire length of the meibomian glands. The internal air gap and lens may impede ultrasound gel or water getting into the air gap. Ultrasound gel may get under the contact lens and irritate the eye.

The shape of the contact lens may vary, and in some example embodiments may be elliptical to maximize the number of meibomian glands treated across the full horizontal length of the eyelid.

The ultrasound machine 12 may operate at a varying frequencies depending on the treatment parameters. For example, a lower frequency at a higher power (or amplitude) may also be used. The ultrasound transducer may provide therapeutic ultrasound generally across the frequency range 0.2 to 10 MHz according to some embodiments. In other embodiments the frequency range may extend as high as 50 MHz. The delivery of ultrasound energy may be continuous or pulsed. Pulsed energy may allow for a slower heat rise than continuous ultrasound energy at the same intensity. A pulsed ultrasound application may take longer to warm the tissue but may provide a larger safety margin and reduce chance of tissue burn. This is an example configuration of a system.

In another aspect, there is provided a system for treating an eye condition comprising an air gap lens and one or more ultrasound transducers. The ultrasound transducer may be positioned within or on the air gap lens, as described herein. FIG. 9 provides an example representation.

Referring back to FIG. 1, the ultrasound machine 12 is configured for treatment of an eye condition, such as dry eye, dysfunction of the meibomian gland, lacrimal gland, periocular gland, and nasolacrimal system, chalazion, and scarring. The ultrasound transducer 16 is adapted for eye treatment and suitable for coupling to at least a portion of an eyelid to supply ultrasound waves to the eyelid according to treatment parameters. The treatment parameters may include a frequency, an amplitude (e.g. power), an on/off cycle (e.g. for pulses), a phase, and a treatment period. An example treatment frequency range is between 0.2 MHz, 10 MHz, up to 50 MHz and further examples are provided herein. The treatment parameters may specify a range of frequencies and amplitudes for the ultrasound waves.

The ultrasound machine 12 may also be connected to a temperature measurement device (e.g. measurement tool 25 of FIG. 5) that is configured to measure temperature elevations induced by deposition of acoustic energy to the eyelid by the ultrasound transducer 16. If the temperature increases above the range a warning alert may be generated to adjust the treatment parameters or the transducer 16 may be shut down automatically to avoid damage to the eye or eyelid. If the temperature decreases below the range an alert may be generated to adjust the treatment parameters. An example temperature measurement device may be a thermocouple. A measurement device may also measure ultrasound waves and provide the measurement data to ultrasound machine 12. If the ultrasound waves pass a predetermined safety threshold then the transducer 16 may automatically shut down or adjust to stay within the safety threshold. An example measurement device for ultrasound waves is a hydrophone.

The frequency range may provide sufficient ultrasound energy to heat the treatment area of the eye. For example, the frequency range of 0.2 MHz to 50 MHz or higher may provide sufficient ultrasound energy to heat the treatment area of the eye to 40 degrees Celsius. Tissue denaturation may start at temperatures over 43 when applied for long treatment periods, such as over 200 minutes. The treatment period may be proportional to the treatment frequency, as a lower frequency may require a longer period and vice versa. Example treatment periods range between thirty seconds to twenty minutes, one minute to ten minutes, and two to five minutes, or longer depending on the treatment parameters. These are non-limiting example treatment periods and frequencies and others may be used.

The eye condition may be caused by lipids blocked in a gland of the eye and the ultrasound waves may heat the treatment area of the eyelid to emulsify the lipids blocked in the gland. As noted herein, the ultrasound waves may supply oscillations to move the emulsified lipids by creating bubbles in the emulsified lipids, may supply acoustic streaming to mobilize the emulsified lipids, may cause mircocavitation to mobilize the emulsified lipids, stimulate circulation in the area proximate to the portion of the eyelid, and breakdown scar tissue in the area proximate to the portion of the eyelid.

The ultrasound machine 12 may include a controller to receive treatment data from a data source (e.g. computing system 32 or other third party networked system). The controller may process the treatment data to determine the treatment parameters and direct the ultrasound transducer 16 to propagate ultrasound waves according to the treatment parameters. The treatment data may define eye condition, measurements, location, and so on. The ultrasound machine 12 may also connect to an ultrasound imaging camera. The ultrasound machine 12 is operable in a therapeutic mode to heat the area proximate to the portion of the eyelid. The ultrasound machine 12 is operable in a diagnostic mode to image the area proximate to the portion of the eyelid using the ultrasound imaging camera. The imaging camera could visualize the consolidated meibum in the meibomian gland and its ductules. It could also quantify the amount of meibum in the glands. A reduction in meibomian gland volume would confirm that oil was expressed out of the glands and ductules The diagnostic mode may be used to collect treatment data regarding the eye condition.

The system 10 may also include a roller 26 to express oil secretions from the meibomian glands. The roller 26 may have various shapes, such as a curve or concave shape to complement the eye.

The piezoelectric crystal 14 may be a PZT-8 or similar material, or may use other techniques such as electromagnetic. The ultrasound machine 12 may be powered by various means such as by a standard current or an internal battery. The transducer head 16 may be a plastic material forming a sealed transducer, a head cover, and so on. The transducer head 16 may have various shapes and components, such as a curved or concave shape complementary to eyelid, elliptical shape, a flat head, thin plates extension, probe attachments, and so on. The piezoelectric crystal 14 may contract and expand based on the ultrasonic frequency signals supplied by the ultrasound machine 12 to generate ultrasonic pressure waves which are coupled to the closed eyelid 24 via transducer 16. Any oscillating component with a transducer head 16 may provide ultrasound energy through the probe to the eyelid, meibomian glands, lacrimal gland, periocular glands or nasolacrimal system. The transmission of the pressure waves into the closed eyelid 24 may be enhanced by the gel 20. The ultrasonic pressure waves propagate through the closed eyelid 24 to the meibomian glands, lacrimal gland, periocular glands or nasolacrimal system.

Transducer 16 may be held in place by an adhesive, a clip, or by a health assistant for a treatment period. When the treatment is applied by a health assistant the probe may be slowly moved over the closed eyelid 24. Moving the transducer head 16 during treatment may be important because of the following effects: to smooth out irregularities of the near field, to minimize hotspot formation, to reduce irregularities of absorption that might occur due to reflection, interfaces, standing waves, refraction, and differences in tissue thermal conduction or blood flow. It is estimated that at an output 1 W/cm2 there is a rise of 0.8 C/min if vascular cooling effects are ignored.

Alternatively, instead of the transducer head 16 being moved by the clinician over the tissue of the eyelid 24, the transducer head 16 may be stationary or fixed to the eyelid 24. If mobile, a ultrasound transducers could be employed and this may have a single active element that both generates and receives high frequency sound waves, or two paired elements one for transmitting and one for receiving. In contrast, if stationary, a head 16 with multiple components could vary the ultrasound beam applied from the transducer.

The transducer head 16 may have moving components within the head that vary the ultrasound beam applied from the transducer 16.

A phased array may be used to vary the application of the ultrasound across the treatment field. This may allow the clinician to simply apply the transducer 16 (or probe attached thereto) to the eyelid 24 or fasten/adhere it in place without constantly moving the transducer 16 (or probe attached thereto). Wth this phased array the risk of having a standing wave or a hotspot may be greatly reduced. The phased array could be arranged in a strip (linear array), a ring (annular array), a circular matrix (circular array), or a more complex shape such as an ellipse that would conform to the shape of the eyelids.

The system 10 may also include a display for displaying images and video from ultrasound machine 12 and a computing system 32 with a processor and memory 34 for processing captured data, images and video. The computing system 32 may be operable to store data/images/video in memory 34 and/or an imaging database 36. The transducer 16 may have an imaging component 28. The ultrasound 12 and transducer 16 may be used in a diagnostic setting to image the gland and eyelid 24, as well as a therapeutic setting to heat the eyelid 24 and gland. The gland and surrounding tissues could be imaged in real time as the treatment is provided by the transducer head 16. A dual transducer may be used to image and treat. The images may provide a visual indication of treatment progression for a patient.

The imaging camera could visualize the consolidated meibum in the meibomian gland and its ductules. It could also quantify the amount of meibum in the glands. A reduction in meibomian gland volume would confirm that oil was expressed out of the glands and ductules.

Referring now to FIG. 2 there is shown a diagram of a meibomian gland and duct 40, with a fat blockage 44. There is also shown an illustrative view of the meibomian gland and duct 40. As shown the meibomian gland and duct 40 may be located in the eyelid 24 near the eye globe 42.

Ultrasound energy may be passed into the ocular tissues, which may incite inflammation and potentially cause cataract formation. In accordance with embodiments described herein, systems, methods and uses may involve a vaulted scleral contact lens 22. The lens 22 may be placed over the eye globe and under the eyelids 24 to form a chamber of air. The chamber of air may be between lens layers or the posterior surface of the contact lens and the cornea itself. Since ultrasound energy does not pass well through gases this vaulted chamber may act as a barrier to ultrasound transmission effectively shielding the eye from the ultrasound energy. Alternatively, a lens speculum may be applied to the eye to elevate eyelid 24 from eye globe and create an airspace between eye globe and eyelid 24.

The transducer 16 may be applied to eyelid at different angles and directions. Referring now to FIG. 3 there is shown uses of therapeutic ultrasound for eye conditions. In one example, a transducer head 16 may have a curved shape to complement the eyelid 24. The transducer head 16 may propagate ultrasound waves towards the eyelid 24 and eye globe 42 to liquefy fat blockage 44 in the gland 40. A lens 22 may create or include a chamber of air 46 to protect the eye globe 42. The lens 22 may be placed over the eye globe 42 and under the eyelids 24 to form a chamber of air 46 between the posterior surface of the contact lens 22 and the cornea itself. The chamber of air may also be within the lens, between layers of the lens.

The contact lens could also be made of an absorptive material that does not allow penetration of ultrasound energy, or the chamber of air (e.g. air gap) may block penetration of ultrasound energy. In some cases the contact lens may form a sufficient barrier so that it would not need to be vaulted off the globe. Alternatively, a lens speculum (not shown) may be applied to the eye to elevate eyelid 24 from eye globe 42 and create an airspace between eye globe and eyelid 24. In another example, the transducer head 16 may propagate ultrasound waves away from the eye globe 42 using thin plates which form part of transducer head 16.

Figure 5:
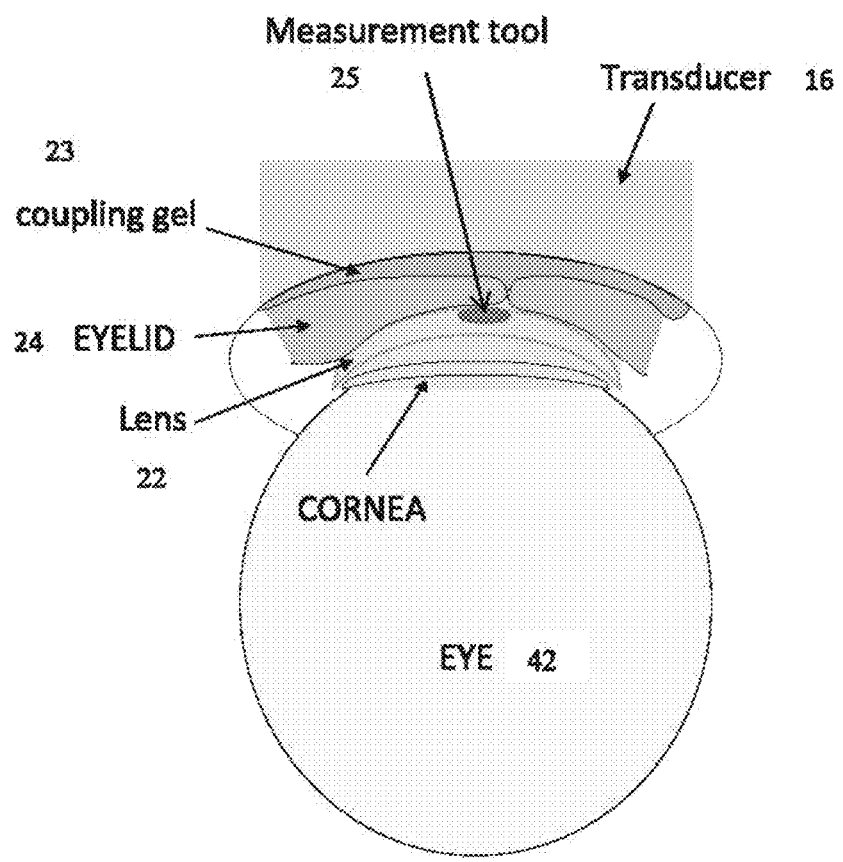
FIG. 5 shows another diagram of a use of therapeutic ultrasound for eye conditions according to some embodiments.

Referring now to FIG. 5 there is shown another diagram of a use of therapeutic ultrasound for eye conditions. The transducer head 16 may have a curved shape to complement the eyelid 24. The transducer head 16 may propagate ultrasound waves towards the eyelid 24 and eye globe 42. A lens 22 may be positioned on top of the cornea and covered by the eyelid 24. The lens 22 may be vaulted to protect eye globe 42 by creating a chamber of air between the posterior surface of the contact lens 22 and the cornea itself. The lens 22 may also include multiple layers creating a chamber of air. The contact lens 22 may also be made of an absorptive material that does not allow penetration of ultrasound energy. In this case the contact lens would form a sufficient barrier so that it would not need to be vaulted off the globe. Coupling gel 23 may be applied on top of the eyelid 24 to act as a coupling medium between the tissue and the transducer 16. Ultrasound waves may be transmitted by the transducer 16 into the eyelid 24.

A temperature and attenuation measurement device may be positioned proximate to the lens or other area to collect and record temperatures and attenuation measurements to monitor heating of eye 42. For example, a measurement tool 25 may be positioned on the lens 22 in order to take temperature measurements. The measurement tool 25 may be a thermocouple. The measurement tool 25 may provide temperature data to controller. If the temperature exceeds a safety threshold the controller may automatically shut off the transducer 16 to ensure the eye 42 is not damaged, automatically adjust the treatment parameters to reduce the temperature, or send an alert notification. The measurement tool 25 may be positioned on the lens 22 using glue or other adhesive. It may also be built within the lens 22.

Figure 4:
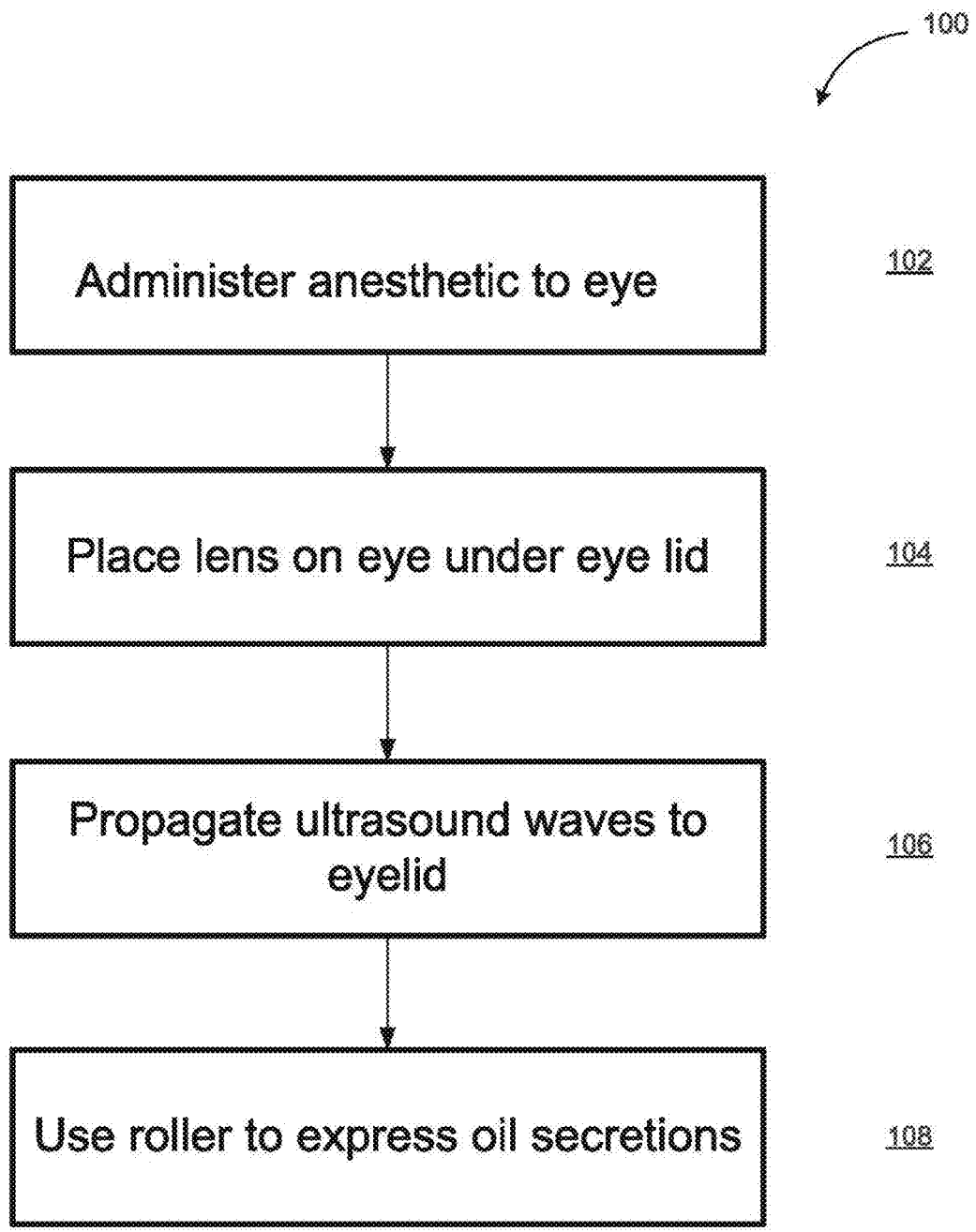
FIG. 4 shows a diagram of a method using ultrasound for eye conditions according to some embodiments.

Referring now to FIG. 4 there is shown a method 100 of using high frequency ultrasound for eye conditions. The method 100 may be use high frequency ultrasound to liquefy solidified fats in the meibomian gland, or other glands/ducts. At 102, a clinician may administer a drop of tetracaine or equivalent topical anesthetic unto the eye. At 104, a lens 22 may be placed onto the eye. At 106, the ultrasound transducer 16 propagates the high frequency ultrasound waves (such as 0.2 to 50 MHz). The ultrasound transducer 16 may be affixed on or within the lens 22. The ultrasound transducer 16 may also be applied to both closed eyelids 24 through a coupling gel 20 medium for a treatment period, such as for example a two to five minutes treatment for each eye, or for longer depending on the frequency. After the heating treatment, at 108, a mechanical roller may be used to express oil secretions from the meibomian glands. This may occur while the contact lens 22 shield is still in place. For example, this roller may be applied from a proximal to distal direction in the direction of the meibum flow within the glands themselves. Alternatively, a cotton swap (e.g. Q-tip) or other instrument may be used to guide oil. Post treatment, the patient may be placed on a short course of topical steroids (or NSAIDs) to minimize any post-procedural inflammation.

Figure 6:
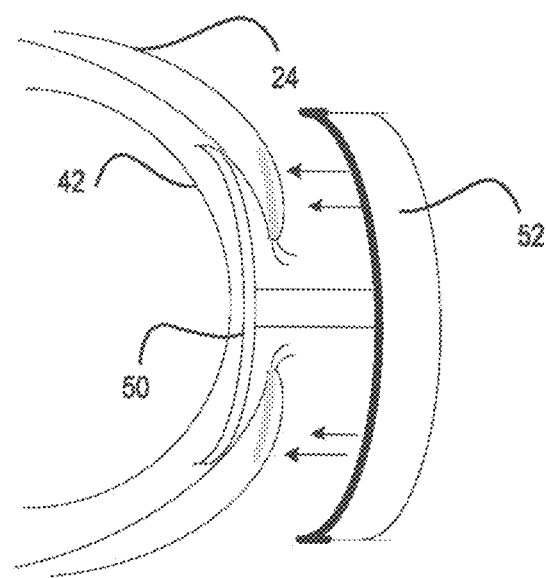
FIG. 6 shows a diagram of a use of therapeutic ultrasound with an attachment for eye conditions according to some embodiments.

Referring now to FIG. 6, there is shown a diagram of a use of therapeutic ultrasound with an attachment for eye conditions according to some embodiments. The attachment 52 may couple to the transducer 16 in order to propagate ultrasound waves to the eyelid 24. The attachment 52 may include a protective portion 50 shaped to complement the eye 42 and protect the eye 42 from the ultrasound waves. The attachment 52 and protective portion 50 may clip onto the patient's head or eye 42 (or otherwise attach) for the duration of the treatment period. Embodiments may include an external transducer shaped to complement the gland for treatment. The transducer may be of a longer length than the air gap lens to maximize treatment area. The external transducer may also be able to move along the entire length of the meibomian glands.

Figure 7:
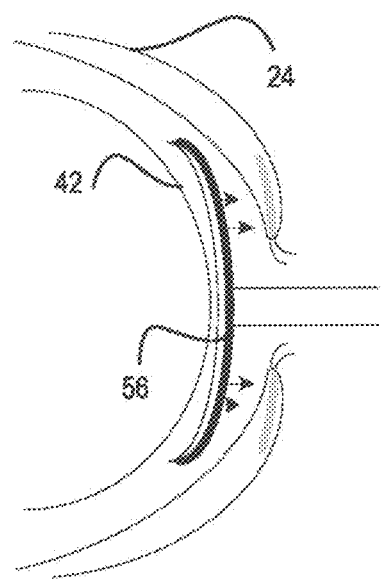
FIG. 7 shows another diagram of a use of therapeutic ultrasound with an attachment for eye conditions according to some embodiments.

Referring now to FIG. 7, there is shown another diagram of a use of therapeutic ultrasound with an attachment for eye conditions according to some embodiments. The attachment 56 may couple to the transducer 16 in order to propagate ultrasound waves through the eyelid 24 but away from eye globe 42. The attachment 56 is shaped to complement the eye 42 and eye lid 24 and position there between. In this example, the ultrasound waves propagate away from the eye 42 to reduce chance of harm due to heat. This may protect the eye 42 from the ultrasound waves. The attachment 56 may clip onto the patient's head or eye 42 (or otherwise attach) for the duration of the treatment period. This is another example of an external transducer which may be used with the air gap lens.

As described herein, ultrasound energy may be passed into the ocular tissues, which may harm the eye. In accordance with embodiments described herein, systems, methods and uses may involve a contact lens 22. The lens 22 may include a chamber of air created by lens layers. The lens 22 may be placed over the eye globe and under the eyelids 24. the lens 22 may form or provide a chamber of air to protect the cornea. The chamber of air may act as a barrier to ultrasound transmission effectively shielding the eye from the ultrasound energy. Alternatively, a lens speculum may be applied to the eye to elevate eyelid 24 from eye globe and create an airspace between eye globe and eyelid 24.

Dry eye is a complex disorder that affects a significant portion of the population. A form of the disease is Evaporative dry eye disease which is a disorder of the ocular surface and tear film causing pain and low vision in a significant portion of the adult population. The most common cause is obstructive meibomian gland dysfunction ("MGD"), whereby the meibomian glands secrete abnormally keratinized, viscous meibum with a melting point approximately 3-4° C. higher than normal. Dry Eye is typically treated with heat, aiming to liquify the solidified meibum at the meibomian ducts. The ocular surface is coated by a tear/lipid bilayer. The lipid functions to provide a smooth optical surface, and retard tear evaporation. Dry eye may be caused by obstructed meibomian glands. Reduced meibum may lead to increased and excessive tear evaporation.

Embodiments described herein may reduce or treat dry eye using an ultrasound hyperthermia device with a contact lens. There may be an internal transducer contained within a contact lens with an internal air gap. The internal transducer may be of polyvinylidene fluoride (PVDF) film (or other material) for example. This is an example transducer and other types may be used. For example, piezoelectric transducer may be constructed from a piezeoelectric ceramic with perovskite structure, such as lead zirconate titanate (PZT) its varieties. The transducer may also be made from a piezoelectric polymer, such as PVDF. Piezoceramics may include PZT and PZT-varieties, barium titanate, lead titanate, lead zirconate titanate, potassium niobate, lithium niobate, lithium tantalate, sodium tungstate, zinc oxide, and so on.

A prototype of this device may be built in a planar geometry to test its feasibility. Ex vivo experiments with porcine eyelid and cornea tissue may be performed with the device with low amplitudes (30-35 V) and a relatively low duty cycle (25%) as an illustrative example. A temperature rise of 4.5° C. in the eyelid may be achievable in a short timeframe. A vacuum mould may be used to form a spheroidal concavity in a PVDF film. This film may then be fixed between two contact lenses (created an air gap) providing an air backing to the transducer, with the electrical connections contained inside this gap.

Dry eye is a complex, multifactorial disorder of the ocular surface and tear film due either to tear deficiency or excessive tear evaporation. It affects vision and comfort in a significant portion of the population The meibomian glands are modified sebaceous glands diffusely located within the inner tarsal plate, numbering approximately 25 and 20 in the upper and lower lids, respectively. They are responsible for the secretion of meibum, the lipid portion of the tear layer that serves several purposes. Primarily the meibomian lipid is a hydrophobic seal on the aqueous tear film, preventing its evaporation and enhancing the film stability through a reduced surface tension. Like Dry Eye, MGD is a broad collection of different conditions with many causes. However, the most common clinical form of MGD is obstructive, diagnosed according to reduced excretion or abnormality of the meibum. The common case finds obstructive MGD, where the ducts by which meibum reaches the muco-aqueous surface are blocked by abnormally viscous, keratinized meibum. Ultimately, MGD entails that insufficient levels of meibomian lipid are present for sealing the aqueous tear film.

A method of treatment for evaporative dry eye caused by MGD has been heat therapy in the form of warm compresses and/or manual gland expression through mechanical pressure. Meibomian lipid is liquid at lid temperature in healthy patients, melting at 32-40° C., however abnormal meibum has an elevated secretion temperature by approximately 3° C. Studies of the chemical composition of meibum have found an increase in phase transition temperature of 4° C., defined by several parameters of inter-molecular order. Hence, heat therapy aims to liquify the keratinized meibum at the meibomian ducts by raising the temperature of the tarsal plate. Careful application of heat to the eyelids may increase the thickness of the tear lipid layer. Treatment methods that use heat sources may apply heat to the outer surface of the eye, where efficacy of heat applied to the outer surface of the eyelid is debatable since the applied heat must diffuse through the dense muscle tissue of the tarsal plate with a strong vascular supply. This may be an even greater impediment for patients attempting to self-administer warm compresses since care must be taken to ensure the compresses remain at a constant, elevated temperature to provide an effective heat source.

Embodiments described herein may use High Focused Intensity Ultrasound (HIFU). HIFU may be applied with relatively low duty cycles (≤10%), which allows the tissue to cool and achieve a stable temperature increase within the 39-44° C. regime. Increasing the duty cycle while concomitantly decreasing the amplitude results in comparable power deposition to HIFU, but with a lower ultrasonic intensity. Given the melting temperature of keratinized meibum at ~42° C., this range may be used for a mild ultrasound hyperthermia treatment.

Embodiments described herein may an ultrasound device for mild hyperthermia in the tarsal plate. Embodiments described herein may elevate the temperature of the eyelid interior to the melting point of abnormal meibomian lipid, taken as 41-43° C.—a regime demonstrated effective. Due to the strong vascular supply of the tarsal plate, the interior of the eyelid may be assumed to be near the temperature of blood, at around 37° C.

Embodiments described herein may use a device that consists of a transducer within a large scleral contact lens with an air gap, wherein the transducer is attached to the lens (affixed thereto or within), which is in contact with the conjunctival epithelium. Inside the air gap lens, the transducer is air-backed and hence reflects essentially all acoustic energy forwards through the front lens into the tarsal plate. This is a safety consideration, as the application of heat could cause corneal deformation, possibly affecting or impairing vision. As low a temperature rise in the cornea as reasonably possible may be desired, such as below the 50° C. upper bound. An extremely conservative limit of <40° may be used, corresponding to a maximum 6° C. rise given the ocular surface temperatures measurements in the range 32-34° C. have been reported. Thus the ultrasonic energy propagates outwards towards the tarsus, delivering heat directly to the Meibomian glands. The acoustic impedance mismatch of the transducer and air reacts essentially all pressure waves away from the cornea, which is an important safety consideration discussed. The device may include a high frequency lead-zirconium titanate (e.g. PZT) piezoceramic transducer in some embodiments.

To demonstrate feasibility as a treatment device, a prototype may be constructed with a flat geometry with contact lens material and a 21 MHz PVDF film. This example illustrative geometry was elected to mimic the desired lens configuration while simplifying construction. In addition, a theoretical model of heat delivery due to acoustic pressure waves may be developed for this simplified geometry and compared with the experimental results.

Heating the external eyelid surface may require sufficient heat temperatures to diffuse through the strong eyelid vasculature. Temperature rise in the cornea may cause deformation. When heating the external surface of the eye, the temperature of the outer eyelid is higher than the temperature of the inner eyelid. That is, a linear decrease may be proportional to depth. Equilibrium may be established over time.

Treatment devices and systems in accordance with embodiments described herein may heat tarsal plate to 41° C. to 43° C. Treatment devices and systems in accordance with embodiments described herein may not deposit ultrasonic energy into cornea. Treatment devices and systems in accordance with embodiments described herein may keep cornea under 40° C. Treatment devices and systems in accordance with embodiments described herein may obtain a reasonable change in temperature for a treatment timespan. These are illustrative examples.

Embodiments described herein may involve use of a contact lens to protect an eye during treatment of the eye with a ultrasound device. As described herein, there may also be a measurement tool 25 which may be a thermocouple. As a safety mechanism a thermocouple could be placed in either the front side, back side, or both sides of the contact lens. This thermocouple may trigger the ultrasound device to turn off if the temperature was raised to an unsafe level (eg. 48 degrees celsius). This thermocouple may also give real time active feedback of temperature thus giving the technician/doctor the ability to modulate the ultrasound settings to achieve a safe and effective hyperthermia. The modulation and adjustments may be automatically configured as well. The degree of hyperthermia could also be measured and thus modulated by other means such as infrared.

Referring now to FIG. 8 there is shown an example embodiment that may involve a contact lens 70a, 70b to protect the eye. The contact lens 70a, 70b includes an inner lens 70b and an outer lens 70a and spaced apart to create an air gap 72 (e.g. chamber of air). The inner lens 70b and outer lens 70a may be attached at ends. The inner lens 70b may be positioned to protect the cornea 80. The inner lens 70b and outer lens 70a may be positioned under the eyelids 78. The contact lens 70a, 70b protects the eye during application of ultrasound energy by transducer 74 and coupling 76 via the air gap 72 which may reflect acoustic energy. This configuration and implementation may provide efficient manufacture and use. In this example, an external PZT transducer 74 may be placed on top of the eyelid. The contact lens 70a, 70b with the internal air gap 72 may be placed on cornea 80. The external PZT transducer 74 may deposit ultrasonic heating onto eyelid 78 surface where the heat may diffuse inwards.

A design is proposed in which a high frequency piezo film transducer is mounted within a contact lens. A high frequency may be desired since the attenuation of an acoustic wave increases proportionally to frequency, with a corresponding greater heat deposition. The lens contains an interior air gap between its inner surface mounting the sclera and outer surface contacting the tarsal conjunctiva. These surfaces may be referred to as scleral and tarsal, respectively. The transducer may be mechanically attached (or otherwise coupled) to the interior of the tarsal surface, moulded to the concavity of the lens. Its active face may be directed outwards towards the tarsal plate. The air gap provides an air backing layer to the transducer, reflecting essentially all of the acoustic energy forwards due to the impedance mismatch of the piezoelectric material and of air. This is to ensure that no pressure wave propagates through the scleral surface into the cornea, causing unwanted heating in the eye. Furthermore, the air gap acts as an insulating layer, delaying the heat diffusion through the front lens and eyelid into the cornea. When mounted onto the sclera, the eyelids would close overtop the lens, holding the device in place during the hyperthermia treatment. The electrical connections are contained within the air gap, with wiring exiting the lens through a hole sized to the wires and sealed airtight, passing through the palpebral fissure.

A schematic of the design when placed atop an eye is shown in FIG. 9. The example embodiment may involve a contact lens 70a, 70b to protect the eye. In this example, heat from conjunctival surface within air gap 72 between the outer lens 70a and inner lens 70b may be used. An internal transducer 82 coupled to a RF signal cable 84 may be positioned within air gap 72 between the outer lens 70a and inner lens 70b. In this example, heat is applied directed to the tarsal plate, which may protect the outer surface of the eyelid. The air gap 72 may protect the cornea 80. The internal transducer 82 may be air-backed and mounted onto the inside of the air gap lens 70a, 70b, 72. Ultrasonic heating energy is deposited directly on tarsal surface.

The feasibility of the internal air gap for protecting the cornea during an ultrasound hyperthermia treatment in the eyelid may be demonstrated using an external high frequency transducer with a protective contact lens. Wth this established, a prototype of the device with a planar geometry may be constructed, and a mild hyperthermia experiment may be conducted to monitor the temperature increase in eyelid and cornea tissue. In addition, a simplified 1-dimensional model of heat propagation with ultrasound sources may be created in MAT-LAB to model the heating of the prototype's elements using a finite element analysis, for example.

Referring now to FIG. 10 there is shown an example experiment system 90 including a transducer 74 and a contact lens 70a, 70b with air gap 72 in accordance with the configuration shown in FIG. 8. A thermocouple 86a, 86b may be coupled to the outer lens 70a and inner lens 70b to monitor temperatures.

A hyperthermia experiment may be performed in the configuration seen in FIG. 10. Two thermocouples may be embedded within lens. A protective contact lens with an internal air gap may be built from two contact lenses with suitable radii of curvature to allow a gap (e.g. 2 mm) at the epicenter when the larger was fit overtop the smaller. This may be placed atop the cornea. The eyelid tissue may be laid overtop this lens. A transducer (e.g. 15 MHz) may be positioned overtop the eyelid, applying a firm downward pressure and coupled with ultrasound gel. A 25% duty cycle sinusoidal RF signal may be used as a signal source with a peak to peak voltage of 40 V. The temperatures of both the eyelid and the cornea may be monitored during several minutes of treatment until the eyelid had increased by 4.5° to determine the efficacy of the protective air gap.

FIG. 11 provides a illustrative example planar prototype that may be constructed with 21 MHz PVDF and fluorosilicone acrylate sheets (FSA). The planar prototype may have a illustrative simpler geometry with a 250 μm lens layer, a 2.65 mm air gap, and another 250 μm lens layer. These are illustrative examples and variations in materials and configurations may be used for various embodiments.

A plastic frame may be milled with a cylindrical through-hole. Flat cylindrical disks of FSA of thickness 250 μm may be precision cut and used as lens-mimicking material for the prototype. FSA is a material used for larger corneal lenses with sufficient concavity to house a transducer, complete with its electrical wiring. The thickness of 250 μm was chosen as an example of contact lenses. Copper leads were epoxied to the electrodes of a 52 μm, 1 cm2 PVDF piezoelectric film with a corresponding centre frequency of 21 MHz using silver conductive epoxy. The transducer may then be epoxied with non-conductive epoxy to the centre of an FSA lens. The FSA lenses may then be both fixed to the plastic frame with epoxy. The copper leads may be cut from flex circuit paper, and may not significantly displace the FSA layer from the plastic frame when protruding from it. The leads may then be soldered to a coaxial cable with an SMA adapter.

An eyelid may be coupled to the upper FSA lens overtop the transducer with ultrasound gel. The cornea may be in contact with the bottom lens, again coupled with ultrasound gel. More ultrasound gel may be applied to couple the cornea both thermally and acoustically to the lens, which, due to its planar geometry (for the prototype), may not flatly abut the spheroidal cornea. Two sheathed thermocouples may be embedded in the lens, and aligned such that they were directly underneath and overtop the transducer, respectively. A 25% duty cycle sinusoidal pulse of duration 80 μs may be amplified by 60 dB for source peak to peak source voltages to the transducer of 50, 60, and 70 V in three separate trials. In each trial, the source may be applied for several minutes until the characteristic drop in the heating curve of the eyelid is observed in the range of 3-5° C. temperature increase.

Referring now to FIG. 12 there is shown an example experiment system 92 including an internal transducer 82 within a contact lens 70a, 70b and air gap 72, in accordance with the configuration shown in FIG. 9. A thermocouple 88a, 88b may be coupled to the outer lens 70a and inner lens 70b to monitor temperatures.

A 1 dimensional finite element model may be used for the example experiment system 92, created using a series of layer objects, each representing the physical media in a vertical cross-section in the hyperthermia. The use of a single dimension considers the temperature rise to a constant with respect to horizontal heat diffusion, however convective losses at the sides of each layer were considered to more accurately simulate the temperature profiles. A presentation of the model is to follow.

The cornea and eyelid may be treated as tissues with distinct properties, and the ultrasound gel between these and the lenses may be treated as water. The approximate dimensions and order of the layers, moving vertically downwards, is given below in table 1.

To determine the thicknesses, the solid layers of the eyelid tissue, the lenses, and the separation between the two lenses may be measured. The fluid layers were reasonably approximated by the separation between the tissue once force may be applied to the tissues to hold them flush to the lens. The cornea may be assumed to be indistinguishable from the aqueous humour. The corneal dimensions may be the entire diameter of the eye (~2 cm for an experiment).

TABLE 1

Order and thicknesses of the media used in the simulation.

| Position | Media | Thickness (mm) |
|---|---|---|
| 1 | Eyelid Tissue | 0.5 |
| 2 | Water | 1 |
| 3 | FSA | 0.250 |
| 4 | Air | 2.65 |
| 5 | FSA | 0.250 |
| 6 | Water | 1 |
| 7 | Cornea/Eye | 20 |

The physical properties of each medium such as density and celerity may be measured, where possible, and otherwise obtained from other sources. The acoustic attenuation of both fluorosilicone acrylate and eyelid tissue may be measured by comparison of pulse-echo signal levels from short pulses directed towards a reflecting quartz plate with a 15 MHz PZT imaging transducer, through degassed water and then through the respective materials. The attenuation of both as a function of frequency is shown for reference in FIGS. 20 and 21. The density of FSA may be computed from the mass of a cylindrical block of the material of known dimensions, and its celerity may be calculated from the same pulse-echo experiments as the attenuation.

The imaging camera could visualize the consolidated meibum in the meibomian gland and its ductules. It could also quantify the amount of meibum in the glands. A reduction in meibomian gland volume would confirm that oil was expressed out of the glands and ductules.

Eyelid tissue is comprised of several layers. The outermost layer of skin is the thinnest in the body at less than 2 mm due to little development of the dermis; as such it is primarily composed of muscle and fibrous membranes. As such, the eyelid may be treated as muscle, not skin, when selecting its physical and thermal properties from the literature. The physical properties of each layer, where applicable, are summarized in table 2 where ρ denotes the density; $c\_0$, the speed of sound; and α, the attenuation.

TABLE 2

Physical properties used in the simulation.

| | ρ (kg/m³) | $c_0$ (m/s) | α (dB/cm) |
|---|---|---|---|
| Eyelid | 1050 | 1580 | 288 |
| FSA | 1266* | 1490* | 86* |
| Cornea | 1062 | — | — |
| Water | 1000 | 1500 | 0 |
| Air | 1.225 | 350 | — |

An asterisk denotes a measured quantity.

The thermal properties of each media are summarized in table 3. Here, k denotes the conductivity and c, the specific heat capacity. For FSA, the thermal properties of polymethylmethacrylate (PMMA) may be used in lieu, as PMMA may be used as material in contact lenses.

TABLE 3

Thermal properties used in the simulation.

|  | c (J/kg/K) | k (W/m/K) |
|---|---|---|
| Eyelid | 3600 | 0.55 |
| FSA | 1466 | 0.167 |
| Cornea | 3740 | 0.58 |
| Water | 4182 | 0.6 |
| Air | 1000 | 0.025 |

To determine the temperature profile T(x,t) in each layer as a function of depth (x) and time (t), the heat equation may be numerically solved in each layer using discrete elements at specified depths according to:

$$\frac{\partial T(x,t)}{\partial t} = \gamma \frac{\partial^2 T(x,t)}{\partial x^2} + \frac{\dot{Q}(x,t)}{pc} \quad (1)$$

where $$\gamma = \frac{k}{pc}$$

is the thermal diffusivity in m²/s and $\dot{Q}$ represents an ultrasonic heat source term per unit volume, which, for an incident acoustic intensity $I_0$, is expressed using the time-averaged intensity as:

$$\dot{Q}(x) = \alpha I_0 e^{-\alpha x} \quad (2)$$

where x is the depth the pressure wave has travelled in the medium.

$I_0$ may be computed based on a rudimentary power dissipation model of a parallel plate capacitor with capacitance C and known area A. An efficiency ε of conversion from electrical to mechanical energy may be assumed, and a PiezoCAD simulation may compute the upper bound for the energy conversion to be 20%. As this is very high estimate, an efficiency of ten times less at 2% may be assumed, as there are resistive losses associated with conductive epoxy. Using the power amplitude of a capacitor, for an input voltage $V_0$ at frequency f, the acoustic intensity is:

$$I_0 = \epsilon \frac{2\pi f C V_0^2}{A} \quad (3)$$

The ultrasonic wave at the surface of the capacitor may be considered a uniform plane wave in one dimension. No acoustic energy may be assumed to propagate through the air medium; instead the energy may be reflected and the incident intensity in the FSA layer 3 was doubled accordingly. A further consideration may be given to the thin layer of epoxy that held the transducer to the lens surface by subtracting a known attenuation of a common epoxy.

The boundary conditions between each layer may be specified according to convective heat transfer at that boundary. The spatial derivative of the ith layer $$\frac{\partial T_i}{\partial x}$$

may satisfy $$-k \frac{\partial T_i}{\partial x} = h(T_{i+1} - T_i) \quad (4)$$

where $T_i$ and $T_{i+1}$ are the temperatures on either side of the boundary between two layers. The constant h is a heat transfer coefficient in W/m²K. Although h is dependent entirely on the interface type and difficult to accurately measure, representative ranges are readily-available for static air and water, as 10-100 and 20-1000 W/m², respectively.

To account for convective losses along the horizontal faces of each media layer in the hyperthermia experiment, an additional boundary may be considered for each layer. The tissues used in the experiment may be stored in saline and hence may be covered in an aqueous layer. Because of this, the value of h in equation 4 may be identical to that for convective transfer with the water layers. Hence, as an approximation, the derivative $$\frac{\partial T_i}{\partial x}$$

as computed through equation 4 may be considered an additional heat loss term in equation 1.

FIG. 13 illustrates an example thermal model. FIG. 14 illustrates an example acoustic source model showing time averaged intensity against eyelid, water, FSA, and air.

The experiments with an air gap lens may show that the air gap lens may be a good protective measure. As shown in FIG. 15, the eyelid tissue may be heated with the characteristic shark fin profile. The heating in the cornea may occur after a short delay and may not reach its peak temperature until after 3 minutes of treatment time, despite the transducer source having been extinguished at 2.5 minutes.

FIG. 15 illustrates a chart of temperature rise against time for the external transducer 74 configuration. For an example experiment simulation, a 4.5° C. rise in temperature was shown in less than three minutes. For the example experiment simulation, no ultrasound energy penetration was shown through air gap 72. There may be a small heat diffusion into cornea, such as 0.5° C. Low power may be used for heating with a PZT transducer 74.

FIG. 15 demonstrates the safety of an air gap lens for ultrasound treatment in the cornea. The heating profiles of the eyelid and cornea are distinctly different; instead of the sudden ramp-up due to an applied heat source, the cornea gradually begins to warm up due to diffusion through the lens. There is a thermal propagation delay of several seconds in between the temperature rise of the red eyelid curve and the blue corneal curve that illustrates this. In addition, the peak temperature attained by the cornea occurs after the ultrasound source had been turned off, indicating that the cause of its heating was diffusion of the heat deposited in the eyelid.

FIG. 16 illustrates a contact lens area proximate to FSA and ultrasound gel. FIG. 17 illustrates a chart of temperature rise against time for FSA.

Heat diffusion through the air gap of the lens may be relatively minimal. See for example, the air gap given the chart in FIG. 15 showing that no ultrasound may be propagated through to the inner lens. In some instances, a temperature rise in the cornea may be 0.5° C., which is within even the conservative safety limits of 6° C.

For source amplitudes of 30 and 35 V, temperature rises of 4.5° may be observed in the eyelid, suitable to raise the inner tarsal plate from body temperature to the desired melting point of abnormal meibum. Naturally, the larger source amplitude produced this target temperature rise faster; hence the amplitude or duty cycle of the source may be modified in the future to obtain the temperature rise in a desirable time limit—preferably one that minimizes the corneal temperature rise due to diffusion.

FIG. 18 illustrates example vacuum molded PVDF to construct sub-tarsal devices. The transducer may be shaped to complement the eye surface. The transducer may be secured to lens and then electronics may be enclosed with air backing.

To produce a piezo film that will fit well into the tarsal surface, a vacuum mould may be a viable method to shape the film. Depicted in FIG. 18(a)-(e) with the PVDF film shown, and the vacuum mould (made from porous metal or plastic) shown with black circles. First a PVDF layer with deposited electrodes may be mounted overtop a vacuum-forming mould with a cavity (a), and a vacuum may be applied to the layer to mould it, forming the PVDF to the desired shape (b). Next, with the vacuum still applied, a lead may be epoxied to the concave side of the layer with conductive epoxy (c). After curing, the concave PVDF may be filled with non-conductive epoxy (brown) for structural strength (d). The film may be then removed, the excess material may be cut from its outer radius, and the second lead may be epoxied to the convex side of the film with conductive epoxy (e). This transducer may be mounted to the inner face of a contact lens. The electrical connections may be soldered, and then enclosed inside an air gap (f).

FIG. 19 illustrates example prototypes for PZT internal transducers for embedding within air gap contact lens. PZT has a high-electrical to acoustic energy transfer on transmission. Epoxy and FSA may attenuate at around 8 dB/mm. The thickness may be minimized. Two example PZT prototypes are shown for illustrative purposes, with different attenuations due to epoxy and the lens. One example includes a small transducer with minimal epoxy fitted inside a lens. Another example includes a larger transducer epoxied to the lens with its tip removed. The larger the transducer the more difficult it may be to ensure an air gap between the inner and outer lens. The prototypes may be used to heat the tarsal plate by 5° C. for example. An air gap may be integral to lens design.

Embodiments described herein may use an ultrasound hyperthermia device contained within a contact lens with an internal air gap. The piezoelectric film may produce an acoustic wave to warm the tarsal plate, targeting the meibomian glands, and is also air-backed in order to avoid the propagation of ultrasonic energy backwards into the cornea. A prototype of this device may be built with contact lens materials in a planar geometry to test its feasibility. Ex vivo experiments with porcine eyelid and cornea tissue may be performed with the device with low amplitudes (30-35V) and a relatively low duty cycle (25%).

A temperature rise of 4.5° C. in the eyelid may be achievable in a short timeframe.

A vacuum mould may be used to form a spheroidal concavity in a PVDF layer. This film may then be fixed between two commercial contact lenses with an air gap providing an air backing to the transducer, with the electrical connections inside this gap. Such a device may be suitable for in vivo preclinical experiments.

To measure the attenuation of FSA and porcine eyelid (which may be used for experiments), samples of known thickness may be placed atop a quartz plate, and the resulting pulse-echo signal may be compared with the signal from the quartz plate without any obstruction. In both cases, the transmission coefficients for the sample, quartz, and water may be accounted for. Since a broad band transducer may be used, the frequency spectra of the signals may be used for comparison, rather than the signals themselves in the time domain. For the frequency range considered, FIGS. 22 and 23 show the attenuation coefficients for porcine eyelid and FSA, respectively.

Embodiments described herein relate to an ultrasonic device for mild clinical hyperthermia of the tarsus is proposed. The design consists of a piezoelectric transducer mounted within a specialized contact lens. An example configuration is shown in FIG. 9.

Figure 22:
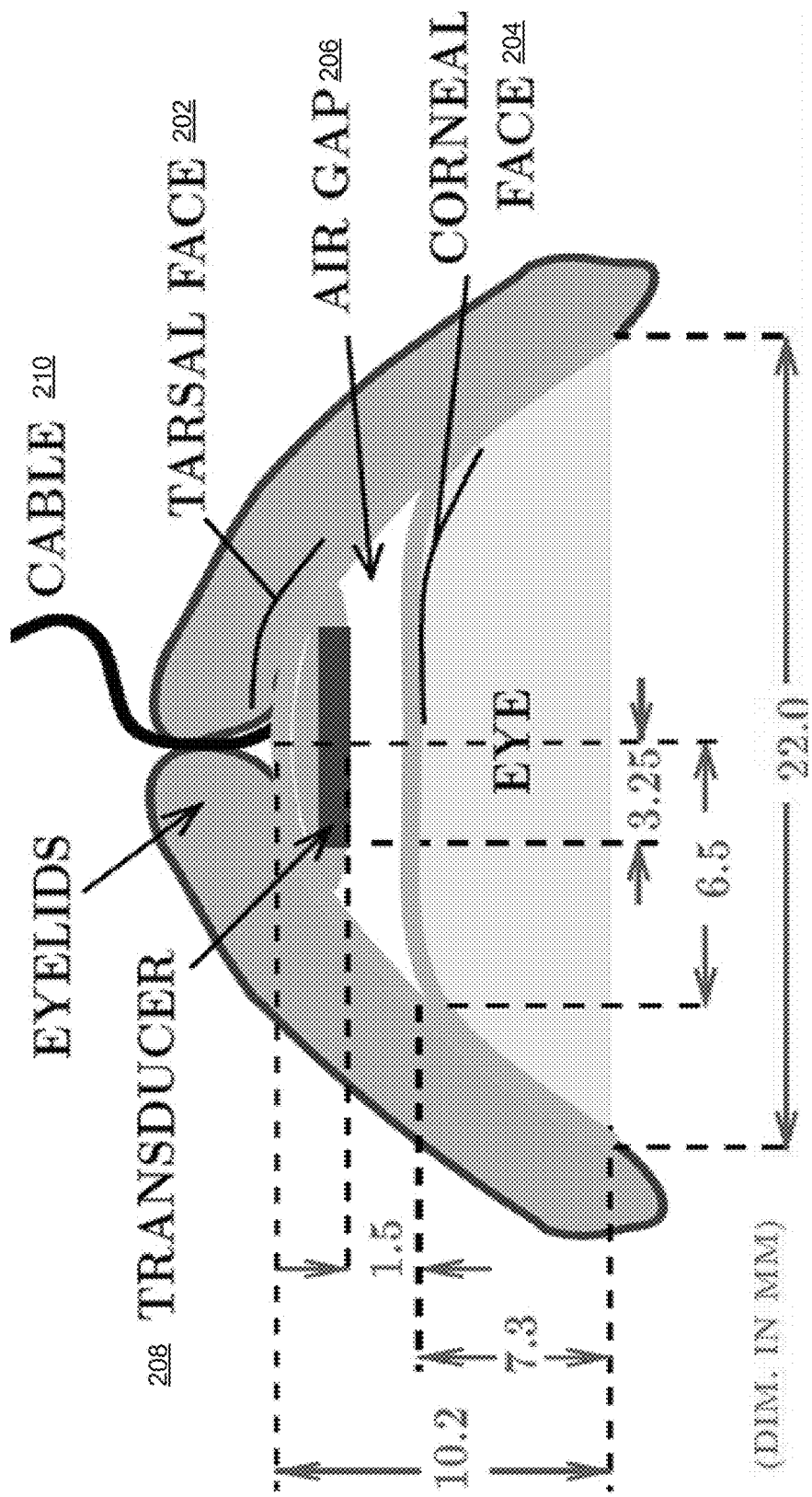
Figure 23:
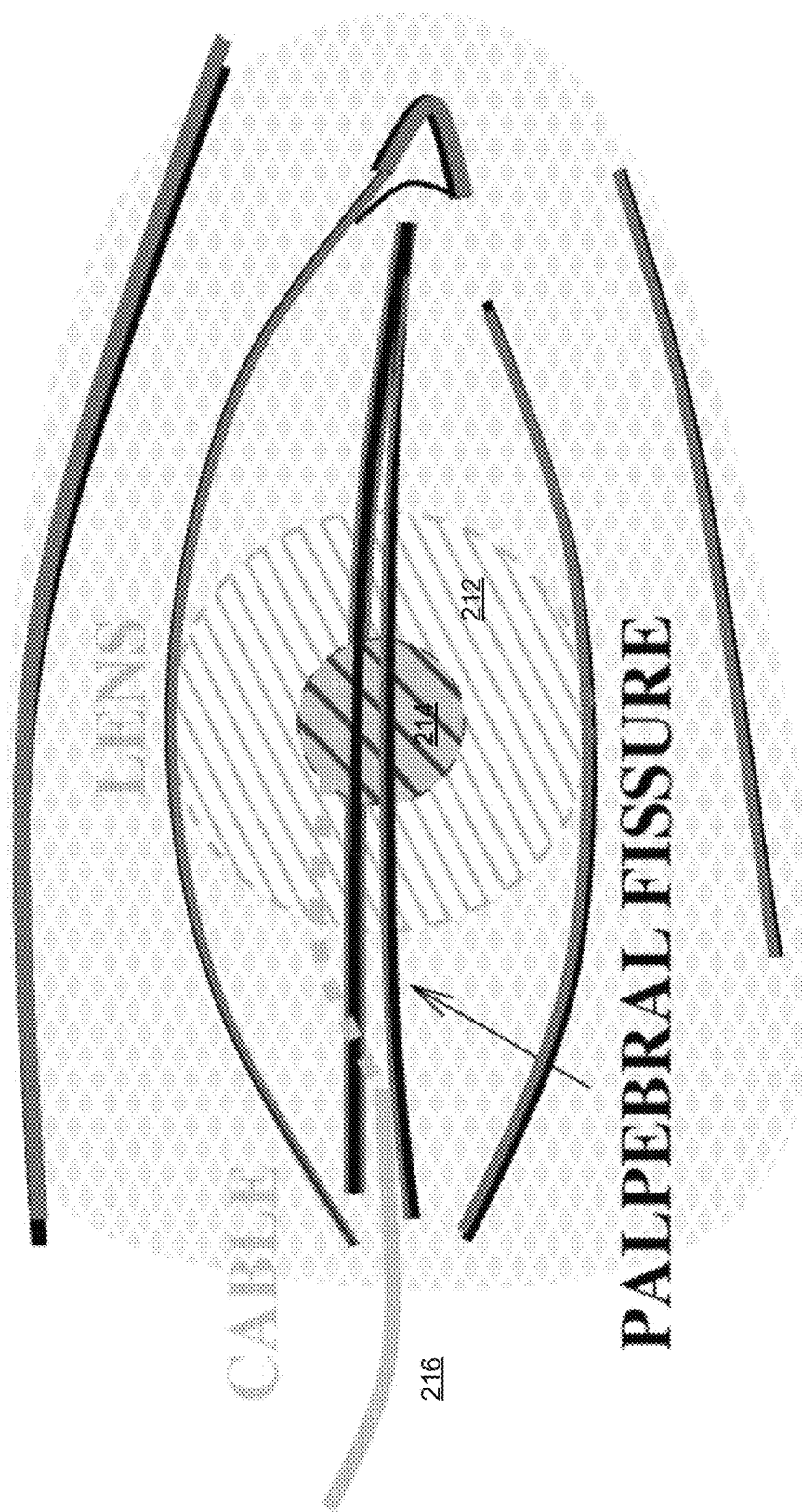

FIG. 22 illustrates another example of an air gap lens according to some embodiments. The air gap lens has lens layers, including a tarsal face 202 and a corneal face 204, that define an air gap 206 or a chamber of air. In this example a transducer 208 is located within the air gap 206 and not in contact with the lens layers. The transducer 208 is coupled to a cable 210 to supply energy for delivering ultrasound. The dimensions noted are illustrative examples only.

The closed air chamber within the lens structure may ensure that there is a built-in air barrier to ultrasound which will provide sufficient acoustic impedance. Wth such a design ultrasound contact gel can be used on the surface of the eyelid or periocular tissue without concern of the gel or any other fluid getting into the air barrier. As ultrasound does not propagate well through gases this design would provide high acoustic impedance and thus shield the eye from ultrasound energy. The different layers of the lens may also comprise an absorptive material to block penetration of ocular tissue by the ultrasound waves. In particular, if the ultrasound is being applied externally through a separate ultrasound probe, then outer surface of the contact lens which abuts the tarsal conjunctiva of the eyelid could be made of an absorptive material or have an absorptive coating hat would uniformly heat and further act to warm the inner eyelid and the meibomian glands.

The air gap lens contains an internal air gap 206 between its inner face mounting the sclera and cornea, and outer face beneath the tarsal conjunctiva. These inner and outer faces are referred to as a tarsal face 202 and a corneal face 204, respectively. The air gap 206 is ensured by fabricating a lens that steeply vaults the cornea at the limbus with several millimeters of clearance, and subsequently securing a second lens that does protrude as steeply from the sclera to the posterior of the first, such that the clearance results in the air gap 206. The vaulting curvature of a lens may be a large-diameter scleral contact lens for patients with abnormally sized corneas, or may be a customized lens. The lens may be fabricated to have different curvatures along the length of the eye, such that the lens abuts the sclera and protrudes outwards at the corneal limbus, vaulting over the cornea and protruding from the base.

The transducer 208 may be mechanically secured to the posterior tarsal face via an epoxy, but may not contact the tarsal lens 202 face. As such, the transducer 208 may be contained inside the air gap 206 with the active face directed outwards towards the tarsus. The air gap provides an air backing to the transducer 208, such that the acoustic impedance mismatch of the transducer 208 material and the air may ensure the acoustic waves do not propagate towards the eye.

Accordingly, an ultrasonic hyperthermia device for the tarsus may include an air gap lens. The air gap 206 within the lens reflects ultrasonic energy towards the tarsal plate, shielding the cornea.

When the lens is placed overtop the sclera, the eyelids may hold the device in place through the mechanical pressure of the orbicularis. The use of a scleral contact lens may also ensure the axial alignment of the transducer 208 with respect to the visual axis of the cornea during treatment. The electrical connections to the active and ground electrodes of the transducer 208 are connected via sub-millimeter diameter coaxial cable, which exits the lens via a milled through-hole that is fitted to the cable 210 diameter and sealed airtight. The cable 10 may exits the eyelids from the palpebral fissure, near the lateral canthus.

During treatment, a continuous wave excitation voltage may be applied across the transducer 208 terminals with a low duty cycle (less than ten percent for example). The acoustic waves may be directed towards the tarsus from the transducer's 208 active face, and reflected away from the cornea by the air backing. The forward-propagating ultrasound may be attenuated by the eyelid tissue, thus depositing thermal energy in the tarsus. Power may be applied to the transducer continuously for a treatment period of 10-15 minutes, as an illustrative example. During this time, the basal temperature of the eyelid may be brought to equilibrium at the elevated target treatment temperature of 41-43 degrees Celsius. During steady state conditions, this temperature may not fluctuate, and the constant elevated temperature liquefies the lipid within the meibomian ducts, allowing it to flow and coat the tear film. After this time, the power may be ceased, allowing the eyelid to return to its base temperature.

Figure 24:
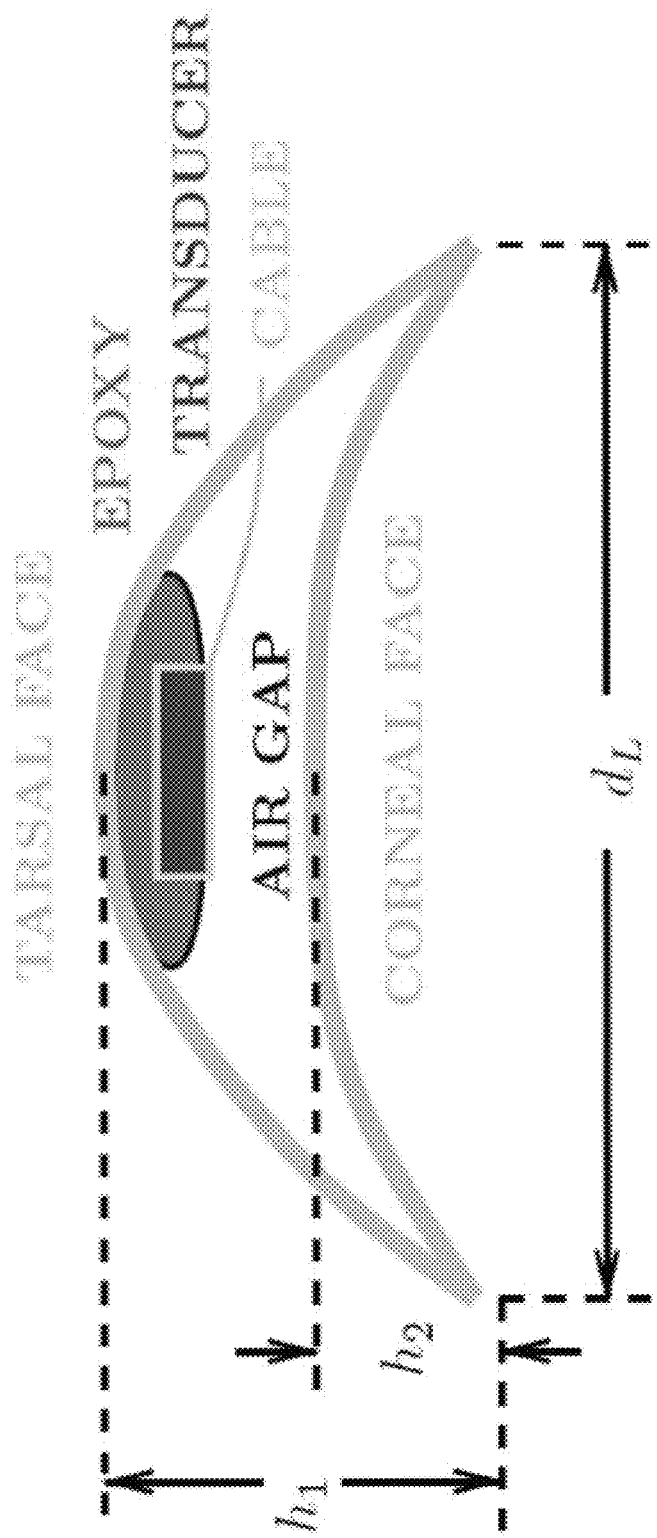
Figure 25:
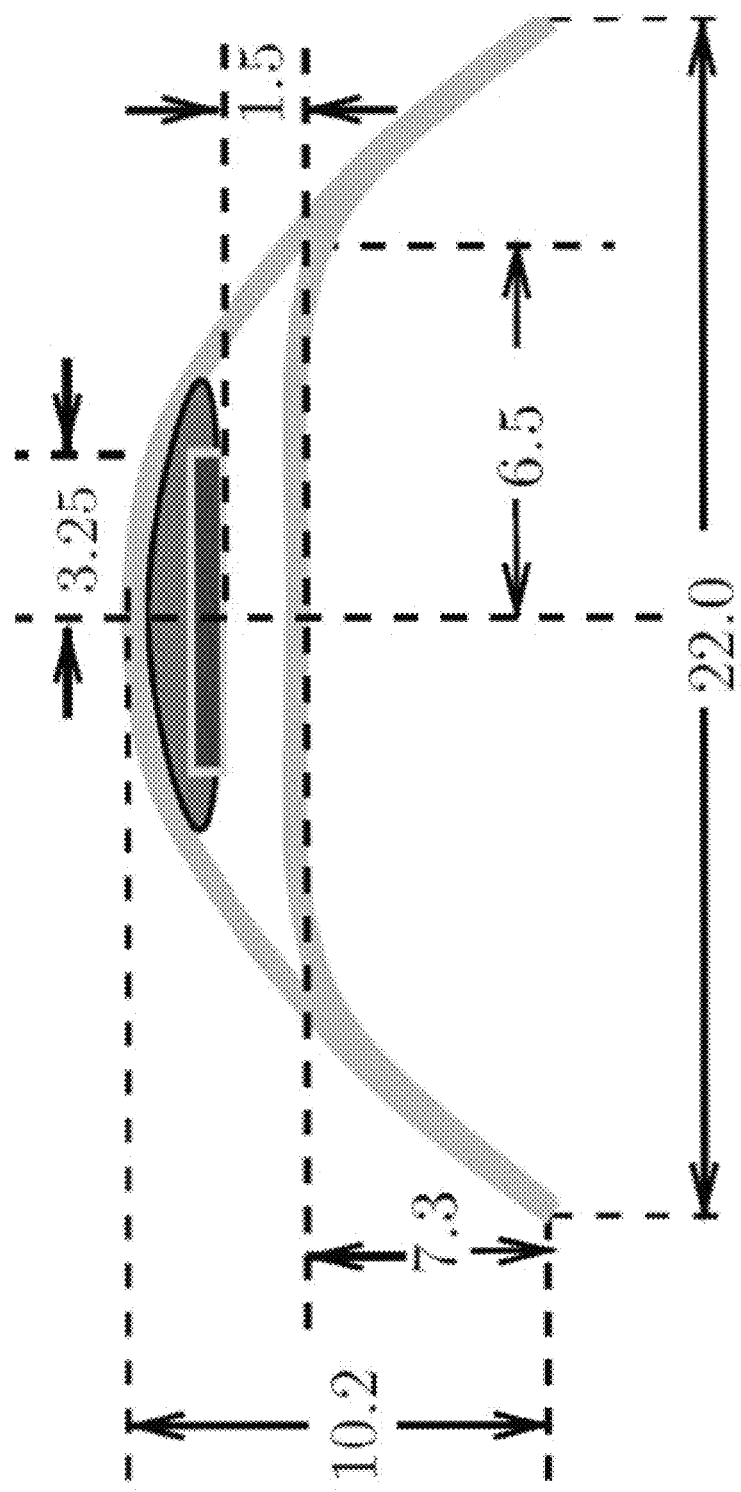

FIG. 23 illustrates a schematic showing the placement of the lens 212 and transducer 214 underneath the eyelids, with the wiring 216 exiting through the palpebral fissure near the lateral canthus. FIGS. 24 and 25 illustrate further example schematics of the air gap lens.

Table 4 provides details on the marginal eyelid composition in order from the anterior to the posterior surfaces.

TABLE 4

| Order | Layer | Thickness (mm) | Tissue |
| --- | --- | --- | --- |
| 1 | Dermis | 0.05 | Dermal |
| 2 | Epidermis | 0.3 | Epidermal |
| 3 | Orbicularis | 0.15-0.65 | Muscle |
| 4 | Tarsal Plate | 1-1.5 | Fibrous |
| 5 | Conjunctiva | | Mucous |

Ultrasound hyperthermia may deliver heat to tissue via the absorption of acoustic waves. For a medium with an acoustic attenuation $\alpha$, the mean heat deposition rate $Q_\alpha$ at a distance z from the source transducer is:

$$\dot{Q}_\alpha = 2\alpha \bar{I} \exp\{-\alpha z\} \quad (5)$$

where $\bar{I}$ is the time-averaged ultrasonic intensity at $z^{20}$. Equation 5 shows the exponential decay of the field intensity with axial distance dependent on $\alpha$.

The attenuation is frequency-dependent, increasing monotonically with frequency as:

$$\alpha(f) = \alpha_0 f^n \quad (6)$$

where the constants $\alpha_b$ and n are tissue properties and $n \approx 1^{22}$. Though the marginal eyelid is only approximately 2 mm thick, it comprises multiple layers of tissue with different compositions and heterogeneous vasculature. The anterior surface is skin, underneath which is found the orbicularis muscle. Beneath this is the tarsal plate, composed of fibrous tissue that provides structural integrity to the eyelid. There may be minimal development of subcutaneous fat, and hence the eyelid is composed of muscle, skin, and fibrous tissue.

The muscle and fibrous regions of the eyelid have extensive arterial blood supply along both the superior and inferior margins, which may motivate the transducer placement. Blood perfusion may a factor in hyperthermia, removing excess heat in tissue with elevated temperatures with respect to the core blood temperature $T_c$. This cooling term for a tissue at temperature T may be modeled by:

$$\dot{Q}_b = w \rho_b c_b (T - T_c) \quad (7)$$

where w is an effective blood perfusion rate, and $\rho_b$ and $c_b$ are the density and specific heat of blood, respectively.

Together with heat diffusion, the terms in equations 5 and 7 yield the bioheat transfer equation for the tissue temperature T as $$\dot{T} = \frac{1}{\rho c} \{ k \nabla^2 T + \dot{Q}_b + \dot{Q}_a \} \quad (8)$$

where p, c and k are the density, specific heat, and thermal conductivity of tissue, respectively. Due to the inherent attenuation in the contact lens and epoxy materials, the ultrasonic field is attenuated before reaching the tarsus. As such, the epoxy and lens increase in temperature during treatment. The heat produced within the lens is conducted towards the tissue via the gradient $\nabla^2 T$ in addition to $\dot{Q}_\alpha$.

The blood perfusion in equation 7 may be a factor motivating the sub-tarsal transducer placement due to the physiology of the eyelid. The marginal eyelid is only approximately 2 mm thick, but comprises multiple layers of tissue with different compositions and heterogeneous vasculature. The anterior surface is skin, underneath which is found the orbicularis muscle. Beneath this is the tarsal plate, composed of fibrous tissue that provides structural integrity to the eyelid.

Blood perfusion from the subcutaneous arterial supply limits the temperature rise that can be achieved during thermal equilibrium from external heating, since the excess heat is quickly removed.

A study of the temperature difference between anterior and posterior surfaces of the eyelid during hyperthermia has been shown to be around 2 degrees Celsius, implying that the desired equilibrium temperature of 41 Celsius in the tarsus brings the anterior eyelid surface very close to the threshold of thermal damage. Heating directly from the conjunctival surface tarsal plate may mitigate this risk.

Since the Meibomian glands are within approximately 1 mm of the tarsal lens face, a high frequency may be used in order to optimally deposit acoustic power at the tarsus, as seen from equation 6. Combining an intensity loss with the inherent attenuation of the epoxy and lens material, a high frequency transducer may deposit the majority of its energy within the tarsus.

FIG. 26 illustrates a graph from measured attenuation of porcine eyelid with a broadband 15 MHz transducer for an illustrative experiement. Histogram samples were taken from 126 evenly-spaced points over an 18 mm lateral sweep of the 4.0 plus/minus 0.5 thick marginal eyelid. The standard deviation about the mean is shown in the dashed lines.

Due to the inherent attenuation in contact lens and epoxy materials, the ultrasonic field is attenuated before reaching the tarsus and that heat is produced in the lens itself. The initial heating within the eyelid has two components: conductive and ultrasonic.

Intense heating in the cornea may cause corneal deformation, affecting or impairing vision. The cornea and humour have no vasculature, and may be more susceptible to thermal gradients arising in ultrasound fields without direct blood perfusion. A concern is to establish a safe limit of clinical temperature rise in the cornea. A conservative limit may be 40 degrees Celsius. This may correspond to a maximum 6 degrees Celsius rise, given an example resting ocular surface temperatures. The eyelid has one of the most dense vascular anastamoses in the body, removing heat as in equation 7 and decreasing the risk of thermal burn. Furthermore, the threshold of pain and thermal damage at prolonged exposure in tissue is 45 celsius, which may be beyond the target range of the device. A measurement device may monitor temperatures and trigger automatic shut-off, automatic temperature decrease, and other safety mechanisms. Since uncomfortable temperatures can be reported by a patient during treatment, this upper bound may be considered relatively benign.

The internal air gap may serve two purposes for the safety of the device. First, it may provide an air backing layer to the transducer, thereby reflecting essentially all of the acoustic energy along the forward axis due to the impedance mismatch between the piezoelectric material and air. This may minimize the ultrasonic pressure field propagated through the scleral surface into the cornea: any pressure wave must be carried as a surface wave through the lens material, removing the risk that a direct, high intensity field would cause unwanted heating.

The air gap further acts as an insulating layer between the tarsal and corneal faces; when the epoxy binding the transducer to the tarsal face posterior heats due to its acoustic absorbance, heat cannot be directly conducted between the two lens faces. Heat at the tarsal face must diffuse through the connecting periphery of the lenses overtop the sclera before reaching the cornea, since the air gap is largest overtop the corneal apex. The convective mechanism of heat transfer through stationary air is orders of magnitude lower than direct conduction, minimizing the amount of heat directly conveyed to the cornea.

Embodiments have been implemented as experimental methods, as illustrative, non-limiting examples.

A prototype of the hyperthermia device was constructed from two large scleral lenses composed of fluorosilicone acrylate. The base diameters of both were 22 mm, lathed with optical precision. The combined height of the two scelaral lenses mounted atop each other, approximately coaligned, was 10.19 plus/minus 0.01 mm, leaving over 2 mm of clearance between the posterior of the tarsal face and the anterior of the corneal face. The contact lenses employed in this prototype have identical or similar base diameters and similar scleral mounting curves, and hence when the tarsal lens is mounted atop the corneal lens, the point of contact between them is near the corneal limbus, illustrated in FIG. 22, FIG. 24, FIG. 25. This point is termed the limbal point and was measured as 6.5 plus/minus 0.1 mm, with slight variations around the circumference.

Lens schematic and dimensions are examples only, and shows the air gap size and limbal mounting radius. Dimensions in millimeters are shown, but not drawn to scale.

A PZT piston transducer with radius 3.25 plus/minus 0.01 mm was milled in-house with a diamond end mill from 208 plus/minus 2 mm thick piezoceramic sheets precoated with gold electrodes. Leads from a 440 mm coaxial cable were soldered with 350 mm solder spheres at the transducer periphery for minimal interference with the beam. The measured centre frequency was 11 MHz.

To attach the transducer to the posterior tarsal face, a through-hole was lathed near the apex of the tarsal lens and the transducer cable was fed through, allowing the piston to rest inside the concave region in the lens posterior, with approximately one mm of clearance. While the lens was oriented downwards, the transducer was secured to the posterior of the tarsal lens by the injection of low viscosity epoxy into the clearance space between the transducer and lens via a one ml syringe and fine gauge needle. Care was taken to fill the concavity steadily to minimize the formation of bubbles within the epoxy solution, and avoid any epoxy from contacting the back face of the transducer. The epoxy was then cured at 45 degrees Celsius for several hours. The through-hole was subsequently sealed airtight with epoxy using the same technique and similarly cured. Finally, the two lenses were epoxied together to form a single lens with an air gap. This is an example construction for the experiment and there may be multiple variations. The final size of the air gap may be between 1-1.5 mm at the apex of the corneal face, increasing with radial distance.

The properties of the lens were measured using a bulk cylindrical mass of fluorosilicone acrylate. The speed of sound and attenuation at 11 MHz were computed using time of flight measurements from reflections off of a quartz plate. The attenuation shown for the epoxy was measured at 30 MHz, and hence is substantially higher than expected at 11 MHz; if a linear frequency dependence is assumed in equation 6, the attenuation at 11 MHz would be a third of this value at approximately 5 dB/mm.

To evaluate the ability of the internal air gap to reflect ultrasonic energy away from the cornea, the acoustic field intensity at the posterior of the device's corneal face was measured with respect to the field at the anterior tarsal face. As in FIG. 27, the lens transducer was held in a water tank with a 10.5 MHz broadband composite transducer, fabricated in-house, used as a receiver. The receiver was mounted on a micrometer stage with three degrees of freedom such that the receiver axis was approximately coaligned with the lens transducer axis, and could be swept across the lens face in the vertical and lateral directions. Two experiments were conducted: first, as in FIG. 27 for orientation the device was oriented with the tarsal face towards the receiver; and second, as in orientation, with the active face directed downwards to the rubber absorber, and corneal face exposed to the receiver. The same vertical distance was maintained between the apex of both lens faces and the receiver (corresponding to a time delay of 13 µs to reach the receiver). To excite the device transducer, a 5 cycle 11 MHz pulse was generated using an arbitrary waveform generator and amplified by a radiofrequency power amplifier. This pulse was then applied across the transducer terminals with a delay of 10 ms between excitations. A short pulse may avoid producing a standing wave between the receiver and lens. The signal measured by the receiver was amplified, digitized by an oscilloscope and stored on a computer.

To correctly position the receiver over the lens apex, pulse-echo measurements from the receiver were used, knowing that the time delay was a minimum at tarsal face's highest point, and was a maximum at the corneal face's lowest point.

The time-of-flight measurements also yielded the distance from the transducer. Once positioned vertically over the corneal face, the pulse-echo measurements were ceased, and receiver was kept at a constant height and swept laterally across the lens to measure the ultrasonic intensity of the device transducer's excitation.

The measured intensities of the field at the posterior corneal lens were then compared with measurements of the intensity at the anterior tarsal face. The intensities of the A-lines measured from the tarsal face varied little with vertical distance in the 10-15 µs region, which is well within the nearfield distance of $a^2f/1500$ approximately 7.75 cm.

The hyperthermia device was tested on a porcine subject in vivo to demonstrate its clinical potential by measuring the temperature rise induced in both the eyelid and cornea.

Pig models are routinely used as ocular models in preclinical studies due to the relative similarity between human and porcine corneal tissue. The porcine cornea is 800 µs thick compared to the human thickness 500 µs, and has nearly identical acoustic absorption and celerity. The ultrasonic attenuation and celerity of the scleras of both species have also been demonstrated to be similar.

To measure the induced temperature rise in porcine tissue, type E thermocouples were selected with a wire diameter of 130 plus/minus 1 µm. The wires were coated in Teflon insulation of thickness 85 plus/minus 1 µm, and were sealed in a Teflon sheath of thickness 59 plus/minus 3 µm for a total outer diameter of 410 plus/minus 10 µm. The thermocouple junctions, however, were bare: the insulation and sheath were peeled back to expose the wire for 1.5 plus/minus 0.1 mm and 2.1 plus/minus 0.1 mm from the junction tip for the thermocouples used in the humour and eyelid, respectively.

A 22 kg male Yorkshire pig was sedated with a 1.2 ml cocktail of Dexdomitor/Atropine and anaesthetized with 2% inhalant Isoflurane. Its core temperature was measured with a rectal thermometer as 36.75 plus/minus 0.05 degrees Celsius. The pig was placed on its right ventral side, exposing the left eye.

As shown in FIG. 28 the in-lens transducer device was placed overtop the eye such that the visual axis of the cornea and the transducer axis were approximately coaligned. The eyelids were pulled overtop the tarsal face of the device and secured in place with medical tape, allowing the transducer cable to exit the palpebral fissure near the lateral canthus. Two thermocouples were embedded in the pig tissue: one within the aqueous humour, and the other in the superior eyelid, 2-3 mm above the margin. Both thermocouples were embedded by placing them within the cannula of a 19 gauge needle, and subsequently retracting the needle to leave the thermojunction in place.

To produce hyperthermia, an 11 MHz waveform with 10% duty cycle and 18.12 µs pulse width (corresponding to 200 cycles) was generated with a waveform generator and amplified by a radiofrequency power amplifier and applied across the transducer terminals. Sonication occurred until the eyelid tissue reached steady state conditions at an elevated temperature, at which point the power was ceased and the tissue was left to return to equilibrium at basal temperature. The temperatures measured by the thermocouples throughout sonication and cooling were recorded continuously, and digitized with a cold-junction reference with a sampling period of 100 ms. The digital values were stored on a portable computer in the operating room.

The thermocouples were embedded into the porcine eyelid and anterior chamber in two sets of hyperthermia experiments. In the first set, the thermocouple in the eyelid was embedded in the eyelid at a depth of 1-2 mm from the dermis in a perpendicular orientation relative to the transducer axis, as in (A) of the FIG. 28 inset. Four hyperthermia trials were conducted on this set; in each, sonication was applied for 15 minutes. At approximately 150 minutes after the first sonication trial, the eyelid thermocouple was removed from the eyelid tissue and re-embedded in the superior eyelid, again several millimeters above the margin at a depth of 1-2 mm, displaced laterally from the previous puncture site by several millimeters. In this set, however, the thermojunction orientation was parallel relative to the transducer axis, as in (B) of the inset of FIG. 28. With this orientation, three trials were conducted, lasting 9, 15, and 15 minutes, respectively. Shortly after the final trial, the pig died without intervention from the effects of anaesthesia. The thermocouple in the anterior chamber was located approximated 1 mm behind the cornea and kept in the same location during both experiment sets.

Hereafter, the two sets of trials will be referred to as perpendicular and parallel, respectively. These two orientations were chosen in order to identify evidence of temperature artifacts induced by the thermocouples in the ultrasound field, since it has been established that orientation is a factor in the magnitude of the artifact.

The computed field intensities at both the tarsal and corneal faces in the near-field of the lens transducer are shown in FIGS. 29*a* and 29*b*, respectively. To calculate the relative power intensity, the maximum A-line amplitude measured in the near-field of the tarsal face has been used as a reference; the ratio to this of A-line amplitude peaks at each lateral position in both the tarsal and corneal near-field have been used to approximate the relative intensity loss using the ratio to the maximum value measured.

The tarsal intensity in FIG. 29*a* is constant over the piston transducer face (a=3.25 mm). In subplot FIG. 29*b*, there may be evidence of pulse transmission near the limbal contact region of the lens, at radii greater than 6 mm. The attenuation of this pulse may be greater than 13 dB. The transmitted power through the corneal face is not constant along its circumference; the values shown in FIG. 29*b* are a maximum.

FIG. 29*a* illustrates the relative field intensity of the lens transducer face in the near-field. The dropoff occurs shortly after 4 mm in the radial direction. FIG. 29*b* illustrates relative radial intensity at the posterior of the corneal face of the lens transducer. The receiver was positioned at a constant height above the lens 13.0 plus/minus 0.1 µs away in time) and swept across the lens radially from the epicentre. The intensities are relative to the maximum intensity measured at the tarsal face.

To show the general heating profiles over time, FIG. 30*a* is a plot of the absolute temperature of the humour and eyelid during the two sets of trials. Four hyperthermia trials were performed with the eyelid thermocouple in the perpendicular orientation, shown to the left of the vertical dashed line in FIG. 30*a*. The three heating curves to the right show the temperature rise induced with the eyelid thermocouple in the parallel orientation.

There are several observations to make concerning this plot: (a) The basal temperature of the tissue (equilibrium temperature during periods of no sonication) decreases over time for a given orientation. This is shown more clearly in FIG. 30*b*, where the equilibrium temperatures have been computed by averaging 100 seconds of the recorded temperature before each hyperthermia cycle began; (b) The temperature difference induced in each trial increases monotonically within the two sets; (c) There is some degree of biological noise in the system, culminating in fluctuations in temperature of 0.25 degree Celsius—of far larger magnitude than the electrical noise in the thermocouples. These mildly periodic fluctuations were observed even in equilibrium, and decreased in frequency and magnitude once the pig was artificially ventilated at 45 min after the first sonication. The fluctuations are present in both the eyelid and humour thermocouple data.

FIG. 30a illustrates heating curves of the humour and eyelid in each hyperthermia trial over elapsed time from the first sonication. FIG. 30b illustrates basal temperature of the eyelid and humour over time, as computed from 100 s of equilibrium temperatures when no ultrasound was applied to the tissue. Error bars show the standard deviation about the mean.

Figure 31A:
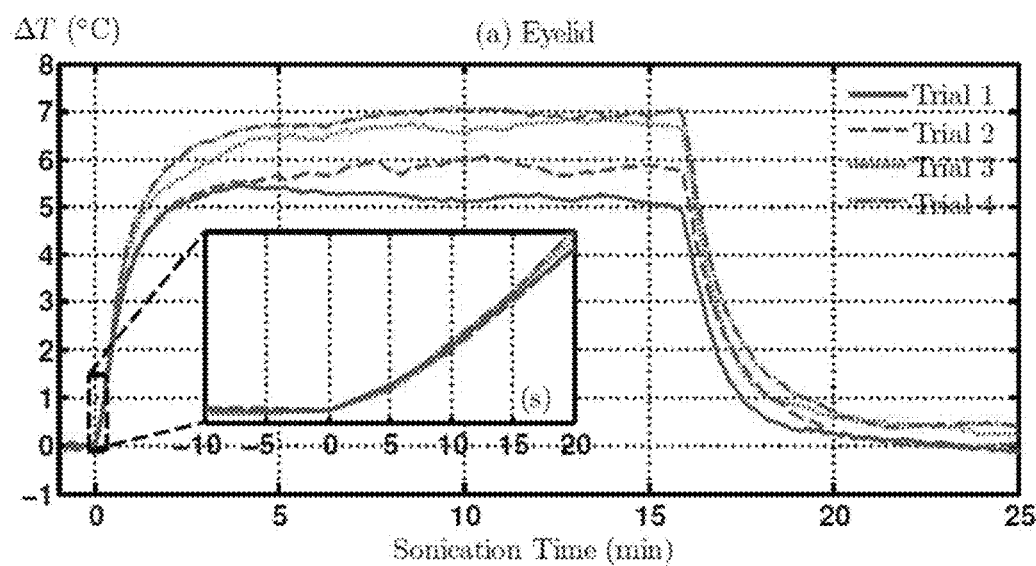
Figure 31B:
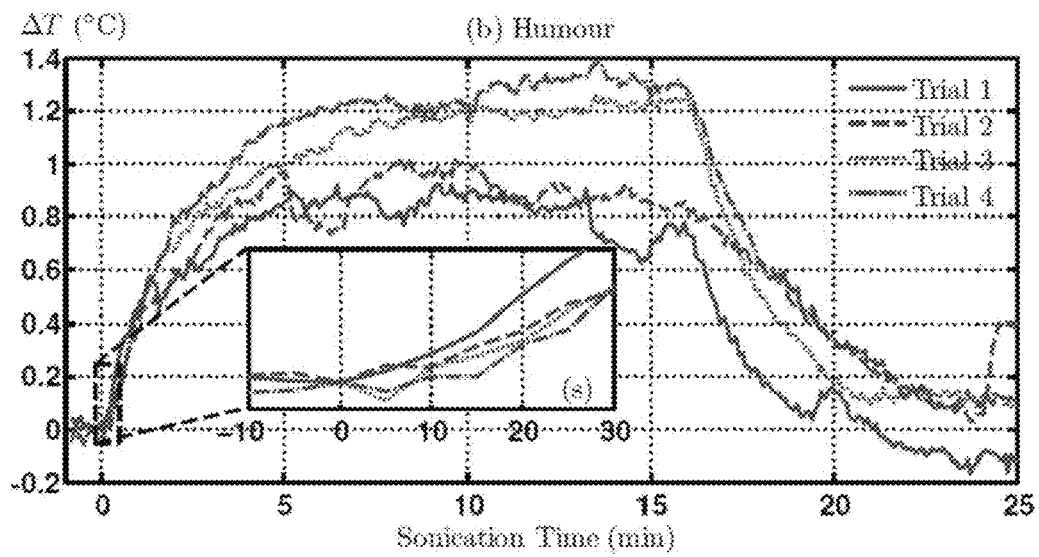
Figure 32A:
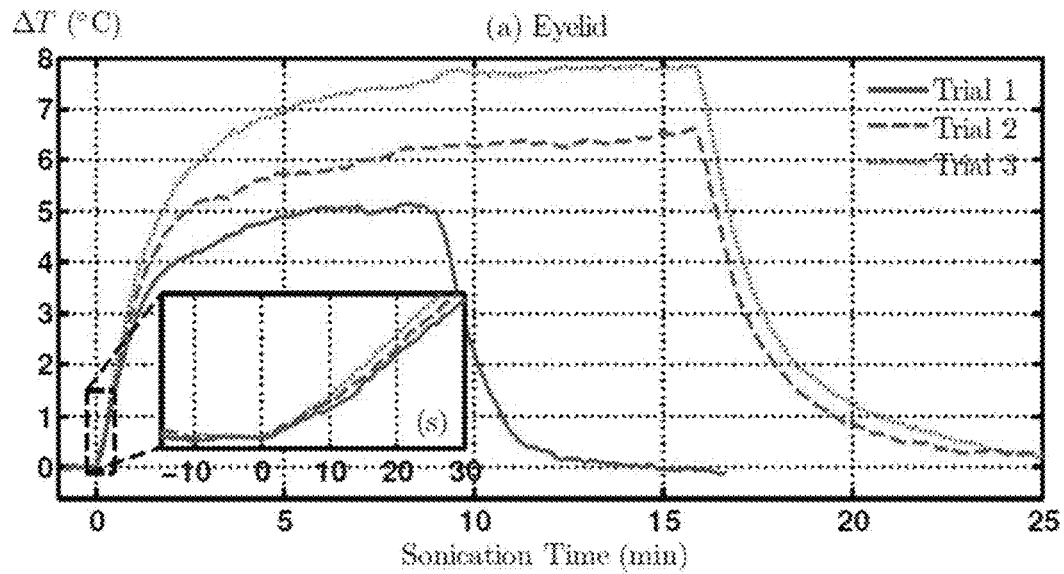
Figure 32B:
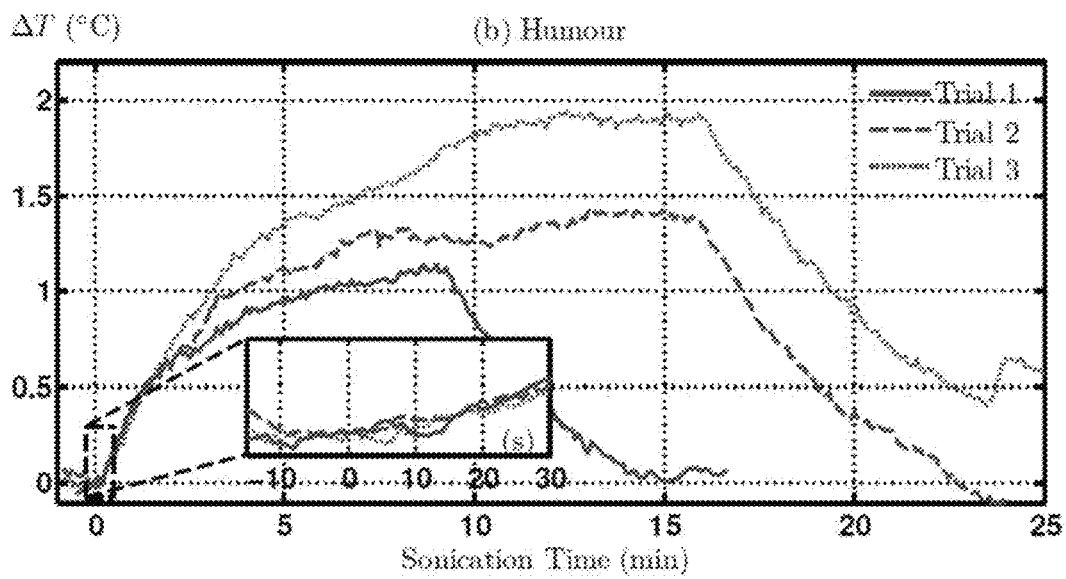

The relative temperature rises $\Delta T$ over time for each trial have been superimposed in FIGS. 30a and 30b and FIGS. 31a and 31b which may demonstrate the degree and rate of hyperthermia. In both of these figures, FIGS. 30a and 31a show the measured rise in the eyelid, and FIGS. 31a and 31b show that in the humour. Both of these plots show the typical exponential rise and fall, with steady-state rise in the eyelid in the range of 5-8 Celsius. In the perpendicular orientation, the temperature rise in the cornea remains under 1.5 degree Celsius for all trials. For the parallel case, the corneal temperature rise did not exceed 2 degree Celsius. In the insets of these figures, a magnification of the temperature rise after initial sonication is shown, with the scale in seconds. There is little to no thermal delay in either the eyelid or humour heating profiles: once ultrasonic power is applied, the temperature rises almost linearly, as is expected from equation 5 before the effects of blood perfusion and diffusion become pronounced from greater $\Delta T$. This shows that ultrasonic energy reaches the humour as well as the cornea, however the magnitude of the temperature rise achieved in the humour is less than a quarter of that in the eyelid.

Figure 33A:
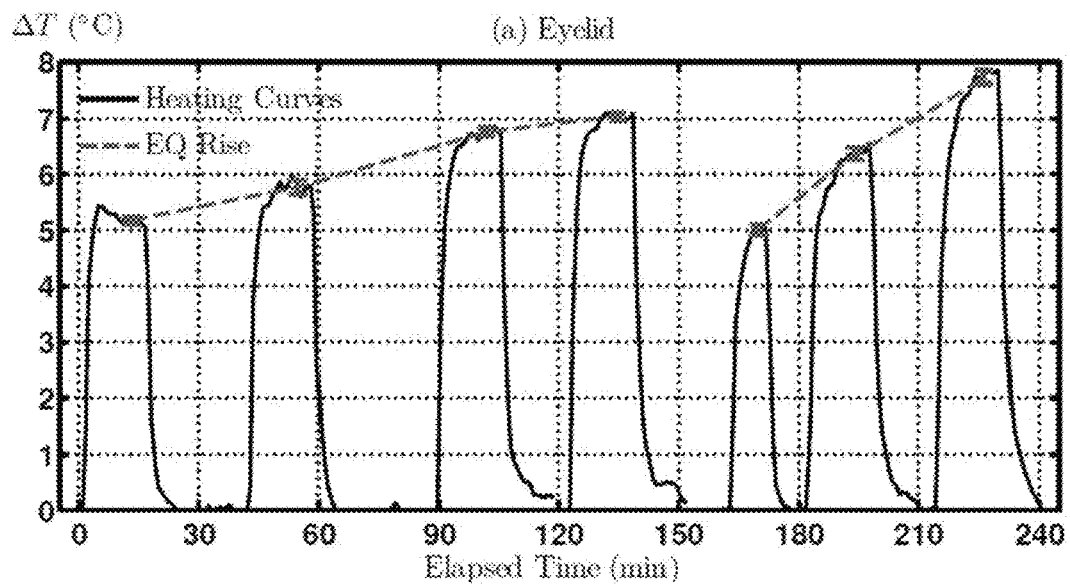
Figure 33B:
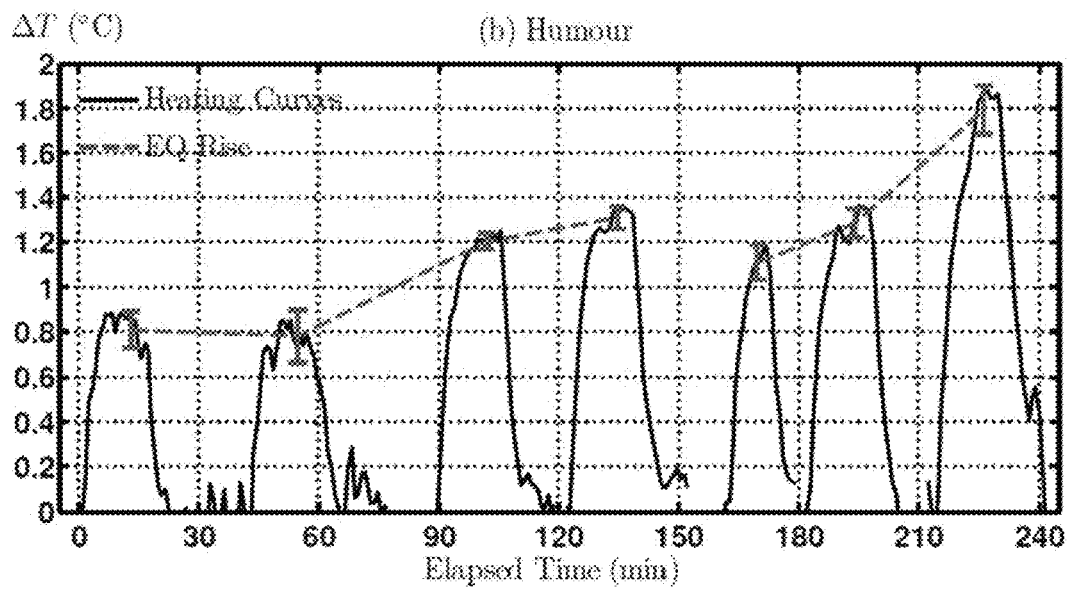

To examine the nature of the increasing temperature rise with time, in FIGS. 33a and 33b the temperature rise in the eyelid is plotted against the elapsed time since the first sonication.

Subplots FIGS. 33a and 33b show the steady-state $\Delta T$ reached for the eyelid and cornea, respectively. The four leftmost curves in both subplots show the rise in the perpendicular thermocouple orientation, and the three rightmost curves show the parallel orientation.

The mean values for $\Delta T$ were computed from the latter ½ of the heating curve before sonication ceased, and the error bars show the standard deviation about the mean for this value. In both experiment sets in FIG. 33a, there is a linear increase in $\Delta T$ in the eyelid with time, however the increase is not monotonic with elapsed experiment time: once the thermocouple was removed from the orbicularis and again embedded in a different position, the temperature gain was reduced to 5 degree Celsius—nearly the elevation obtained in the first trial for the perpendicular orientation. Furthermore, the slope of the equilibrium temperature line in FIG. 33a is approximately half that of FIG. 33b the increase in $\Delta T$ occurs far faster than before.

The $\Delta T$ curves for the humour plotted in FIG. 33b show similar trends with time, but there is a notable difference in that the drop in $\Delta T$ between the perpendicular and parallel sets of trials is far less pronounced. Unlike the eyelid in subplot FIG. 33a, the humour $\Delta T$ for the first parallel experiment does not return to lower value similar in magnitude to the first trial of the perpendicular experiment. Though the temperature rise is lesser, it is comparable to the values measured in the two prior perpendicular trials. Furthermore, it should be noted that the first parallel trial was conduced for only 9 minutes, while the other trials were conducted for over 15 minutes. Hence, the steady state rise for the first parallel trial is an underestimate, though since steady state conditions appear to be reached shortly after 5 minutes of sonication in all trials, this is likely a minor deviation.

FIGS. 33a and 33b illustrate temperature rise over elapsed time since the initial sonication, measured in the FIG. 33a eyelid and FIG. 33b aqueous humour. The heating profiles in the unbroken, black lines show the rises from initial equilibrium temperatures, while the red dashed line shows the equlibrium temperatures, computed from the mean of the latter ½ of the heating curve, when steady-state was reached. Error bars show the standard deviation about this mean value. Note the scale difference in the two subplots.

Embodiments described herein may measure temperature during ultrasound hyperthermia with embedded thermocouples. When a pressure wave impinges upon a bare thermocouple, the viscous shear forces acting between the wire and the medium produce local heating at the junction may cause a temperature artifact and yielding a measurement greater than if the thermocouple were absent. Calculations may automatically adjust to correct this artifact. The magnitude of this artifact depends on several factors: the orientation of the wire with respect to the wave propagation direction, the wire diameter, and the presence of insulating coatings that attenuate the ultrasonic field. Embodiments may minimize the wire diameter with respect to the field wavelength, using only unsheathed wires, and orienting the wires in the direction of wave propagation.

There are several telltale signs of artifacts in the heating curves: the moment sonication begins, an initial temperature jump may occur within the first few hundres milliseconds. When sonication ceases, the recorded temperature drops suddenly by $-T_0$ before continuing to decrease exponentially, allowing $T_0$ to be estimated by backwards extrapolation. The magnitude of $T_0$ is reported to be as large as 1 degree Celsius in porcine muscle just below the skin for 18-30 kg animals, as well as for thermocouples in polyurethane-coated catheters in humans.

The sudden rise and fall by $T_0$ was not observed in any of the trials in either orientation in the present work. Since the thermocouple digitizer had a sampling period of 100 ms, this is a sufficient resolution to detect a rapid change within several hundred milliseconds. There was also no observed systematic difference in temperature rise introduced by the thermocouple orientation, which would have been expected if the artifact were significant. It is thought likely that any artifacts, if present, were negligible in our experiments for three example reasons: the thermocouples used had bare wire thermojunctions in order to avoid the large artefacts previously reported with Teflon sheathing; while most work examining the effect of viscous heating has been down for focused beams, the configuration of interest is and diffuse due to the convex geometry of the lens and piston transducer; hence the acoustic wave impinging upon the thermocouple is of a lesser intensity than previously considered in literature.

Attenuation of epoxy (~5 dB/mm) in combination with the high attenuation of porcine eyelid (~3 dB/mm) at 11 MHz further reduces the intensity. As a loss of 8 dB after 1 mm of the tarsus corresponds to only 40% of the energy remaining as a propagating wave.

To investigate the increase in temperature rise seen in FIGS. 33a and 33b, the effective blood perfusion was calculated for each trial. From equation 8, in steady state conditions before sonication ceases, T=0 and $\nabla^2 T$ is assumed to be small once thermal equilibrium has been reached. Hence the solution of T once the ultrasonic power is turned off is an exponential decay with a known form from equation 7 as $$T = T_c + (T_i - T_c)\exp\left\{-w\frac{p_b c_b}{pc}t\right\} \quad (9)$$

where $T_i$ is the tissue temperature when the power ceases $T_i - T_c = \Delta T$. Hence w may be determined from a least-squares regression of a plot of $T-T_c$ against time. This method provides an overestimate of the blood perfusion, particularly in the eyelid due to its relatively large surface area per mass, since heat exchange with ambient air contributes to the cooling. This term has an identical form to equation 7, however, the coefficient of heat transfer with static air is generally small.

The effective perfusion was determined in this manner for temperature measurements in the eyelid, using the equilibrium temperature before each trial as $T_c$. Only the temperature data from the eyelid thermocouple were considered, since the cornea and aqueous humour have no vasculature, and are cooled by heat diffusion alone. Sample plots of $T-T_c$ over relaxation time to demonstrate the fit to the exponential decay are shown in FIGS. 34a and 34b. To estimate the uncertainty in this numerical method, a moving window of 20 s duration was used to compute the slope, with starting times in the range of 10 to 50 seconds after sonication ceased. The final perfusion value was then determined from a least-squares regression and averaged over all computations with coefficients of determination $r^2$ greater than 0.995. Thus the uncertainty was estimated using the standard deviation about the mean perfusion value.

Table 5 may illustrate example profusion rates for the eyelid with thermocouple for use in FIGS. 34 a and b.

TABLE 5

| Trial | w (ml/min/100 g) |
|---|---|
| Perp. | |
| 1 | 89 ± 2 |
| 2 | 75 ± 1 |
| 3 | 80 ± 3 |
| 4 | 69 ± 2 |
| Par. | |
| 1 | 81 ± 2 |
| 2 | 57 ± 4 |
| 3 | 51 ± 2 |

In computing w the numerical values for the biological parameters were: p=1090 kg/m³, c=3530 J/kg/K, $p_b$=1060 kg/m³, and $c_b$=3900 J/kg/K. Effective perfusion values differ greatly between different tissues.

Example perfusion rates of have been plotted over elapsed time since puncturing the eyelid in FIG. 35 to examine their time dependence. The bottom x-axis (black) shows the elapsed time since puncturing the eyelid in the perpendicular set of trials, and the top x-axis (red) shows the elapsed time since puncture in the parallel set. The dual-axis is to allow a view of the perfusion over the entire experiment, while bearing in mind that the thermocouple in the eyelid was removed and then embedded once more after about 150 min. Over elapsed experiment time, the eyelid perfusion has a general downward trend, if the sudden increase in perfusion after puncturing the orbicularis anew is treated as extraneous (naturally, a puncture wound produces a higher local perfusion). The effective perfusion rates do not correlate perfectly with the temperature rises observed throughout the respective trials as shown in FIGS. 33a and 33b. However, the decrease in w over time throughout each set of trials is expected for increasing $\Delta T$ according to equation 8, assuming no change in the thermal diffusivity throughout the porcine tissue.

FIG. 35 shows computed effective blood perfusion rates in the eyelid for the two sets of trials over elapsed time since puncturing the orbicularis in the perpendicular and parallel experiments. Error bars show the standard deviation about the mean value computed from multiple windows in time.

There are biological factors to consider that may affect both the temperature rise and the perfusion rates. For one, prolonged anaesthesia depresses heart and breathing rates. If the basal corneal temperatures in FIG. 30b are an indicator of the core temperature, they show that the physiological effects of anaesthesia are pronounced over time. It is also intuitive to expect that the initial biological response of piercing the eyelid with a needle affects the perfusion in the vicinity of the puncture wound. The initial bleeding from damaged vasculature and subsequent localized blood coagulation and clot formation may change the ultrasonic absorption or heat capacity of the tissue. The lack of a clear correlation between the perfusion and the temperature rises achieved lead us to believe that other biological responses affect the steady state temperature.

Figure 36B:
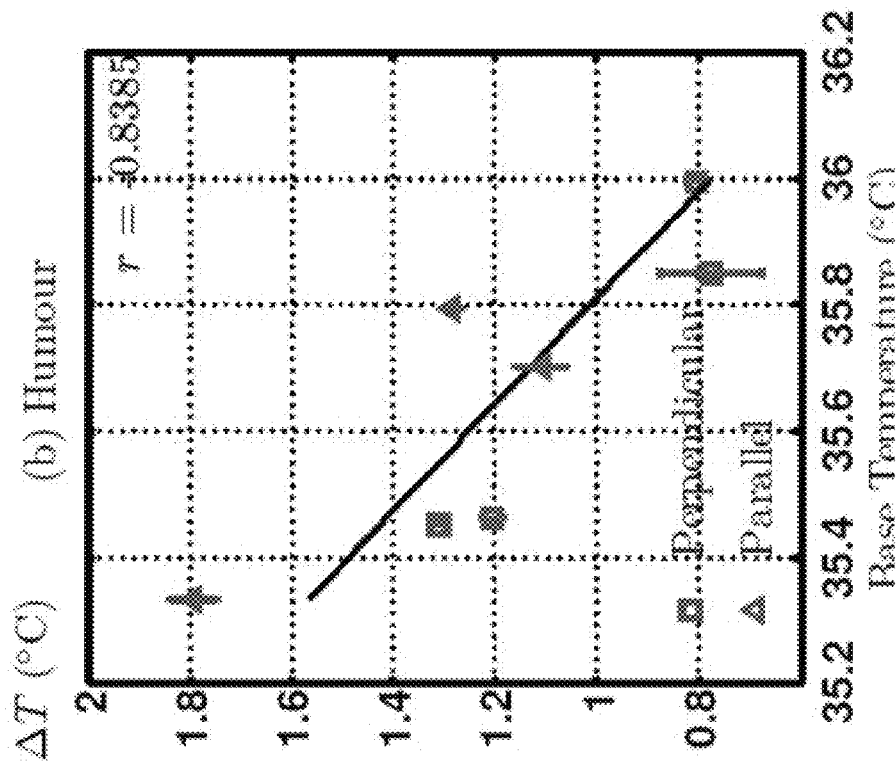
Figure 36A:
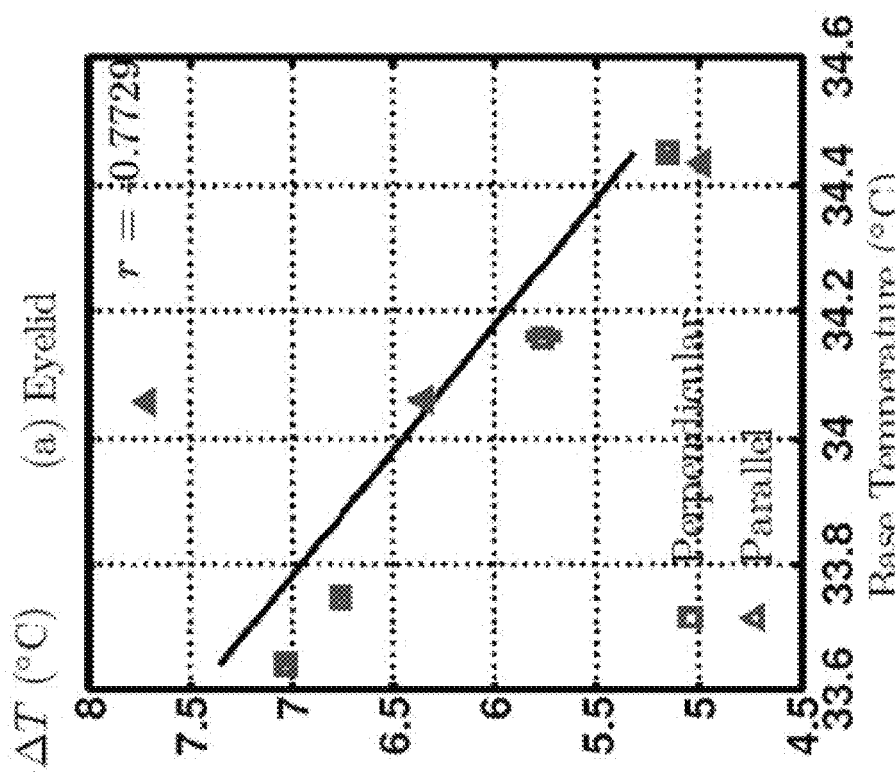

FIG. 36 shows the temperature rises plotted against the equilibrium temperature immediately before sonication for all trials in the eyelid (FIG. 36a) and humour (FIG. 36b). Decreasing basal temperature before sonication is related to the magnitude of $\Delta T$, as evidenced by the computed Pearson correlation coefficients r, shown in the top right corner of the plots.

FIG. 36 shows temperature rise correlated with basal temperature in for the eyelid (FIG. 36a), and humour (FIG. 36b). The pearson correlation coefficient r is shown at the top right for both perpendicular and parallel trials combined. The strong negative correlation indicated by these r values suggests that basal temperature is a factor in the magnitude of the observed $\Delta T$.

The primary aim of hyperthermia therapy for treating obstructive Meibomian Gland Dysfunction is to liquify the keratinized meibum within the meibomian glands. An example temperature regime is a 5-7 degrees Celsius rise, which raises the glands' temperature to 41-43 degrees Celsius. In FIG. 33, the increasing $\Delta T$ over time is thought to be the product of the biological effects of prolonged anaesthesia, decreasing basal temperature, and blood perfusion.

The safety of the cornea is a factor; the temperature rise within it should be as low as reasonably possible, not exceeding 6 degrees Celsius, for example.

In FIG. 29(b), the ultrasonic field intensity at the corneal face of the lens was found to be more than 13 dB weaker than the field measured at the tarsal face. This corresponds to less than a quarter of the energy transmitted at the limbal point in FIG. 29(b). That acoustic fields are produced at the corneal face is confirmed by the shape of the hyperthermia curves in FIGS. 31a and 31b: both subplots of the (a) eyelid and (b) cornea have the similar heating and cooling characteristics. However, while ultrasound is reaching the aqueous humour, it has only a minor effect on the corneal temperature: no temperature rise greater than 2 degrees Celsius was observed, and all but one of the hyperthermia trials were below 1.5 degree Celsius during steady state conditions. The heating observed in the cornea was generally less than a quarter of that measured in the eyelid, which agrees with the relative energy deposition when the higher acoustic attenuation of the eyelid is taken into consideration. Naturally, in making measurements of the aqueous humour in the anterior chamber, the assumption that the humour is in thermal equilibrium with the cornea must be stressed. While the cornea is in direct contact with the tarsal lens, the assumption of thermal equilibrium is thought reasonable, since the cornea may be composed of nearly 80% water.

The meibomian glands may be located along the entire length of the marginal eyelid—a length of about 25 mm. The piston transducer of the example prototype has a radius of only 3.25 mm. A larger radius may also be used in some examples. The field intensity in FIGS. 29a and 29b may decline steeply to −6 dB beyond 4 mm radially outward from the transducer centre: thus the prototype applies direct heat to only a third of the meibomian glands located at the centre of the superior and inferior eyelid margins. The remedy for this may be the design of a limbal point located farther from the epicentre of the lens, allowing for a larger diameter transducer to be contained within the lens. While such a design may be unable to directly heat the entire length of the margin, heat diffusion radially outwards will aid in the heating of the meibomian glands located near the lateral and medial canthi. Other designs and dimensions may be used and these are examples only.

This is an example prototype design for an ultrasonic device for the hyperthermia treatment of obstructive MGD, other variants may also be used. The example device may include of a piezoelectric transducer contained within a contact lens with an internal air gap, such that the two faces of the lens abut the tarsus and the sclera, and the transducer is mechanically fixed to the posterior tarsal face, such that the air gap provides the transducer with an air backing. This reflects acoustic waves towards the tarsus and away from the cornea, preventing corneal temperature elevation from direct ultrasound. The target heating in the eyelid may be 5-7 degrees Celsius, with minimal corneal temperature rise. This an example range and other temperature targets may be used in accordance with modified treatment parameters.

Further, the transducer may be separate from the lens as described herein and in some embodiments may not be located within the chamber of air of the air gap lens.

The example prototype of this design may be constructed from contact lenses and a PZT piston transducer of radius 3.25 mm, as a non-limiting illustrative experimental example. Field intensity measurements showed that the air gap was effective at preventing direct ultrasonic transmission into the corneal apex, though some acoustic energy at −13 dB was detectable at the limbal point where the two contact lenses were epoxied. In an in vivo experiment on a porcine subject, it was found that a 5-8 degrees Celsius equilibrium temperature rise in the eyelid may be achievable in a clinical timeframe of 10-15 minutes. During this time, the corneal temperature did not rise more than 2 degrees Celsius, which is well within the established safety limits of <40 degrees Celsius. The temperature curves obtained from the bare wire thermocouples used in the experiment were examined for evidence of temperature artifacts, though none of the telltale signs were observed. However, a general increase in temperature rise over experimental time was noted. Analysis of the blood perfusion in the eyelid may show that it may decrease with time, but that puncturing the eyelid increased the perfusion immediately afterward. The increasing temperature rises also correlated with a decreasing basal temperature of the eyelid and humour. Hence it is thought likely that biological factors associated with anaesthsia and piercing the eyelid and embedding the thermocouple may impact the results.

Other examples embodiments may involve refinement of the example prototype and extended testing. A device constructed from custom lenses may allow for a transducer with a larger surface area, targeting a greater portion of the meibomian glands along the length of the eyelid margins. A separate lens and transducer system may also allow for a transducer with a larger surface area. In some examples, infrared thermography may be used to measure the eyelid surface temperature, which may eliminate the biological effects of embedding the thermocouple within the eyelid. Though thermography may detect the surface temperature of the eyelid, this may give a lower bound on the temperature of the tarsus, and an upper bound may be may be approximated from thermal models of the tissue in conjunction with these measurements.

Embodiments have been described by way of example only, and various modification and variations may be made to these exemplary embodiments.

The invention claimed is:

1. A method comprising:
   coupling at least one ultrasound transducer of an ultrasound device to at least a portion of an eyelid using a coupling medium, wherein the ultrasound device comprises at least one ultrasound transducer for supplying ultrasound waves to an area proximate to the portion of the eyelid according to treatment parameters;
   placing an air gap lens over an eye globe and under the eyelid to protect ocular tissue, wherein the air gap lens comprises lens layers that connect at ends of the lens layers to define an enclosed chamber of air, wherein the lens layers and the enclosed chamber of air provide a barrier to the ultrasound waves;
   positioning a measurement device on or within the air gap lens to capture measurement data, the measurement data comprising temperature data;
   operating the ultrasound device in a therapeutic mode to heat the area proximate to the portion of the eyelid by propagating vibrational ultrasound waves to the area proximate to the portion of the eyelid using the coupling medium and the at least one ultrasound transducer according to the treatment parameters, the portion of the eyelid including a gland blocked by solidified fats, the treatment parameters defining a treatment frequency for the ultrasound waves within a frequency range of 0.2 MHz to 50 MHz and a treatment period proportional to the treatment frequency;
   concurrently operating the ultrasound device in a diagnostic mode to image the area proximate to the portion of the eyelid using an ultrasound imaging camera to provide real-time imaging during treatment;
   providing acoustic impedance using the lens layers and the enclosed chamber of air as the ultrasound waves do not propagate the chamber of air, wherein the air gap lens protects ocular tissue of an eye;
   providing, by the measurement device, the measurement data to the ultrasound device, wherein the measurement device comprises a thermal couple;

comparing the temperature data to a predetermined safety range;
generating a first warning alert to adjust the treatment parameters or shutting down the at least one ultrasound transducer upon determining that the temperature data is above the predetermined safety range;
generating a second warning alert to adjust the treatment parameters and adjusting the at least one ultrasound transducer so that the temperature data is within the predetermined safety range upon determining that the temperature data is below the predetermined safety range;
liquefying the solidified fats blocking the gland using the propagating vibrational ultrasound waves to provide heat energy to the solidified fats; and
mobilizing the liquefied fats to promote clearance from the gland using oscillations supplied by the propagating vibrational ultrasound waves that create microcavitation and acoustic streaming of the liquefied fats.

2. The method of claim 1, further comprising providing the at least one ultrasound transducer separate from the air gap lens.

3. The method of claim 1, further comprising providing the at least one ultrasound transducer of a longer length than the air gap lens.

4. The method of claim 1, wherein the at least one ultrasound transducer comprises polyvinylidene fluoride film.

5. A system for treating an eye condition comprising:
an ultrasound device comprising at least one ultrasound transducer for supplying vibrational ultrasound waves to an area proximate to a portion of an eyelid according to treatment parameters, the at least one ultrasound transducer adapted to couple to the portion of the eyelid using a coupling medium, the portion of the eyelid including a gland blocked by solidified fats, the treatment parameters defining a treatment frequency for the ultrasound waves within a frequency range of 0.2 MHz to 50 MHz and a treatment period proportional to the treatment frequency; and
an air gap lens to protect ocular tissue of an eye, wherein the lens is configured to form an enclosed chamber of air between connected ends of lens layers, wherein the lens layers and the chamber of air provide a barrier to the ultrasound waves, wherein the lens layers and the enclosed chamber of air supply acoustic impedance so that the ultrasound waves do not propagate the chamber of air;
wherein the ultrasound waves liquefy the solidified fats blocking the gland by providing heat energy to the solidified fats and mobilize the liquefied fats to promote clearance from the gland using oscillations supplied by the ultrasound waves that create microcavitation and acoustic streaming of the liquefied fats;
a measurement device positioned on or within the air gap lens to capture measurement data, the measurement data comprising temperature data, the measurement device configured to provide the measurement data to the ultrasound device to compare the temperature data to a predetermined safety range, wherein the device generates a first warning alert to adjust the treatment parameters or shut down the at least one ultrasound transducer upon determining that the temperature data is above the predetermined safety range, and generates a second warning alert to adjust the treatment parameters and adjusts the at least one ultrasound transducer so that the temperature data is within the predetermined safety range upon determining that the temperature data is below the predetermined safety range;
wherein the measurement device comprises a thermal couple;
an ultrasound imaging camera, wherein the ultrasound device is configured to operate in a therapeutic mode to heat the area proximate to the portion of the eyelid using the ultrasound waves and a diagnostic mode to image the area proximate to the portion of the eyelid using the ultrasound imaging camera, wherein the ultrasound device is configured to operate in diagnostic mode and therapeutic mode concurrently to provide real-time imaging during treatment.

6. The system of claim 5, wherein the at least one ultrasound transducer is separate from the air gap lens.

7. The system of claim 5, wherein the at least one ultrasound transducer is of a longer length than the air gap lens.

8. The system of claim 5, wherein the at least one ultrasound transducer comprises polyvinylidene fluoride film.

9. The system of claim 5, wherein the at least one ultrasound transducer is a PZT transducer.

10. The system of claim 5, wherein the lens comprises an absorptive material to block penetration of ocular tissue by the ultrasound waves.

11. The system of claim 5, wherein the chamber of air blocks penetration of ocular tissue by the ultrasound waves.

12. The system of claim 5, further comprising a lens speculum to elevate the eyelid from an eye globe and create an airspace between the eye globe and eyelid.

13. The system of claim 5, wherein the at least one ultrasound transducer provides the treatment frequency ranging from 0.2 to 10 MHz.

* * * * *